US012678497B2

(12) United States Patent
Sahin et al.

(10) Patent No.: US 12,678,497 B2
(45) Date of Patent: Jul. 14, 2026

(54) COMPOSITIONS COMPRISING NON-IMMUNOGENIC RNA ENCODING IMMUNOGENIC EPITOPES AND INTERFERON ALPHA

(71) Applicants: BIONTECH SE, Mainz (DE); TRON—TRANSLATIONALE ONKOLOGIE AN DER UNIVERSITÄTSMEDIZIN DER JOHANNES GUTENBERG-UNIVERSITÄT MAINZ, Mainz (DE)

(72) Inventors: Ugur Sahin, Mainz (DE); Lena Mareen Kranz, Mainz (DE); Mustafa Diken, Mainz (DE); Lina Hilscher, Dortmund (DE); Sebastian Kreiter, Mainz (DE)

(73) Assignees: BioNTech SE, Mainz (DE); TRON - Translationale Onkologie an der Universitätsmedizin der Johannes Gutenberg-Universität Mainz gemeinnützige GmbH, Mainz (DE)

( * ) Notice: Subject to any disclaimer, the term of this patent is extended or adjusted under 35 U.S.C. 154(b) by 851 days.

(21) Appl. No.: 17/907,013

(22) PCT Filed: Mar. 30, 2021

(86) PCT No.: PCT/EP2021/058297
§ 371 (c)(1),
(2) Date: Sep. 22, 2022

(87) PCT Pub. No.: WO2021/198258
PCT Pub. Date: Oct. 7, 2021

(65) Prior Publication Data

US 2023/0145774 A1 May 11, 2023

(30) Foreign Application Priority Data

Mar. 31, 2020 (WO) ................ PCT/EP2020/059170

(51) Int. Cl.

| | |
|---|---|
| ***A61K 39/39*** | (2006.01) |
| ***A61K 39/00*** | (2006.01) |
| ***A61P 37/02*** | (2006.01) |

(52) U.S. Cl.
CPC .......... *A61K 39/39* (2013.01); *A61K 39/0011* (2013.01); *A61P 37/02* (2018.01); *A61K 2039/55522* (2013.01); *A61K 2039/55527* (2013.01); *A61K 2039/55538* (2013.01); *A61K 2039/55561* (2013.01)

(58) Field of Classification Search
CPC ................ A61K 39/39; A61K 39/0011; A61K 2039/53; A61P 37/02
See application file for complete search history.

(56) References Cited

U.S. PATENT DOCUMENTS

| | | | |
|---|---|---|---|
| 2018/0311343 | A1 | 11/2018 | Huang et al. |
| 2019/0358314 | A1 | 11/2019 | Weissman et al. |

FOREIGN PATENT DOCUMENTS

| | | | |
|---|---|---|---|
| WO | 2017036889 | A1 | 3/2017 |
| WO | 2017070623 | A1 | 4/2017 |
| WO | 2019154985 | A1 | 8/2019 |
| WO | 2021198258 | A1 | 10/2021 |

OTHER PUBLICATIONS

Sergeeva et al., Biochemistry (Moscow), 81 (7), 709-722 (2016).
International Search Report for International Application No. PCT/EP2021/058297, dated Jul. 2, 2021 (7 pages).
Written Opinion for International Application No. PCT/EP2021/058297, dated Jul. 2, 2021 (7 pages).

*Primary Examiner* — Elly-Gerald Stoica
(74) *Attorney, Agent, or Firm* — Neal, Gerber & Eisenberg LLP

(57) ABSTRACT

The present disclosure relates to methods and agents for antigen vaccination and inducing effective antigen-specific immune effector cell responses such as T cell responses. Specifically, the present disclosure relates to methods comprising administering to a subject (i) non-immunogenic RNA encoding a peptide or protein comprising an epitope for inducing an immune response against an antigen in the subject, i.e., non-immunogenic RNA encoding vaccine antigen; and (ii) an immunostimulant or RNA encoding an immunostimulant. Administering to the subject non-immunogenic RNA encoding vaccine antigen may provide (following expression of the RNA by appropriate target cells) vaccine antigen for stimulation, priming and/or expansion of immune effector cells and, thus, may induce an immune response against vaccine antigen (and disease-associated antigen) in the subject.

10 Claims, 6 Drawing Sheets

Specification includes a Sequence Listing.

SEQUENCE LISTING

```
<160> NUMBER OF SEQ ID NOS: 4

<210> SEQ ID NO 1
<211> LENGTH: 8
<212> TYPE: PRT
<213> ORGANISM: Artificial Sequence
<220> FEATURE:
<223> OTHER INFORMATION: Epitope

<400> SEQUENCE: 1

Ser Ile Ile Asn Phe Glu Lys Leu
1               5


<210> SEQ ID NO 2
<211> LENGTH: 17
<212> TYPE: PRT
<213> ORGANISM: Artificial Sequence
<220> FEATURE:
<223> OTHER INFORMATION: Epitope

<400> SEQUENCE: 2

Ile Ser Gln Ala Val His Ala Ala His Ala Glu Ile Asn Glu Ala Gly
1               5                   10                  15

Arg


<210> SEQ ID NO 3
<211> LENGTH: 20
<212> TYPE: PRT
<213> ORGANISM: Artificial Sequence
<220> FEATURE:
<223> OTHER INFORMATION: GS Linker

<400> SEQUENCE: 3

Gly Gly Ser Gly Gly Gly Gly Ser Gly Gly Gly Gly Ser Gly Gly Gly
1               5                   10                  15

Gly Ser Gly Gly
            20


<210> SEQ ID NO 4
<211> LENGTH: 190
<212> TYPE: PRT
<213> ORGANISM: Artificial Sequence
<220> FEATURE:
```

-continued

```
<223> OTHER INFORMATION: Interferon

<400> SEQUENCE: 4

Met Gly Ala Met Ala Pro Arg Thr Leu Leu Leu Leu Leu Ala Ala Ala
1               5                   10                  15

Leu Ala Pro Thr Gln Thr Arg Ala Gly Pro Gly Ser Cys Asp Leu Pro
            20                  25                  30

His Thr Tyr Asn Leu Gly Asn Lys Arg Ala Leu Thr Val Leu Glu Glu
        35                  40                  45

Met Arg Arg Leu Pro Pro Leu Ser Cys Leu Lys Asp Arg Lys Asp Phe
    50                  55                  60

Gly Phe Pro Leu Glu Lys Val Asp Asn Gln Gln Ile Gln Lys Ala Gln
65                  70                  75                  80

Ala Ile Leu Val Leu Arg Asp Leu Thr Gln Gln Ile Leu Asn Leu Phe
                85                  90                  95

Thr Ser Lys Asp Leu Ser Ala Thr Trp Asn Ala Thr Leu Leu Asp Ser
            100                 105                 110

Phe Cys Asn Asp Leu His Gln Gln Leu Asn Asp Leu Lys Ala Cys Val
        115                 120                 125

Met Gln Glu Pro Pro Leu Thr Gln Glu Asp Ser Leu Leu Ala Val Arg
    130                 135                 140

Thr Tyr Phe His Arg Ile Thr Val Tyr Leu Arg Lys Lys Lys His Ser
145                 150                 155                 160

Leu Cys Ala Trp Glu Val Ile Arg Ala Glu Val Trp Arg Ala Leu Ser
                165                 170                 175

Ser Ser Thr Asn Leu Leu Ala Arg Leu Ser Glu Glu Lys Glu
            180                 185                 190
```

COMPOSITIONS COMPRISING NON-IMMUNOGENIC RNA ENCODING IMMUNOGENIC EPITOPES AND INTERFERON ALPHA

CROSS-REFERENCE TO RELATED APPLICATIONS

This application is a National Stage Entry of International Application Number PCT/EP2021/058297, which was filed on Mar. 30, 2021 and claimed priority to International Application Number PCT/EP2020/059170, which was filed on Mar. 31, 2020. The contents of each of the aforementioned applications are incorporated herein by reference in their entireties.

TECHNICAL FIELD

The present disclosure relates to methods and agents for antigen vaccination and inducing effective antigen-specific immune effector cell responses such as T cell responses. These methods and agents are, in particular, useful for the treatment of diseases characterized by diseased cells expressing an antigen the immune effector cells are directed to. Specifically, the present disclosure relates to methods comprising administering to a subject (i) non-immunogenic RNA encoding a peptide or protein comprising an epitope for inducing an immune response against an antigen in the subject, i.e., non-immunogenic RNA encoding vaccine antigen; and (ii) an immunostimulant or RNA encoding an immunostimulant. Administering to the subject non-immunogenic RNA encoding vaccine antigen may provide (following expression of the RNA by appropriate target cells) vaccine antigen for stimulation, priming and/or expansion of immune effector cells and, thus, may induce an immune response against vaccine antigen (and disease-associated antigen) in the subject. In one embodiment, the immune effector cells carry an antigen receptor such as T cell receptor (TCR) or chimeric antigen receptor (CAR) having a binding specificity for the antigen or a procession product thereof. In one embodiment, the immune effector cells are genetically modified to express the antigen receptor. Such genetic modification may be effected ex vivo or in vitro and subsequently the immune effector cells may be administered to a subject in need of treatment and/or may be effected in vivo in a subject in need of treatment. The immune effector cells may be from the subject in need of treatment and may be endogenous in the subject in need of treatment. The antigen receptor of the immune effector cells may target antigen which is associated with a disease.

BACKGROUND

The immune system plays an important role in cancer, autoimmunity, allergy as well as in pathogen-associated diseases. T cells and NK cells are important mediators of anti-tumor immune responses. CD8+ T cells and NK cells can directly lyse tumor cells. CD4+ T cells, on the other hand, can mediate the influx of different immune subsets including CD8+ T cells and NK cells into the tumor. CD4+ T cells are able to license dendritic cells (DCs) for the priming of anti-tumor CD8+ T cell responses and can act directly on tumor cells via IFNγ mediated MHC upregulation and growth inhibition. CD8+ as well as CD4+ tumor specific T cell responses can be induced via vaccination or by adoptive transfer of T cells. In the context of an mRNA based vaccine platform, mRNA may be delivered via liposomal formulation (RNA-lipoplexes, RNA-LPX) into antigen-presenting cells located in secondary lymphoid organs without requirement for any additional adjuvant for immune stimulation (Kreiter, S. et al. Nature 520, 692-696 (2015); Kranz, L. M. et al. Nature 534, 396-401 (2016)).

Induction of effective T cell responses requires both the presentation of the antigen on MHC molecules of mature cDCs, as well as co-stimulation in the presence of a polarizing cytokine and chemokine environment. Antigen presentation in the absence of immune stimulation may result in anergy or tolerance. Innate recognition of microbial pathogens or danger-associated molecular patterns (DAMPs) by pattern recognition receptors (PRRs) in immature cDCs naturally leads to upregulation of genes associated with migration, presentation, co-stimulation and cytokine secretion. CD8+ as well as CD4+ tumor-specific T cell responses can be induced by vaccination. Adjuvants such as aluminum salts, monophosphoryl lipid A or toll like receptor (TLR) agonists are commonly co-administered with vaccines to enhance their immunogenicity (Coffman, Robert L. et al., 2010, *Immunity* 33(4):492-503).

In previous studies, we optimized antigen-encoding RNA for intracellular stability, translational efficiency (Holtkamp, Silke et al., 2006, Blood 108(13):4009-17; Kuhn, A N et al., 2010, *Gene Therapy* 17(8):961-71; Orlandini von Niessen, Alexandra G. et al., 2019, *Molecular Therapy* 27(4):824-36) and enhanced MHC class I and II presentation (Kreiter, S. et al., 2008, The Journal of Immunology 180(1):309-18). Intravenously administered liposomally formulated RNA (RNA-LPX) was designed to target translation and MHC presentation of the encoded antigen specifically to resident DCs within lymphoid organs by employing a negative net charge (Kranz, Lena Mareen et al., 2016, *Nature* 534(7607):396-401). RNA-LPX internalized by DCs mimics infectious non-self and functions as natural TLR7/8 ligand, triggering a strong type I IFN dominated innate response. Type I IFN was found to be of major importance in the induction of functional anti-tumoral T cells in therapeutic mouse models (Kranz, Lena Mareen et al., 2016, Nature 534(7607):396-401), which is supported by preliminary findings in ongoing clinical trials in patients with solid cancers (NCT02410733, NCT03289962, NCT03418480, NCT02316457).

Our RNA-LPX vaccine platform consists of non-nucleoside-modified RNA (standard RNA, stdRNA) not subjected to double stranded RNA purification which provides the target identity, i.e. the antigen, and the adjuvant concomitantly. Consequently, the antigen dose applied cannot be separated from the RNA-dependent adjuvant effect, and the adjuvanticity increases with the antigen RNA dose. While increasing the antigen dose may be favorable, ever increasing adjuvanticity may cause unwanted immune-related adverse effects. Individual patient sensitivity to adjuvants can vary greatly, and may turn dose-limiting before full activity of the RNA vaccine, i.e. optimal antigen-specific T cell immunity, is reached.

For optimal vaccine design, it would be useful to decouple antigen information and adjuvanticity. Vaccine RNA that is no longer triggering innate immune activation would allow extended dose escalation without the limitation of RNA-mediated adverse effects, and could be supported by adequate adjuvant amounts that take into account individual adjuvant sensitivity.

The present disclosure provides a novel method of RNA vaccination where the antigen information is detached from RNA intrinsic adjuvanticity by the usage of antigen-encoding RNA that no longer acts as an adjuvant, and combination thereof with immunostimulants, in particular RNA-encoded immunostimulants. The type of immunostimulant can be selected based on the intended physiological action, e.g. pro-inflammatory when treating infections or cancer, or anti-inflammatory when treating autoimmune diseases. Such RNA-encoded immunostimulants may be delivered independently from the RNA vaccine and can be targeted to the tissue of interest, e.g. by adequate formulations. The concept of influencing the strength and the type of vaccine-induced immunity according to need can be called 'immunotuning'.

In order to reduce the immunogenicity of vaccine RNA, nucleosides can be modified and residual double-stranded RNA can be eliminated. We synthesized N1-methyl-pseudourine-modified and cellulose-purified vaccine RNA (modified RNA, modRNA) (Andries, Oliwia et al., 2015, *Journal of Controlled Release: Official Journal of the Controlled Release Society* 217:337-44; Baiersdörfer, Markus et al., 2019, Molecular Therapy—Nucleic Acids 15(April); Pardi, Norbert et al., 2015, *Journal of Controlled Release: Official Journal of the Controlled Release Society* 217:345-51). For proof of concept that the addition of rationally selected immunostimulants to modRNA can provide sufficient and tunable adjuvanticity, we selected the cytokine interferon α (IFNα), which is well-known for its pro-inflammatory activity, its role in antiviral defense, and has been shown by us to be critical for the function of our RNA-LPX vaccine (Kranz, Lena Mareen et al., 2016, Nature 534(7607):396-401).

We demonstrate that compared to our stdRNA, modRNA restricts immune activation and systemic IFNα release. This indicates that adjuvanticity can be controlled by the use of modRNA. The immunosilent environment induced by modRNA can be mimicked by blocking Interferon α receptor 1 (IFNAR1) signaling, indicating that the lack of IFNα in response to modRNA vaccination causes the immunosilent phenotype. modRNA induces less T cell proliferation and constrains T cell differentiation into functional, effector cytokine-producing effector T cells.

Based on our finding that IFNα is essential for creating the pro-inflammatory environment required for vaccine activity, we demonstrate that RNA encoding IFNα provides dose-dependent and titratable immune activation. As hypothesized, combination of modRNA vaccination with IFNα RNA treatment restores not only vaccine RNA induced T cell proliferation, but also differentiation, function and memory development of antigen-specific CD8+ T cells, in an IFNα RNA dose-dependent manner.

SUMMARY

The present invention generally embraces the immunotherapeutic treatment of a subject comprising the administration of (i) non-immunogenic RNA encoding a peptide or protein comprising an epitope for inducing an immune response against an antigen in the subject, i.e., non-immunogenic RNA encoding vaccine antigen; and (ii) an immunostimulant or RNA encoding an immunostimulant. The immunotherapies described herein comprise vaccine therapies and may further comprise cell-based cancer immunotherapies such as TIL- or T cell-based treatments, for example TCR- or CAR-transgenic T cell-based treatments using, for example, autologous cells. In general, immune effector cells that are stimulated using the treatments described herein may target cells expressing an antigen such as diseased cells, in particular cancer cells expressing a tumor antigen. The target cells may express the antigen on the cell surface or may present a procession product of the antigen. In one embodiment, the antigen is a tumor-associated antigen and the disease is cancer. Such treatment provides for the selective eradication of cells that express an antigen, thereby minimizing adverse effects to normal cells not expressing the antigen. The immune effector cells (optionally genetically modified to express an antigen receptor) are targeted to the antigen or a procession product thereof and thus, to a target cell population or target tissue expressing the antigen. Such immune effector cells may be administered to a subject in need of treatment or may be endogenous to a subject in need of treatment. In one embodiment, the immune effector cells carry an antigen receptor such as T cell receptor (TCR) or chimeric antigen receptor (CAR) having a binding specificity for the target antigen or a procession product thereof. In one embodiment, the immune effector cells are genetically modified to express the antigen receptor. Such genetic modification to express an antigen receptor may be effected ex vivo or in vitro and subsequently the immune effector cells may be administered to a subject in need of treatment or may be effected in vivo in a subject in need of treatment, or may be effected by a combination of ex vivo or in vitro and in vivo modification. Non-immunogenic RNA encoding vaccine antigen is administered to provide (following expression of the polynucleotide by appropriate target cells) antigen for stimulation, priming and/or expansion of the immune effector cells, which are targeted to target antigen or a procession product thereof. In one embodiment, the immune response which is to be induced according to the present disclosure is an immune response to a target cell population or target tissue expressing an antigen the immune effector cells are directed to. In one embodiment, the immune response which is to be induced according to the present disclosure is a T cell-mediated immune response. In one embodiment, the immune response is an anti-tumor immune response and the target cell population or target tissue is tumor cells or tumor tissue.

The methods and agents described herein are particularly effective if the immunostimulant is attached to a pharmacokinetic modifying group (hereafter referred to as "extended-pharmacokinetic (PK)" immunostimulant). The methods and agents described herein are particularly effective if the immunostimulant is administered in the form of RNA encoding an immunostimulant. In one embodiment, said RNA is targeted to the liver for systemic availability. Liver cells can be efficiently transfected and are able to produce large amounts of protein. Vaccine antigen-encoding RNA is preferably targeted to secondary lymphoid organs.

In one aspect, provided herein is a method for inducing an immune response in a subject comprising administering to the subject:

(i) non-immunogenic RNA encoding a peptide or protein comprising an epitope for inducing an immune response against an antigen in the subject; and (ii) an immunostimulant or RNA encoding an immunostimulant.

In one embodiment, the subject has a disease, disorder or condition associated with expression or elevated expression of an antigen.

In one aspect, provided herein is a method for treating a subject having a disease, disorder or condition associated with expression or elevated expression of an antigen comprising administering to the subject:

(i) non-immunogenic RNA encoding a peptide or protein comprising an epitope for inducing an immune response against the antigen in the subject; and (ii) an immunostimulant or RNA encoding an immunostimulant.

In one embodiment, the immune response is a T cell-mediated immune response.

In one embodiment, the immune response comprises the generation of antigen-specific T cells.

In one embodiment, the antigen is a tumor-associated antigen.

In one embodiment, the disease, disorder or condition is cancer.

In one embodiment, the method comprises administering to the subject:

(i) the non-immunogenic RNA encoding a peptide or protein comprising an epitope; and (ii) RNA encoding an immunostimulant.

In one embodiment, the RNA encoding an immunostimulant is non-immunogenic.

In one embodiment, the non-immunogenic RNA when administered results in reduced activation of dendritic cells, activation of T cells and/or secretion of IFN-alpha compared to standard RNA.

In one embodiment, the non-immunogenic RNA is rendered non-immunogenic by the incorporation of modified nucleosides and the removal of double-stranded RNA (dsRNA).

In one embodiment, the modified nucleosides suppress RNA-mediated activation of innate immune receptors.

In one embodiment, the modified nucleosides comprise a replacement of one or more uridines with a nucleoside comprising a modified nucleobase.

In one embodiment, the modified nucleobase is a modified uracil.

In one embodiment, the nucleoside comprising a modified nucleobase is selected from the group consisting of 3-methyl-uridine (m3U), 5-methoxy-uridine (mo5U), 5-aza-uridine, 6-aza-uridine, 2-thio-5-aza-uridine, 2-thio-uridine (s2U), 4-thio-uridine (s4U), 4-thio-pseudouridine, 2-thio-pseudouridine, 5-hydroxy-uridine (ho5U), 5-aminoallyl-uridine, 5-halo-uridine (e.g., 5-iodo-uridine or 5-bromo-uridine), uridine 5-oxyacetic acid (cmo5U), uridine 5-oxyacetic acid methyl ester (mcmo5U), 5-carboxymethyl-uridine (cm5U), 1-carboxymethyl-pseudouridine, 5-carboxyhydroxymethyl-uridine (chm5U), 5-carboxyhydroxymethyl-uridine methyl ester (mchm5U), 5-methoxycarbonylmethyl-uridine (mcm5U), 5-methoxycarbonylmethyl-2-thio-uridine (mcm5s2U), 5-aminomethyl-2-thio-uridine (nm5s2U), 5-methylaminomethyl-uridine (mnm5U), 1-ethyl-pseudouridine, 5-methylaminomethyl-2-thio-uridine (mnm5s2U), 5-methylaminomethyl-2-seleno-uridine (mnm5se2U), 5-carbamoylmethyl-uridine (ncm5U), 5-carboxymethylaminomethyl-uridine (cmnm5U), 5-carboxymethylaminomethyl-2-thio-uridine (cmnm5s2U), 5-propynyl-uridine, 1-propynyl-pseudouridine, 5-taurinomethyl-uridine (τm5U), 1-taurinomethyl-pseudouridine, 5-taurinomethyl-2-thio-uridine (τm5s2U), 1-taurinomethyl-4-thio-pseudouridine, 5-methyl-2-thio-uridine (m5s2U), 1-methyl-4-thio-pseudouridine (m1s4ψ), 4-thio-1-methyl-pseudouridine, 3-methyl-pseudouridine (m3ψ), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyl-dihydrouridine (m5D), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine, 3-(3-amino-3-carboxypropyl) uridine (acp3U), 1-methyl-3-(3-amino-3-carboxypropyl) pseudouridine (acp3 ψ), 5-(isopentenylaminomethyl)uridine (inm5U), 5-(isopentenylaminomethyl)-2-thio-uridine (inm5s2U), α-thio-uridine, 2'-O-methyl-uridine (Um), 5,2'-O-dimethyl-uridine (m5Um), 2'-O-methyl-pseudouridine (ψm), 2-thio-2'-O-methyl-uridine (s2Um), 5-methoxycarbonylmethyl-2'-O-methyl-uridine (mcm5Um), 5-carbamoylmethyl-2'-O-methyl-uridine (ncm5Um), 5-carboxymethylaminomethyl-2'-O-methyl-uridine (cmnm5Um), 3,2'-O-dimethyl-uridine (m3Um), 5-(isopentenylaminomethyl)-2'-O-methyl-uridine (inm5Um), 1-thio-uridine, deoxythymidine, 2'-F-ara-uridine, 2'-F-uridine, 2'-OH-ara-uridine, 5-(2-carbomethoxyvinyl) uridine, and 5-[3-(1-E-propenylamino)uridine.

In one embodiment, the nucleoside comprising a modified nucleobase is pseudouridine (ψ), N1-methyl-pseudouridine (m1ψ) or 5-methyl-uridine (m5U).

In one embodiment, the nucleoside comprising a modified nucleobase is 1-methyl-pseudouridine.

In one embodiment, the non-immunogenic RNA encoding a peptide or protein comprising an epitope, and/or the RNA encoding an immunostimulant, is mRNA.

In one embodiment, the non-immunogenic RNA encoding a peptide or protein comprising an epitope, and/or the RNA encoding an immunostimulant, is in vitro transcribed RNA.

In one embodiment, the immunostimulant is a pro-inflammatory or anti-inflammatory immunostimulant.

In one embodiment, the non-immunogenic RNA encoding a peptide or protein comprising an epitope is administered in a formulation for targeting the lymphatic system.

In one embodiment, the non-immunogenic RNA encoding a peptide or protein comprising an epitope is administered in a formulation for targeting dendritic cells.

In one embodiment, the dendritic cells are immature dendritic cells.

In one embodiment, the immunostimulant comprises a cytokine or a variant thereof.

In one embodiment, the cytokine comprises a type I interferon or a variant thereof.

In one embodiment, the type I interferon comprises interferon-α or a variant thereof.

In one embodiment, the cytokine comprises an interleukin or a variant thereof.

In one embodiment, the cytokine supports T cell priming.

In one embodiment, the cytokine comprises IL12, IL15 or a variant thereof.

In one embodiment, the cytokine supports T cell proliferation and/or maintenance.

In one embodiment, the cytokine comprises IL2, IL7 or a variant thereof.

In one embodiment, the immunostimulant is extended pharmacokinetic (PK) immunostimulant. In one embodiment, the extended-PK immunostimulant comprises a fusion protein. In one embodiment, the fusion protein comprises a moiety of immunostimulant and a moiety selected from the group consisting of serum albumin, an immunoglobulin fragment, transferrin, Fn3, and variants thereof. In one embodiment, the serum albumin comprises mouse serum albumin or human serum albumin. In one embodiment, the immunoglobulin fragment comprises an immunoglobulin Fc domain.

In one embodiment, the RNA encoding an immunostimulant is administered in a formulation for targeting the lymphatic system.

In one embodiment, the RNA encoding an immunostimulant is administered in a formulation for targeting liver.

In one embodiment, the lymphatic system is secondary lymphoid organs, in particular spleen.

In one embodiment, the non-immunogenic RNA encoding a peptide or protein comprising an epitope and the RNA encoding an immunostimulant are administered in a common or separate formulation.

In one embodiment, the method is a method for treating or preventing cancer in a subject.

In one embodiment, the non-immunogenic RNA encoding a peptide or protein comprising an epitope and the RNA encoding an immunostimulant are transiently expressed in cells of the subject.

In one aspect, provided herein is a medical preparation comprising:

(i) non-immunogenic RNA encoding a peptide or protein comprising an epitope for inducing an immune response against an antigen in a subject; and (ii) an immunostimulant or RNA encoding an immunostimulant.

In one embodiment, the medical preparation is for treating a disease, disorder or condition associated with expression or elevated expression of an antigen.

In one embodiment, the immune response is a T cell-mediated immune response.

In one embodiment, the immune response comprises the generation of antigen-specific T cells.

In one embodiment, the antigen is a tumor-associated antigen.

In one embodiment, the disease, disorder or condition is cancer.

In one embodiment, the medical preparation comprises:

(i) the non-immunogenic RNA encoding a peptide or protein comprising an epitope; and (ii) RNA encoding an immunostimulant.

In one embodiment, the RNA encoding an immunostimulant is non-immunogenic.

In one embodiment, the non-immunogenic RNA when administered results in reduced activation of dendritic cells, activation of T cells and/or secretion of IFN-alpha compared to standard RNA.

In one embodiment, the non-immunogenic RNA is rendered non-immunogenic by the incorporation of modified nucleosides and the removal of dsRNA.

In one embodiment, the modified nucleosides suppress RNA-mediated activation of innate immune receptors.

In one embodiment, the modified nucleosides comprise a replacement of one or more uridines with a nucleoside comprising a modified nucleobase.

In one embodiment, the modified nucleobase is a modified uracil.

In one embodiment, the nucleoside comprising a modified nucleobase is selected from the group consisting of 3-methyl-uridine (m3U), 5-methoxy-uridine (mo5U), 5-aza-uridine, 6-aza-uridine, 2-thio-5-aza-uridine, 2-thio-uridine (s2U), 4-thio-uridine (s4U), 4-thio-pseudouridine, 2-thio-pseudouridine, 5-hydroxy-uridine (ho5U), 5-aminoallyl-uridine, 5-halo-uridine (e.g., 5-iodo-uridine or 5-bromo-uridine), uridine 5-oxyacetic acid (cmo5U), uridine 5-oxyacetic acid methyl ester (mcmo5U), 5-carboxymethyl-uridine (cm5U), 1-carboxymethyl-pseudouridine, 5-carboxyhydroxymethyl-uridine (chm5U), 5-carboxyhydroxymethyl-uridine methyl ester (mchm5U), 5-methoxycarbonylmethyl-uridine (mcm5U), 5-methoxycarbonylmethyl-2-thio-uridine (mcm5s2U), 5-aminomethyl-2-thio-uridine (nm5s2U), 5-methylaminomethyl-uridine (mnm5U), 1-ethyl-pseudouridine, 5-methylaminomethyl-2-thio-uridine (mnm5s2U), 5-methylaminomethyl-2-seleno-uridine (mnm5se2U), 5-carbamoylmethyl-uridine (ncm5U), 5-carboxymethylaminomethyl-uridine (cmnm5U), 5-carboxymethylaminomethyl-2-thio-uridine (cmnm5s2U), 5-propynyl-uridine, 1-propynyl-pseudouridine, 5-taurinomethyl-uridine (τm5U), 1-taurinomethyl-pseudouridine, 5-taurinomethyl-2-thio-uridine (τm5s2U), 1-taurinomethyl-4-thio-pseudouridine, 5-methyl-2-thio-uridine (m5s2U), 1-methyl-4-thio-pseudouridine (m1s4p), 4-thio-1-methyl-pseudouridine, 3-methyl-pseudouridine (m3ψ), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyl-dihydrouridine (m5D), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine, 3-(3-amino-3-carboxypropyl) uridine (acp3U), 1-methyl-3-(3-amino-3-carboxypropyl) pseudouridine (acp3 ψ), 5-(isopentenylaminomethyl)uridine (inm5U), 5-(isopentenylaminomethyl)-2-thio-uridine (inm5s2U), α-thio-uridine, 2'-O-methyl-uridine (Urn), 5,2'-O-dimethyl-uridine (m5Um), 2'-O-methyl-pseudouridine (ψm), 2-thio-2'-O-methyl-uridine (s2Um), 5-methoxycarbonylmethyl-2'-O-methyl-uridine (mcm5Um), 5-carbamoylmethyl-2'-O-methyl-uridine (ncm5Um), 5-carboxymethylaminomethyl-2'-O-methyl-uridine (cmnm5Um), 3,2'-O-dimethyl-uridine (m3Um), 5-(isopentenylaminomethyl)-2'-O-methyl-uridine (inm5Um), 1-thio-uridine, deoxythymidine, 2'-F-ara-uridine, 2'-F-uridine, 2'-OH-ara-uridine, 5-(2-carbomethoxyvinyl) uridine, and 5-[3-(1-E-propenylamino)uridine.

In one embodiment, the nucleoside comprising a modified nucleobase is pseudouridine (ψ), N1-methyl-pseudouridine (m1ψ) or 5-methyl-uridine (m5U).

In one embodiment, the nucleoside comprising a modified nucleobase is 1-methyl-pseudouridine.

In one embodiment, the non-immunogenic RNA encoding a peptide or protein comprising an epitope, and/or the RNA encoding an immunostimulant, is mRNA.

In one embodiment, the non-immunogenic RNA encoding a peptide or protein comprising an epitope, and/or the RNA encoding an immunostimulant, is in vitro transcribed RNA.

In one embodiment, the immunostimulant is a pro-inflammatory or anti-inflammatory immunostimulant.

In one embodiment, the non-immunogenic RNA encoding a peptide or protein comprising an epitope is present in a formulation for targeting the lymphatic system.

In one embodiment, the non-immunogenic RNA encoding a peptide or protein comprising an epitope is present in a formulation for targeting dendritic cells.

In one embodiment, the dendritic cells are immature dendritic cells.

In one embodiment, the immunostimulant comprises a cytokine or a variant thereof.

In one embodiment, the cytokine comprises a type I interferon or a variant thereof.

In one embodiment, the type I interferon comprises interferon-α or a variant thereof.

In one embodiment, the cytokine comprises an interleukin or a variant thereof.

In one embodiment, the cytokine supports T cell priming.

In one embodiment, the cytokine comprises IL12, IL15 or a variant thereof.

In one embodiment, the cytokine supports T cell proliferation and/or maintenance.

In one embodiment, the cytokine comprises IL2, IL7 or a variant thereof.

In one embodiment, the immunostimulant is extended pharmacokinetic (PK) immunostimulant. In one embodiment, the extended-PK immunostimulant comprises a fusion protein. In one embodiment, the fusion protein comprises a moiety of immunostimulant and a moiety selected from the group consisting of serum albumin, an immunoglobulin fragment, transferrin, Fn3, and variants thereof. In one embodiment, the serum albumin comprises mouse serum albumin or human serum albumin. In one embodiment, the immunoglobulin fragment comprises an immunoglobulin Fc domain.

In one embodiment, the RNA encoding an immunostimulant is present in a formulation for targeting the lymphatic system.

In one embodiment, the RNA encoding an immunostimulant is present in a formulation for targeting liver.

In one embodiment, the lymphatic system is secondary lymphoid organs, in particular spleen.

In one embodiment, the non-immunogenic RNA encoding a peptide or protein comprising an epitope and the RNA encoding an immunostimulant are present in a common or separate formulation.

In one embodiment, the medical preparation is a kit.

In one embodiment, the medical preparation comprises the non-immunogenic RNA encoding a peptide or protein comprising an epitope and the immunostimulant or the RNA encoding an immunostimulant in a pharmaceutical composition.

In one embodiment, the medical preparation comprises the non-immunogenic RNA encoding a peptide or protein comprising an epitope and the immunostimulant or the RNA encoding an immunostimulant in separate containers.

In one embodiment, the medical preparation further comprises instructions for using the medical preparation.

In one embodiment, the medical preparation is a pharmaceutical composition.

In one aspect, provided herein is the medical preparation described herein for pharmaceutical use.

In one embodiment, the pharmaceutical use comprises a therapeutic or prophylactic treatment of a disease or disorder.

In one embodiment, the disease or disorder is cancer.

In one aspect, provided herein is the medical preparation described herein for use in the method described herein.

C57BL/6 mice (n=3 per group) were vaccinated once i.v. with 10 μg stdRNA-LPX or modRNA-LPX not coding for an antigen (non-coding). Control mice received NaCl. (a) Expression of CD40, CD86, CCR7 and PD-L1 on splenic cDCs and pDCs and (b) CD69 on lymphoid cell subsets 24 h after vaccination. (c) Systemic release of IFNα 6 h after vaccination. Means of MFIs±SEM. One-way ANOVA and Dunnett's multiple comparisons test (a, b). ns: P>0.05, *: P≤0.05, : P≤0.01, *: P≤0.001, ****: P≤0.0001. modRNA, modified RNA. stdRNA, standard RNA. cDC, conventional dendritic cell. pDC, plasmaccytoid DC. NK, natural killer. MFI, median fluorescence intensity. <LLOD, below lower limit of detection.

Figure 2:
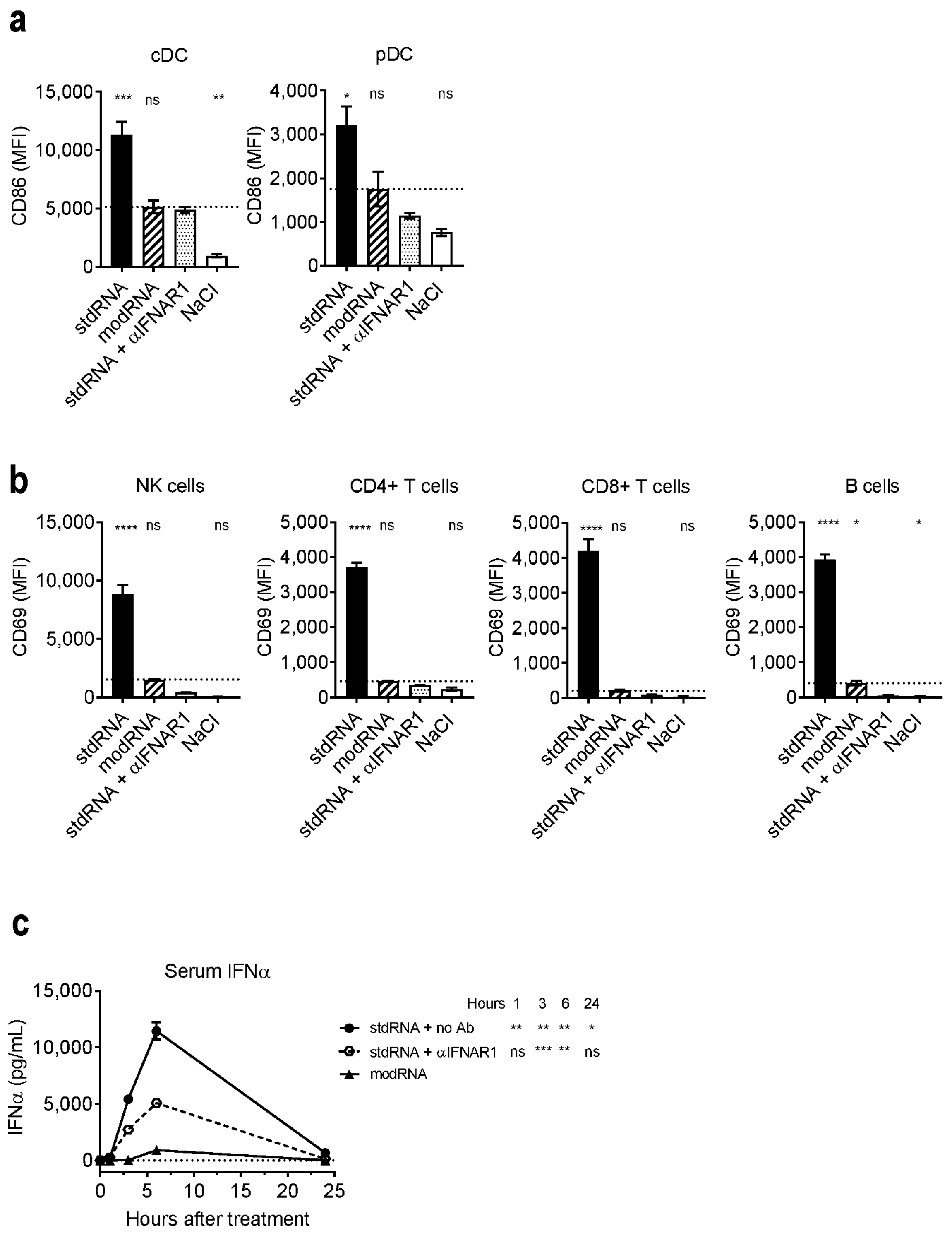

FIG. 2: Effects of modRNA can be mimicked by blocking IFNAR signaling.

C57BL/6 mice (n=3 per group) were vaccinated once i.v. with 40 μg stdRNA-LPX or modRNA-LPX coding for HPV16 E7, with and without 100 μg anti-IFNAR1 antibody treatment i.p. 5 h prior to vaccination. (a) CD86 expression on splenic cDCs and pDCs, and (b) CD69 on lymphoid cell subsets 24 h after vaccination. (c) Systemic IFNα release 1, 3, 6 and 24 h after vaccination. Control mice received NaCl.

Means of MFIs±SEM. One-way ANOVA and Dunnett's multiple comparisons test (a, b), two-way ANOVA and Dunnett's multiple comparisons test (c). ns: P>0.05, *: P≤0.05, : P≤0.01, *: P≤0.001, ****: P≤0.0001. modRNA, modified RNA. stdRNA, standard RNA. IFNAR1, IFNα receptor-1. αIFNAR1, anti-IFNAR1 antibody. cDC, conventional dendritic cell. pDC, plasmaccytoid DC. NK, natural killer. MFI, median fluorescence intensity.

Figure 3:
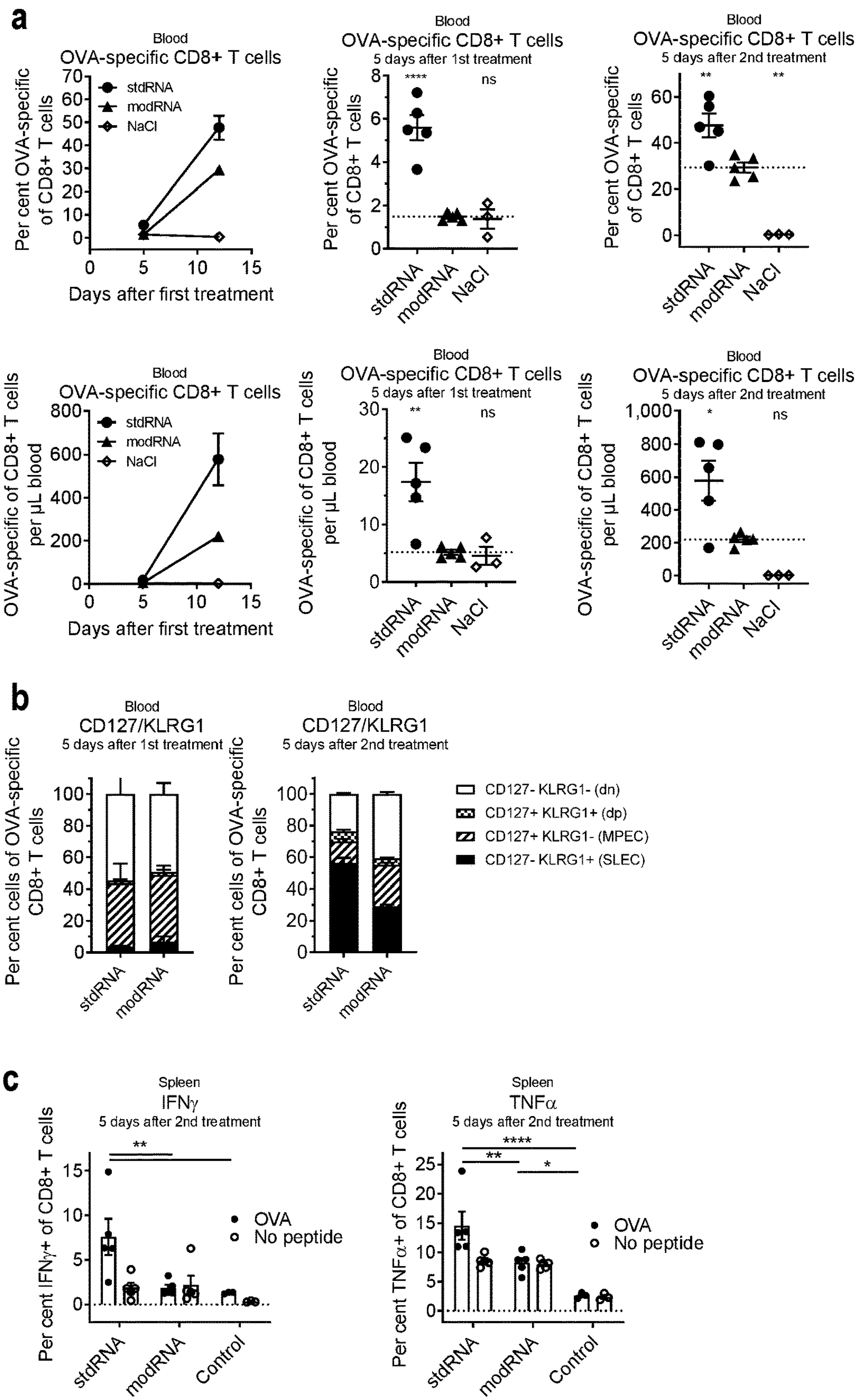

FIG. 3: modRNA restricts T cell proliferation and differentiation into functional effector cells.

C57BL/6 mice (n=3-5 per group) were vaccinated twice (day 0, 7) with 5 μg (a, b) or 20 μg (c) stdRNA-LPX or modRNA-LPX coding for OVA (OVA MHC class I and II (a, b), OVA MHC class I (c)), and antigen-specific CD8+ T cells were analyzed five days after each vaccination (day 5, 12). (a) Expansion of antigen-specific CD8+ T cells after each vaccination in peripheral blood (upper panels: fraction of CD8+ T cells; lower panels: absolute cell numbers). (b) Differentiation of antigen-specific CD8+ T cells after each vaccination characterized by CD127 and KLRG1 expression in peripheral blood. (c) Fraction of splenic CD8+ T cells expressing IFNγ and TNFα after ex vivo restimulation with cognate peptide after the second vaccination. Control mice received NaCl. Mean±SEM. One-way ANOVA and Dunnett's multiple comparisons test (a, c), two-way ANOVA and Tukey's multiple comparisons test (d). ns: P>0.05, *: P≤0.05, : P≤0.01, *: P≤0.001, ****: P≤0.0001. modRNA, modified RNA. stdRNA, standard RNA. OVA, ovalbumin. MPEC, memory precursor effector cells. SLEC, short-lived effector cells. dn, CD127/KLRG1 double-negative. dp, CD127/KLRG1 double-positive.

Figure 4:
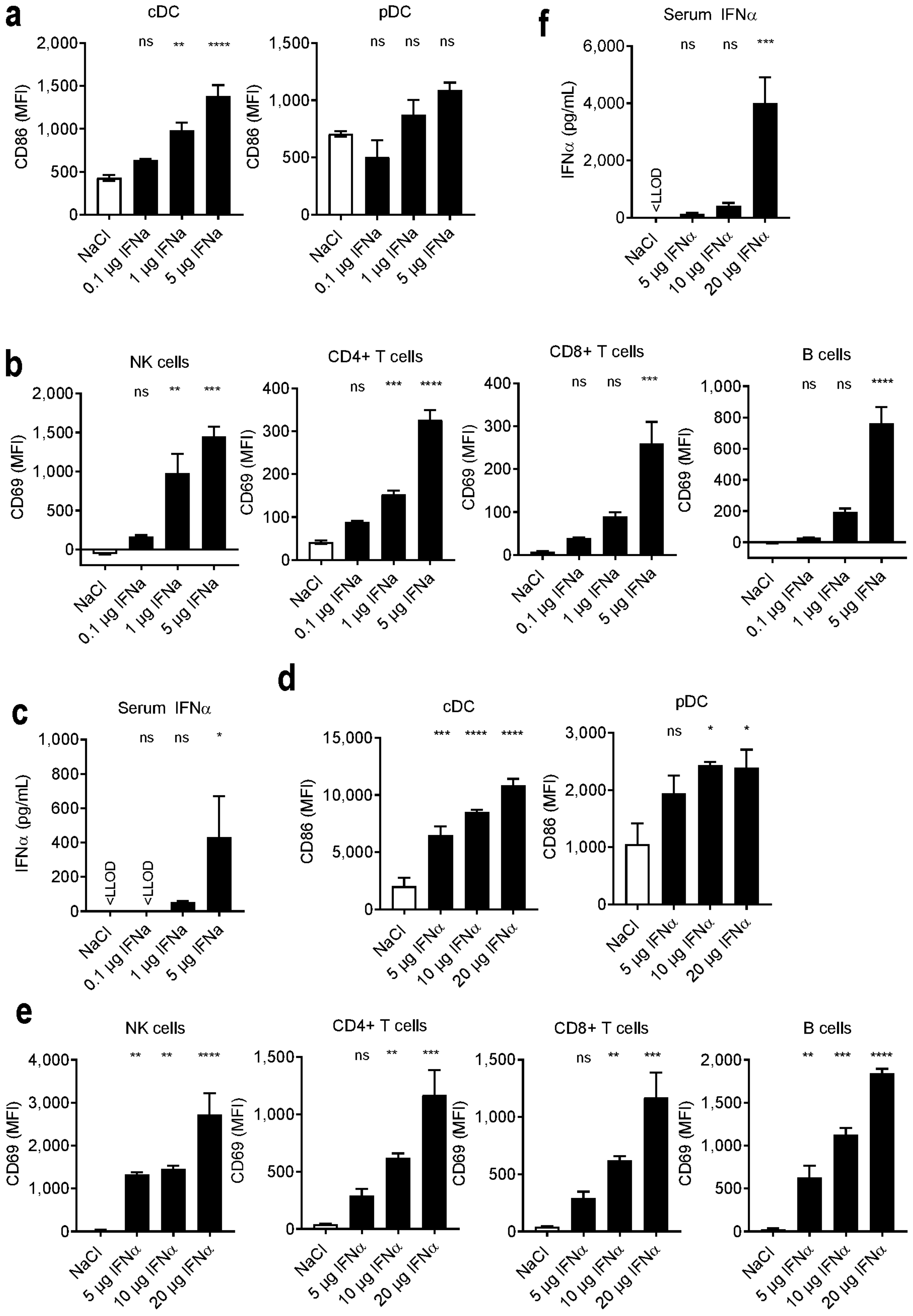

FIG. 4: Modified RNA-encoded IFNα activates APCs and lymphocytes.

C57BL/6 mice (n=3 per group) were treated once with IFNα RNA-LPX i.v. at low (0.1, 1, 5 μg, a-c) and high (5, 10, 20 μg, d-f) doses. (a, d) Expression of CD86 on splenic cDCs and pDCs and (b, e) CD69 on lymphoid cell subsets 24 h after treatment. (c, f) Systemic release of IFNα 6 h after treatment. Control mice received NaCl. Mean±SEM. One-way ANOVA and Dunnett's multiple comparisons test. ns: P>0.05, *: P≤0.05, : P≤0.01, *: P≤0.001, ****: P≤0.0001. modRNA, modified RNA. stdRNA, standard RNA. OVA, ovalbumin. APC, antigen-presenting cell. cDC, conventional dendritic cell. pDC, plasmaccytoid DC. NK, natural killer. MFI, median fluorescence intensity. <LLOD, below lower limit of detection.

Figure 5:
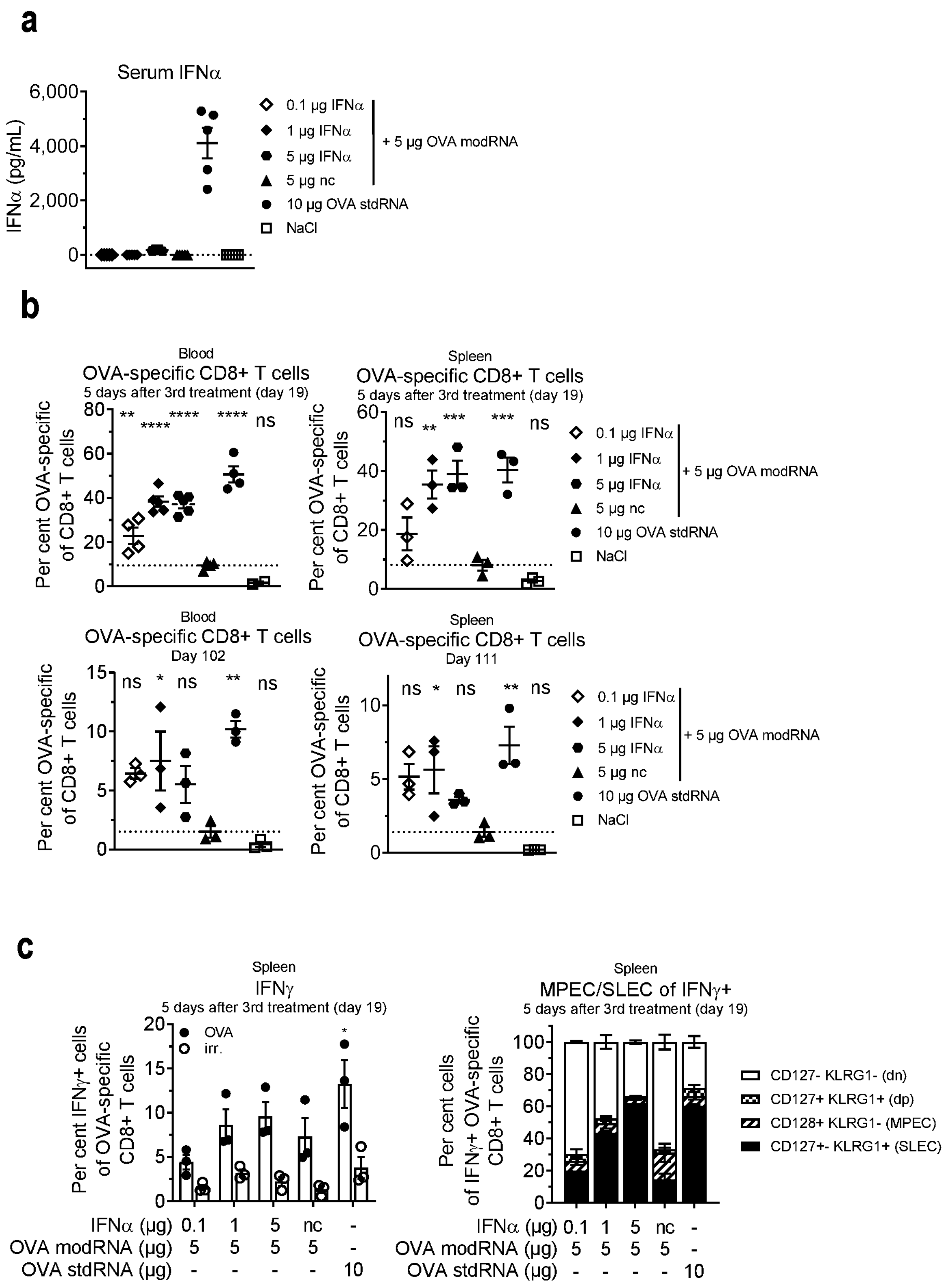
Figure 5:
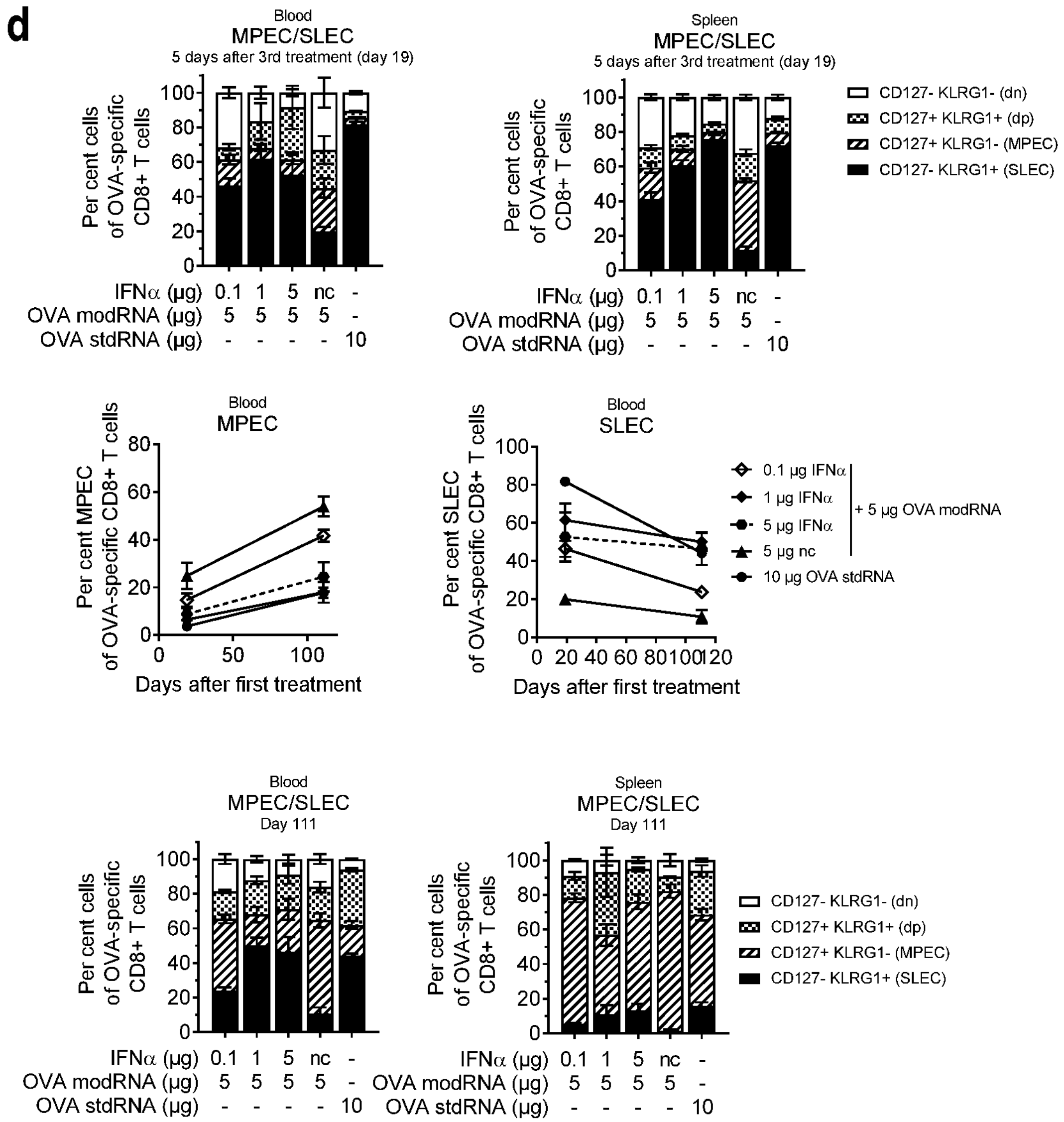

FIG. 5: Combination of modRNA with IFNα RNA restores proliferation, differentiation and function of T cells.

C57BL/6 mice (n=3-5 per group) were treated with 5 μg modRNA-LPX coding for OVA (OVA MHC class I and II) and 0.1, 1 or 5 μg IFNα RNA-LPX three times (day 0, 7, 14), and antigen-specific CD8+ T cells were analyzed five days after the third treatment (day 19; priming phase) and on day 102 and day 111 (memory phase) in the blood and in the spleen, respectively. Positive control mice were treated with 10 μg stdRNA-LPX coding for OVA (OVA MHC class I and II) only, negative control mice received 5 μg non-coding (nc) instead of IFNα-coding RNA-LPX together with modRNA-LPX coding for OVA, or NaCl only. (a) Systemic release of IFNα 6 h after the first treatment. (b) Expansion of antigen-specific CD8+ T cells on day 19 in peripheral blood (upper panels, left), in the spleen (upper panels, right), on day 102 in the blood (lower panels, left) and on day 111 in the spleen (lower panels, right). (c) Fraction of splenic antigen-specific CD8+ T cells expressing IFNγ after ex vivo restimulation with cognate peptide (left), and expression of IFNγ-producing subpopulations characterized by CD127 and KLRG1 expression (right) on day 19. (d) Antigen-specific CD8+ T cell differentiation characterized by CD127 and KLRG1 expression in the blood (upper panels, left) and in the spleen (upper panels, right) on day 19, change in MPEC (middle panels, left) and SLEC subset distribution (middle panels, right) during contraction, and change in all four subsets on day 111 in the blood (lower panels, left) and in the spleen (lower panels, right). Mean±SEM. One-way ANOVA and Dunnett's multiple comparisons test. ns: P>0.05, *: P≤0.05, : P≤0.01, *: P≤0.001, ****: P≤0.0001. modRNA, modified RNA. stdRNA, standard RNA. OVA, ovalbumin. nc, non-coding. MPEC, memory precursor effector cells. SLEC, short-lived effector cells. dn, CD127/KLRG1 double-negative. dp, CD127/KLRG1 double-positive.

DETAILED DESCRIPTION

Although the present disclosure is described in detail below, it is to be understood that this disclosure is not limited to the particular methodologies, protocols and reagents described herein as these may vary. It is also to be understood that the terminology used herein is for the purpose of describing particular embodiments only, and is not intended to limit the scope of the present disclosure which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

The practice of the present disclosure will employ, unless otherwise indicated, conventional methods of chemistry, biochemistry, cell biology, immunology, and recombinant DNA techniques which are explained in the literature in the field (cf., e.g., Molecular Cloning: A Laboratory Manual, 2nd Edition, J. Sambrook et al. eds., Cold Spring Harbor Laboratory Press, Cold Spring Harbor 1989).

In the following, the elements of the present disclosure will be described. These elements are listed with specific embodiments, however, it should be understood that they may be combined in any manner and in any number to create additional embodiments. The variously described examples and embodiments should not be construed to limit the present disclosure to only the explicitly described embodiments. This description should be understood to disclose and encompass embodiments which combine the explicitly described embodiments with any number of the disclosed elements. Furthermore, any permutations and combinations of all described elements should be considered disclosed by this description unless the context indicates otherwise.

The term "about" means approximately or nearly, and in the context of a numerical value or range set forth herein in one embodiment means ±20%, ±10%, ±5%, or ±3% of the numerical value or range recited or claimed.

The terms "a" and "an" and "the" and similar reference used in the context of describing the disclosure (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it was individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the disclosure and does not pose a limitation on the scope of the claims. No language in the specification should be construed as indicating any non-claimed element essential to the practice of the disclosure.

Unless expressly specified otherwise, the term "comprising" is used in the context of the present document to indicate that further members may optionally be present in addition to the members of the list introduced by "comprising". It is, however, contemplated as a specific embodiment of the present disclosure that the term "comprising" encompasses the possibility of no further members being present, i.e., for the purpose of this embodiment "comprising" is to be understood as having the meaning of "consisting of".

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the present disclosure was not entitled to antedate such disclosure.

In the following, definitions will be provided which apply to all aspects of the present disclosure. The following terms have the following meanings unless otherwise indicated. Any undefined terms have their art recognized meanings.

Definitions

Terms such as "reduce", "decrease", "inhibit" or "impair" as used herein relate to an overall decrease or the ability to cause an overall decrease, preferably of 5% or greater, 10% or greater, 20% or greater, more preferably of 50% or greater, and most preferably of 75% or greater, in the level, e.g. in the level of binding. Terms such as "increase", "enhance" or "exceed" preferably relate to an increase or enhancement by about at least 10%, preferably at least 20%, preferably at least 30%, more preferably at least 40%, more preferably at least 50%, even more preferably at least 80%, and most preferably at least 100%, at least 200%, at least 500%, or even more.

According to the disclosure, the term "peptide" comprises oligo- and polypeptides and refers to substances which comprise about two or more, about 3 or more, about 4 or more, about 6 or more, about 8 or more, about 10 or more, about 13 or more, about 16 or more, about 20 or more, and up to about 50, about 100 or about 150, consecutive amino acids linked to one another via peptide bonds. The term "protein" or "polypeptide" refers to large peptides, in particular peptides having at least about 150 amino acids, but the terms "peptide", "protein" and "polypeptide" are used herein usually as synonyms.

A "therapeutic protein" has a positive or advantageous effect on a condition or disease state of a subject when provided to the subject in a therapeutically effective amount. In one embodiment, a therapeutic protein has curative or palliative properties and may be administered to ameliorate, relieve, alleviate, reverse, delay onset of or lessen the severity of one or more symptoms of a disease or disorder. A therapeutic protein may have prophylactic properties and may be used to delay the onset of a disease or to lessen the severity of such disease or pathological condition. The term "therapeutic protein" includes entire proteins or peptides, and can also refer to therapeutically active fragments thereof. It can also include therapeutically active variants of a protein. Examples of therapeutically active proteins include, but are not limited to, immunostimulants such as cytokines, and antigens for vaccination.

"Fragment", with reference to an amino acid sequence (peptide or protein), relates to a part of an amino acid sequence, i.e. a sequence which represents the amino acid sequence shortened at the N-terminus and/or C-terminus. A fragment shortened at the C-terminus (N-terminal fragment) is obtainable e.g. by translation of a truncated open reading frame that lacks the 3'-end of the open reading frame. A fragment shortened at the N-terminus (C-terminal fragment) is obtainable e.g. by translation of a truncated open reading frame that lacks the 5'-end of the open reading frame, as long as the truncated open reading frame comprises a start codon that serves to initiate translation. A fragment of an amino acid sequence comprises e.g. at least 50%, at least 60%, at least 70%, at least 80%, at least 90% of the amino acid residues from an amino acid sequence. A fragment of an amino acid sequence preferably comprises at least 6, in particular at least 8, at least 12, at least 15, at least 20, at least 30, at least 50, or at least 100 consecutive amino acids from an amino acid sequence.

By "variant" or "variant protein" or "variant polypeptide" herein is meant a protein that differs from a wild type protein by virtue of at least one amino acid modification. The parent polypeptide may be a naturally occurring or wild type (WT) polypeptide, or may be a modified version of a wild type polypeptide. Preferably, the variant polypeptide has at least one amino acid modification compared to the parent polypeptide, e.g. from 1 to about 20 amino acid modifications, and preferably from 1 to about 10 or from 1 to about 5 amino acid modifications compared to the parent.

By "parent polypeptide", "parent protein", "precursor polypeptide", or "precursor protein" as used herein is meant an unmodified polypeptide that is subsequently modified to generate a variant. A parent polypeptide may be a wild type polypeptide, or a variant or engineered version of a wild type polypeptide.

By "wild type" or "WT" or "native" herein is meant an amino acid sequence that is found in nature, including allelic variations. A wild type protein or polypeptide has an amino acid sequence that has not been intentionally modified.

For the purposes of the present disclosure, "variants" of an amino acid sequence (peptide, protein or polypeptide) comprise amino acid insertion variants, amino acid addition variants, amino acid deletion variants and/or amino acid substitution variants. The term "variant" includes all splice variants, posttranslationally modified variants, conformations, isoforms and species homologs, in particular those which are naturally expressed by cells. The term "variant" includes, in particular, fragments of an amino acid sequence.

Amino acid insertion variants comprise insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible. Amino acid addition variants comprise amino- and/or carboxy-terminal fusions of one or more amino acids, such as 1, 2, 3, 5, 10, 20, 30, 50, or more amino acids. Amino acid deletion variants are characterized by the removal of one or more amino acids from the sequence, such as by removal of 1, 2, 3, 5, 10, 20, 30, 50, or more amino acids. The deletions may be in any position of the protein. Amino acid deletion variants that comprise the deletion at the N-terminal and/or C-terminal end of the protein are also called N-terminal and/or C-terminal truncation variants. Amino acid substitution variants are characterized by at least one residue in the sequence being removed and another residue being inserted in its place. Preference is given to the modifications being in positions in the amino acid sequence which are not conserved between homologous proteins or peptides and/or to replacing amino acids with other ones having similar properties. Preferably, amino acid changes in peptide and protein variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids. In one embodiment, conservative amino acid substitutions include substitutions within the following groups:

glycine, alanine;
valine, isoleucine, leucine;
aspartic acid, glutamic acid;
asparagine, glutamine;
serine, threonine;
lysine, arginine; and
phenylalanine, tyrosine.

Preferably the degree of similarity, preferably identity between a given amino acid sequence and an amino acid sequence which is a variant of said given amino acid sequence will be at least about 60%, 70%, 80%, 81%, 82%, 83%, 84%, 85%, 86%, 87%, 88%, 89%, 90%, 91%, 92%, 93%, 94%, 95%, 96%, 97%, 98%, or 99%. The degree of similarity or identity is given preferably for an amino acid region which is at least about 10%, at least about 20%, at least about 30%, at least about 40%, at least about 50%, at least about 60%, at least about 70%, at least about 80%, at least about 90% or about 100% of the entire length of the reference amino acid sequence. For example, if the reference amino acid sequence consists of 200 amino acids, the degree of similarity or identity is given preferably for at least about 20, at least about 40, at least about 60, at least about 80, at least about 100, at least about 120, at least about 140, at least about 160, at least about 180, or about 200 amino acids, preferably continuous amino acids. In preferred embodiments, the degree of similarity or identity is given for the entire length of the reference amino acid sequence. The alignment for determining sequence similarity, preferably sequence identity can be done with art known tools, preferably using the best sequence alignment, for example, using Align, using standard settings, preferably EMBOSS::needle, Matrix: Blosum62, Gap Open 10.0, Gap Extend 0.5.

"Sequence similarity" indicates the percentage of amino acids that either are identical or that represent conservative amino acid substitutions. "Sequence identity" between two amino acid sequences indicates the percentage of amino acids that are identical between the sequences.

The term "percentage identity" is intended to denote a percentage of amino acid residues which are identical between the two sequences to be compared, obtained after the best alignment, this percentage being purely statistical and the differences between the two sequences being distributed randomly and over their entire length. Sequence comparisons between two amino acid sequences are conventionally carried out by comparing these sequences after having aligned them optimally, said comparison being carried out by segment or by "window of comparison" in order to identify and compare local regions of sequence similarity. The optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

The percentage identity is calculated by determining the number of identical positions between the two sequences being compared, dividing this number by the number of positions compared and multiplying the result obtained by 100 so as to obtain the percentage identity between these two sequences.

Homologous amino acid sequences exhibit according to the disclosure at least 40%, in particular at least 50%, at least 60%, at least 70%, at least 80%, at least 90% and preferably at least 95%, at least 98 or at least 99% identity of the amino acid residues.

The amino acid sequence variants described herein may readily be prepared by the skilled person, for example, by recombinant DNA manipulation. The manipulation of DNA sequences for preparing peptides or proteins having substitutions, additions, insertions or deletions, is described in detail in Sambrook et al. (1989), for example. Furthermore, the peptides and amino acid variants described herein may be readily prepared with the aid of known peptide synthesis techniques such as, for example, by solid phase synthesis and similar methods.

In one embodiment, a fragment or variant of an amino acid sequence (peptide or protein) is preferably a "functional fragment" or "functional variant". The term "functional fragment" or "functional variant" of an amino acid sequence relates to any fragment or variant exhibiting one or more functional properties identical or similar to those of the amino acid sequence from which it is derived, i.e., it is functionally equivalent. With respect to immunostimulants such as cytokines, one particular function is one or more immunostimulatory activities displayed by the amino acid sequence from which the fragment or variant is derived and/or binding to the receptor(s) the amino acid sequence from which the fragment or variant is derived binds to. The term "functional fragment" or "functional variant", as used herein, in particular refers to a variant molecule or sequence that comprises an amino acid sequence that is altered by one or more amino acids compared to the amino acid sequence of the parent molecule or sequence and that is still capable of fulfilling one or more of the functions of the parent molecule or sequence, e.g., binding to a target molecule or contributing to binding to a target molecule. In one embodiment, the modifications in the amino acid sequence of the parent molecule or sequence do not significantly affect or alter the binding characteristics of the molecule or sequence. In different embodiments, binding of the functional fragment or functional variant may be reduced but still significantly present, e.g., binding of the functional variant may be at least 50%, at least 60%, at least 70%, at least 80%, or at least 90% of the parent molecule or sequence. However, in other embodiments, binding of the functional fragment or functional variant may be enhanced compared to the parent molecule or sequence.

An amino acid sequence (peptide, protein or polypeptide) "derived from" a designated amino acid sequence (peptide, protein or polypeptide) refers to the origin of the first amino acid sequence. Preferably, the amino acid sequence which is derived from a particular amino acid sequence has an amino acid sequence that is identical, essentially identical or homologous to that particular sequence or a fragment thereof. Amino acid sequences derived from a particular amino acid sequence may be variants of that particular sequence or a fragment thereof. For example, it will be understood by one of ordinary skill in the art that the antigens and immunostimulants suitable for use herein may be altered such that they vary in sequence from the naturally occurring or native sequences from which they were derived, while retaining the desirable activity of the native sequences.

As used herein, an "instructional material" or "instructions" includes a publication, a recording, a diagram, or any other medium of expression which can be used to communicate the usefulness of the compositions and methods of the invention. The instructional material of the kit of the invention may, for example, be affixed to a container which contains the compositions of the invention or be shipped together with a container which contains the compositions. Alternatively, the instructional material may be shipped separately from the container with the intention that the instructional material and the compositions be used cooperatively by the recipient.

"Isolated" means altered or removed from the natural state. For example, a nucleic acid or a peptide naturally present in a living animal is not "isolated", but the same nucleic acid or peptide partially or completely separated from the coexisting materials of its natural state is "isolated". An isolated nucleic acid or protein can exist in substantially purified form, or can exist in a non-native environment such as, for example, a host cell.

The term "recombinant" in the context of the present invention means "made through genetic engineering". Preferably, a "recombinant object" such as a recombinant cell in the context of the present invention is not occurring naturally.

The term "naturally occurring" as used herein refers to the fact that an object can be found in nature. For example, a peptide or nucleic acid that is present in an organism (including viruses) and can be isolated from a source in nature and which has not been intentionally modified by man in the laboratory is naturally occurring.

The term "genetic modification" or simply "modification" includes the transfection of cells with nucleic acid. The term "transfection" relates to the introduction of nucleic acids, in particular RNA, into a cell. For purposes of the present invention, the term "transfection" also includes the introduction of a nucleic acid into a cell or the uptake of a nucleic acid by such cell, wherein the cell may be present in a subject, e.g., a patient. Thus, according to the present invention, a cell for transfection of a nucleic acid described herein can be present in vitro or in vivo, e.g. the cell can form part of an organ, a tissue and/or an organism of a patient. According to the invention, transfection can be transient or stable. For some applications of transfection, it is sufficient if the transfected genetic material is only transiently expressed. RNA can be transfected into cells to transiently express its coded protein. Since the nucleic acid introduced in the transfection process is usually not integrated into the nuclear genome, the foreign nucleic acid will be diluted through mitosis or degraded. Cells allowing episomal amplification of nucleic acids greatly reduce the rate of dilution. If it is desired that the transfected nucleic acid actually remains in the genome of the cell and its daughter cells, a stable transfection must occur. Such stable transfection can be achieved by using virus-based systems or transposon-based systems for transfection. Generally, cells that are genetically modified to express an antigen receptor are stably transfected with nucleic acid encoding the receptor, while, generally, nucleic acid encoding an immunostimulant and/or nucleic acid encoding antigen is transiently transfected into cells. RNA can be transfected into cells to transiently express its coded protein.

Nucleic Acids

The term "polynucleotide" or "nucleic acid", as used herein, is intended to include DNA and RNA such as genomic DNA, cDNA, mRNA, recombinantly produced and chemically synthesized molecules. A nucleic acid may be single-stranded or double-stranded. RNA includes in vitro transcribed RNA (IVT RNA) or synthetic RNA. According to the invention, a polynucleotide is preferably isolated.

Nucleic acids may be comprised in a vector. The term "vector" as used herein includes any vectors known to the skilled person including plasmid vectors, cosmid vectors, phage vectors such as lambda phage, viral vectors such as retroviral, adenoviral or baculoviral vectors, or artificial chromosome vectors such as bacterial artificial chromosomes (BAC), yeast artificial chromosomes (YAC), or P1 artificial chromosomes (PAC). Said vectors include expression as well as cloning vectors. Expression vectors comprise plasmids as well as viral vectors and generally contain a desired coding sequence and appropriate DNA sequences necessary for the expression of the operably linked coding sequence in a particular host organism (e.g., bacteria, yeast, plant, insect, or mammal) or in in vitro expression systems. Cloning vectors are generally used to engineer and amplify a certain desired DNA fragment and may lack functional sequences needed for expression of the desired DNA fragments.

In one embodiment of all aspects of the invention, nucleic acid such as nucleic acid encoding a vaccine antigen, nucleic acid encoding an immunostimulant, or nucleic acid encoding an antigen receptor is expressed in cells of the subject treated to provide the vaccine antigen, immunostimulant, or antigen receptor. In one embodiment of all aspects of the invention, the nucleic acid is transiently expressed in cells of the subject. Thus, in one embodiment, the nucleic acid is not integrated into the genome of the cells. In one embodiment of all aspects of the invention, the nucleic acid is RNA, preferably in vitro transcribed RNA. In one embodiment of all aspects of the invention, expression of the vaccine antigen is at the cell surface. In one embodiment of all aspects of the invention, the vaccine antigen is expressed and presented in the context of MHC. In one embodiment of all aspects of the invention, expression of the immunostimulant is into the extracellular space, i.e., the immunostimulant is secreted. In one embodiment of all aspects of the invention, expression of the antigen receptor is at the cell surface.

In one embodiment of all aspects of the invention, the nucleic acid encoding the vaccine antigen is expressed in cells such as antigen presenting cells of the subject treated to provide the vaccine antigen for binding by immune effector cells, said binding resulting in stimulation, priming and/or expansion of the immune effector cells.

The nucleic acids described herein may be recombinant and/or isolated molecules.

In the present disclosure, the term "RNA" relates to a nucleic acid molecule which includes ribonucleotide residues. In preferred embodiments, the RNA contains all or a majority of ribonucleotide residues. As used herein, "ribonucleotide" refers to a nucleotide with a hydroxyl group at the 2'-position of a β-D-ribofuranosyl group. RNA encompasses without limitation, double stranded RNA, single stranded RNA, isolated RNA such as partially purified RNA, essentially pure RNA, synthetic RNA, recombinantly produced RNA, as well as modified RNA that differs from naturally occurring RNA by the addition, deletion, substitution and/or alteration of one or more nucleotides. Such alterations may refer to addition of non-nucleotide material to internal RNA nucleotides or to the end(s) of RNA. It is also contemplated herein that nucleotides in RNA may be non-standard nucleotides, such as chemically synthesized nucleotides or deoxynucleotides. For the present disclosure, these altered RNAs are considered analogs of naturally-occurring RNA.

In certain embodiments of the present disclosure, the RNA is messenger RNA (mRNA) that relates to a RNA transcript which encodes a peptide or protein. As established in the art, mRNA generally contains a 5' untranslated region (5'-UTR), a peptide coding region and a 3' untranslated region (3'-UTR). In some embodiments, the RNA is produced by in vitro transcription or chemical synthesis. In one embodiment, the mRNA is produced by in vitro transcription using a DNA template where DNA refers to a nucleic acid that contains deoxyribonucleotides.

In one embodiment, RNA is in vitro transcribed RNA (IVT-RNA) and may be obtained by in vitro transcription of an appropriate DNA template. The promoter for controlling transcription can be any promoter for any RNA polymerase. A DNA template for in vitro transcription may be obtained by cloning of a nucleic acid, in particular cDNA, and introducing it into an appropriate vector for in vitro transcription. The cDNA may be obtained by reverse transcription of RNA.

In one embodiment, the RNA described herein may have modified nucleosides. In some embodiments, the RNA comprises a modified nucleoside in place of at least one (e.g., every) uridine.

The term "uracil," as used herein, describes one of the nucleobases that can occur in the nucleic acid of RNA. The structure of uracil is:

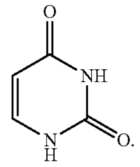

The term "uridine," as used herein, describes one of the nucleosides that can occur in RNA. The structure of uridine is:

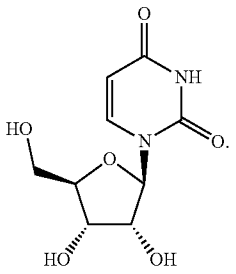 [SMILES: O=c1ccn([C@@H]2O[C@H](CO)[C@@H](O)[C@H]2O)c(=O)[nH]1]

UTP (uridine 5'-triphosphate) has the following structure:

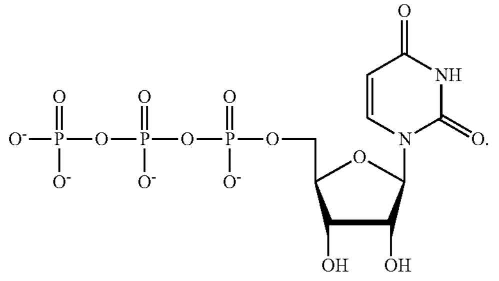

Pseudo-UTP (pseudouridine 5'-triphosphate) has the following structure:

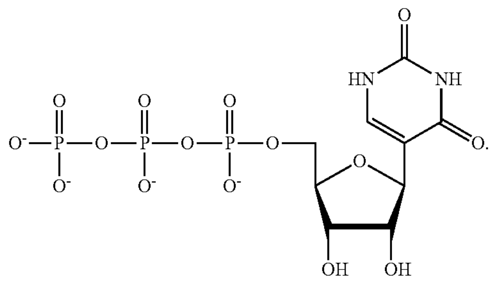

"Pseudouridine" is one example of a modified nucleoside that is an isomer of uridine, where the uracil is attached to the pentose ring via a carbon-carbon bond instead of a nitrogen-carbon glycosidic bond.

Another exemplary modified nucleoside is N1-methyl-pseudouridine (m1ψ), which has the structure:

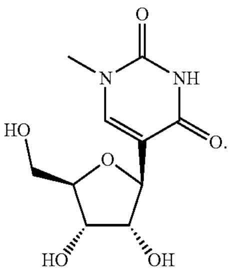 [SMILES: Cn1cc([C@@H]2O[C@H](CO)[C@@H](O)[C@H]2O)c(=O)[nH]c1=O]

N1-methyl-pseudo-UTP has the following structure:

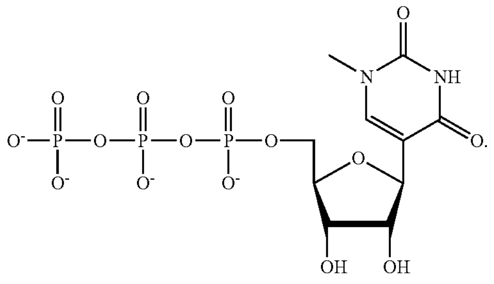

Another exemplary modified nucleoside is 5-methyl-uridine (m5U), which has the structure:

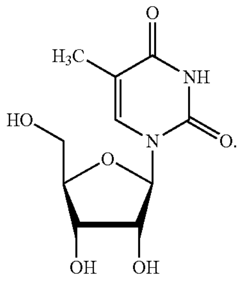

In some embodiments, one or more uridine in the RNA described herein is replaced by a modified nucleoside. In some embodiments, the modified nucleoside is a modified uridine.

In some embodiments, RNA comprises a modified nucleoside in place of at least one uridine. In some embodiments, RNA comprises a modified nucleoside in place of each uridine.

In some embodiments, the modified nucleoside is independently selected from pseudouridine (ψ), N1-methyl-pseudouridine (m1ψ), and 5-methyl-uridine (m5U). In some embodiments, the modified nucleoside comprises pseudouridine (ψ). In some embodiments, the modified nucleoside comprises N1 methyl-pseudouridine (m1ψ). In some embodiments, the modified nucleoside comprises 5-methyl-uridine (m5U). In some embodiments, RNA may comprise more than one type of modified nucleoside, and the modified nucleosides are independently selected from pseudouridine (ψ), N1-methyl-pseudouridine (m1ψ), and 5-methyl-uridine (m5U). In some embodiments, the modified nucleosides comprise pseudouridine (ψ) and N1-methyl-pseudouridine (m1ψ). In some embodiments, the modified nucleosides comprise pseudouridine (ψ) and 5-methyl-uridine (m5U). In some embodiments, the modified nucleosides comprise N1-methyl-pseudouridine (m1ψ) and 5-methyl-uridine (m5U). In some embodiments, the modified nucleosides comprise pseudouridine (ψ), N1-methyl-pseudouridine (m1ψ), and 5-methyl-uridine (m5U).

In some embodiments, the modified nucleoside replacing one or more uridine in the RNA may be any one or more of 3-methyl-uridine (m$^{3}$U), 5-methoxy-uridine (mo$^{5}$U), 5-aza-uridine, 6-aza-uridine, 2-thio-5-aza-uridine, 2-thio-uridine (s$^{2}$U), 4-thio-uridine (s$^{4}$U), 4-thio-pseudouridine, 2-thio-pseudouridine, 5-hydroxy-uridine (ho$^{5}$U), 5-aminoallyl-uridine, 5-halo-uridine (e.g., 5-iodo-uridine or 5-bromo-uridine), uridine 5-oxyacetic acid (cmo$^{5}$U), uridine 5-oxyacetic acid methyl ester (mcmo$^{5}$U), 5-carboxymethyl-uridine (cm$^{5}$U), 1-carboxymethyl-pseudouridine, 5-carboxyhydroxymethyl-uridine (chm$^{5}$U), 5-carboxyhydroxymethyl-uridine methyl ester (mchm$^{5}$U), 5-methoxycarbonylmethyl-uridine (mcm$^{5}$U), 5-methoxycarbonylmethyl-2-thio-uridine (mcm$^5$s$^2$U), 5-aminomethyl-2-thio-uridine (nm$^5$s$^2$U), 5-methylaminomethyl-uridine (mnm$^5$U), 1-ethyl-pseudouridine, 5-methylaminomethyl-2-thio-uridine (mnm$^5$s$^2$U), 5-methylaminomethyl-2-seleno-uridine (mnm$^5$se$^2$U), 5-carbamoylmethyl-uridine (ncm$^5$U), 5-carboxymethylaminomethyl-uridine (cmnm$^5$U), 5-carboxymethylaminomethyl-2-thio-uridine (cmnm$^5$s$^2$U), 5-propynyl-uridine, 1-propynyl-pseudouridine, 5-taurinomethyl-uridine ($\tau$m$^5$U), 1-taurinomethyl-pseudouridine, 5-taurinomethyl-2-thio-uridine ($\tau$m5s2U), 1-taurinomethyl-4-thio-pseudouridine), 5-methyl-2-thio-uridine (m$^5$s$^2$U), 1-methyl-4-thio-pseudouridine (m$^1$s$^4\psi$), 4-thio-1-methyl-pseudouridine, 3-methyl-pseudouridine (m$^3\psi$), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyl-dihydrouridine (m$^5$D), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine, 3-(3-amino-3-carboxypropyl)uridine (acp$^3$U), 1 methyl-3-(3-amino-3-carboxypropyl)pseudouridine (acp$^3\psi$), 5-(isopentenylaminomethyl)uridine (inm$^5$U), 5-(isopentenylaminomethyl)-2-thio-uridine (inm$^5$s$^2$U), $\alpha$-thio-uridine, 2'-O-methyl-uridine (Um), 5,2'-O-dimethyl-uridine (m$^5$Um), 2'-O-methyl-pseudouridine ($\psi$m), 2-thio-2'-O-methyl-uridine (s$^2$Um), 5-methoxycarbonylmethyl-2'-O-methyl-uridine (mcm$^5$Um), 5-carbamoylmethyl-2'-O-methyl-uridine (ncm$^5$Um), 5-carboxymethylaminomethyl-2'-O-methyl-uridine (cmnm$^5$Um), 3,2'-O-dimethyl-uridine (m$^3$Um), 5-(isopentenylaminomethyl)-2'-O-methyl-uridine (inm$^5$Um), 1-thio-uridine, deoxythymidine, 2'-F-ara-uridine, 2'-F-uridine, 2'-OH-ara-uridine, 5-(2-carbomethoxyvinyl) uridine, 5-[3-(1-E-propenylamino)uridine, or any other modified uridine known in the art.

In some embodiments, the RNA according to the present disclosure comprises a 5'-cap. In one embodiment, the RNA of the present disclosure does not have uncapped 5'-triphosphates. In one embodiment, the RNA may be modified by a 5'-cap analog. The term "5'-cap" refers to a structure found on the 5'-end of an mRNA molecule and generally consists of a guanosine nucleotide connected to the mRNA via a 5'- to 5'-triphosphate linkage. In one embodiment, this guanosine is methylated at the 7-position. Providing an RNA with a 5'-cap or 5'-cap analog may be achieved by in vitro transcription, in which the 5'-cap is co-transcriptionally expressed into the RNA strand, or may be attached to RNA post-transcriptionally using capping enzymes.

In some embodiments, the building block cap for RNA is m$_2^{7,3'-O}$Gppp(m1$^{2'-O}$)ApG (also sometimes referred to as m$_2^{7,3'O}$G(5')ppp(5')m$^{2'-O}$ApG), which has the following structure:

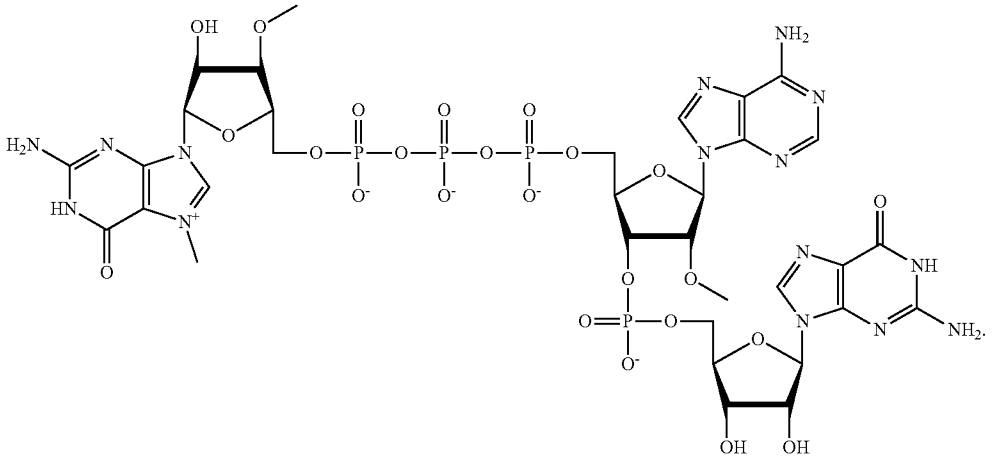

Below is an exemplary Cap1 RNA, which comprises RNA and m$_2^{7,3'O}$G(5')ppp(5')m$^{2'-O}$ApG:

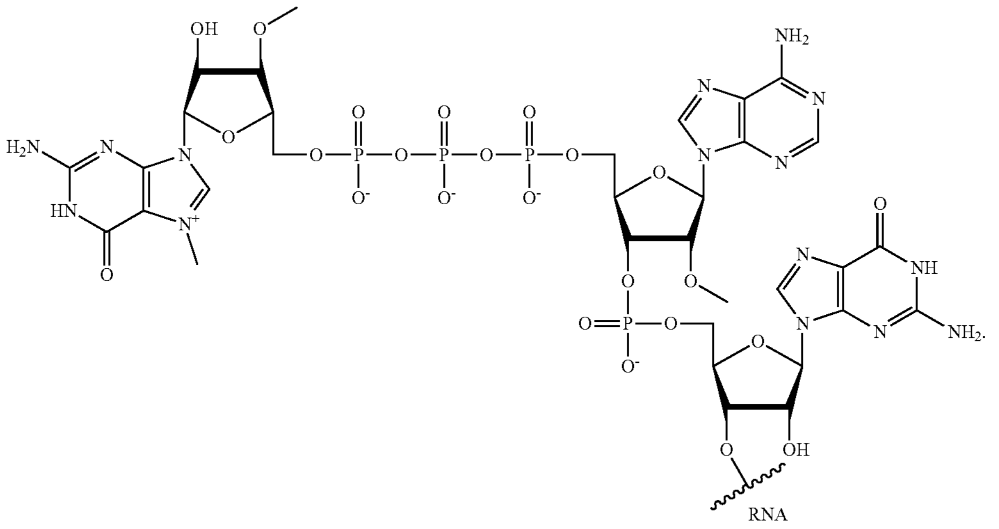

Below is another exemplary Cap1 RNA (no cap analog):

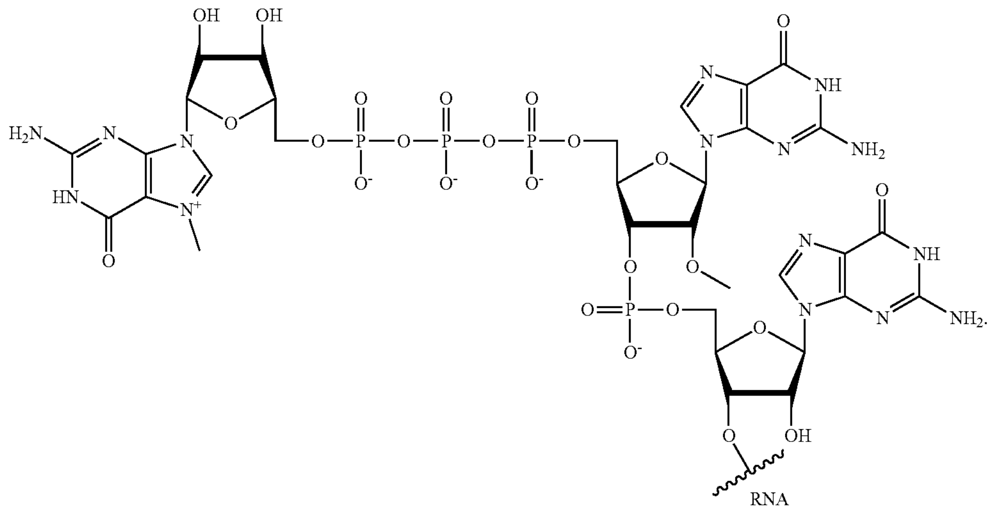

In some embodiments, the RNA is modified with "Cap0" structures using, in one embodiment, the cap analog anti-reverse cap (ARCA Cap ($m_2^{7,3'O}$G(5')ppp(5')G)) with the structure:

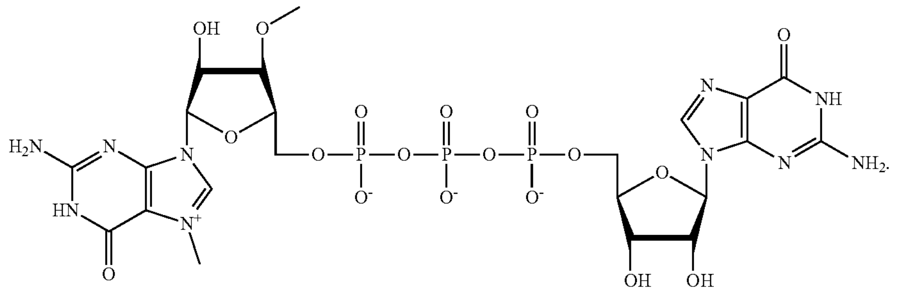

Below is an exemplary Cap0 RNA comprising RNA and $m_2^{7,3'O}$G(5')ppp(5')G:

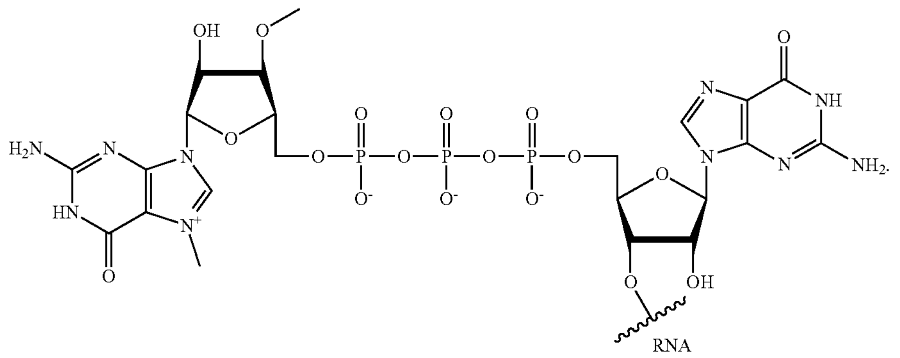

In some embodiments, the "Cap0" structures are generated using the cap analog Beta-S-ARCA ($m_2^{7,2'O}$G(5')ppSp(5')G) with the structure:

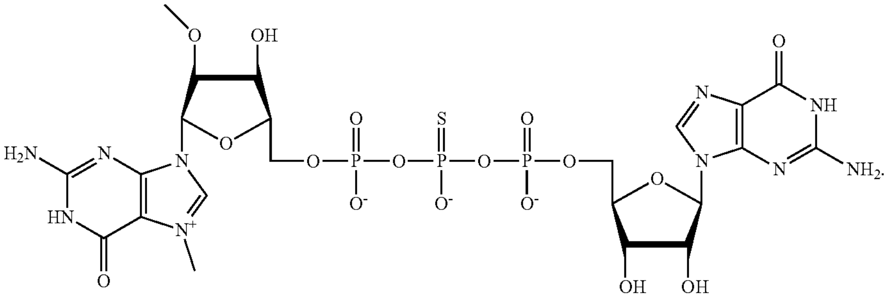

Below is an exemplary Cap0 RNA comprising Beta-S-ARCA ($m_2^{7,2'O}$G(5')ppSp(5')G) and RNA:

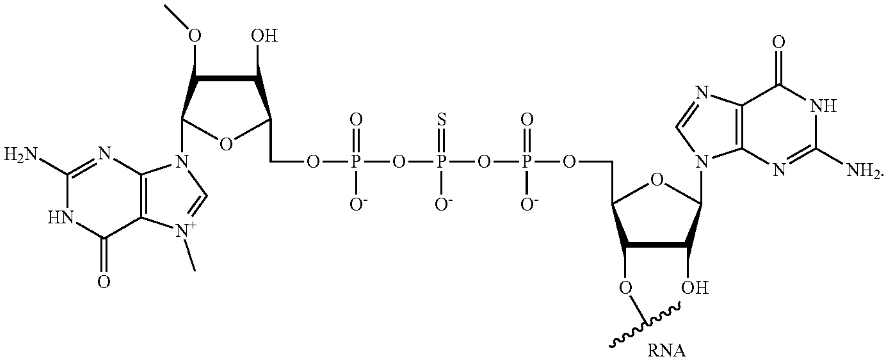

In some embodiments, RNA according to the present disclosure comprises a 5'-UTR and/or a 3'-UTR. The term "untranslated region" or "UTR" relates to a region in a DNA molecule which is transcribed but is not translated into an amino acid sequence, or to the corresponding region in an RNA molecule, such as an mRNA molecule. An untranslated region (UTR) can be present 5' (upstream) of an open reading frame (5'-UTR) and/or 3' (downstream) of an open reading frame (3'-UTR). A 5'-UTR, if present, is located at the 5' end, upstream of the start codon of a protein-encoding region. A 5'-UTR is downstream of the 5'-cap (if present), e.g. directly adjacent to the 5'-cap. A 3'-UTR, if present, is located at the 3' end, downstream of the termination codon of a protein-encoding region, but the term "3'-UTR" does preferably not include the poly(A) sequence. Thus, the 3'-UTR is upstream of the poly(A) sequence (if present), e.g. directly adjacent to the poly(A) sequence.

In some embodiments, the RNA according to the present disclosure comprises a 3'-poly(A) sequence. As used herein, the term "poly(A) sequence" or "poly-A tail" refers to an uninterrupted or interrupted sequence of adenylate residues which is typically located at the 3'-end of an RNA molecule. Poly(A) sequences are known to those of skill in the art and may follow the 3'-UTR in the RNAs described herein. An uninterrupted poly(A) sequence is characterized by consecutive adenylate residues. In nature, an uninterrupted poly(A) sequence is typical. RNAs disclosed herein can have a poly(A) sequence attached to the free 3'-end of the RNA by a template-independent RNA polymerase after transcription or a poly(A) sequence encoded by DNA and transcribed by a template-dependent RNA polymerase.

It has been demonstrated that a poly(A) sequence of about 120 A nucleotides has a beneficial influence on the levels of RNA in transfected eukaryotic cells, as well as on the levels of protein that is translated from an open reading frame that is present upstream (5') of the poly(A) sequence (Holtkamp et al., 2006, Blood, vol. 108, pp. 4009-4017).

The poly(A) sequence may be of any length. In some embodiments, a poly(A) sequence comprises, essentially consists of, or consists of at least 20, at least 30, at least 40, at least 80, or at least 100 and up to 500, up to 400, up to 300, up to 200, or up to 150 A nucleotides, and, in particular, about 120 A nucleotides. In this context, "essentially consists of" means that most nucleotides in the poly(A) sequence, typically at least 75%, at least 80%, at least 85%, at least 90%, at least 95%, at least 96%, at least 97%, at least 98%, or at least 99% by number of nucleotides in the poly(A) sequence are A nucleotides, but permits that remaining nucleotides are nucleotides other than A nucleotides, such as U nucleotides (uridylate), G nucleotides (guanylate), or C nucleotides (cytidylate). In this context, "consists of" means that all nucleotides in the poly(A) sequence, i.e., 100% by number of nucleotides in the poly(A) sequence, are A nucleotides. The term "A nucleotide" or "A" refers to adenylate.

In some embodiments, a poly(A) sequence is attached during RNA transcription, e.g., during preparation of in vitro transcribed RNA, based on a DNA template comprising repeated dT nucleotides (deoxythymidylate) in the strand complementary to the coding strand. The DNA sequence encoding a poly(A) sequence (coding strand) is referred to as poly(A) cassette.

In some embodiments, the poly(A) cassette present in the coding strand of DNA essentially consists of dA nucleotides, but is interrupted by a random sequence of the four nucleotides (dA, dC, dG, and dT). Such random sequence may be 5 to 50, 10 to 30, or 10 to 20 nucleotides in length. Such a cassette is disclosed in WO 2016/005324 A1, hereby incorporated by reference. Any poly(A) cassette disclosed in WO 2016/005324 A1 may be used in the present invention. A poly(A) cassette that essentially consists of dA nucleotides, but is interrupted by a random sequence having an equal distribution of the four nucleotides (dA, dC, dG, dT) and having a length of e.g., 5 to 50 nucleotides shows, on DNA level, constant propagation of plasmid DNA in *E. coli* and is still associated, on RNA level, with the beneficial properties with respect to supporting RNA stability and translational efficiency is encompassed. Consequently, in some embodiments, the poly(A) sequence contained in an RNA molecule described herein essentially consists of A nucleotides, but is interrupted by a random sequence of the four nucleotides (A, C, G, U). Such random sequence may be 5 to 50, 10 to 30, or 10 to 20 nucleotides in length.

In some embodiments, no nucleotides other than A nucleotides flank a poly(A) sequence at its 3'-end, i.e., the poly(A) sequence is not masked or followed at its 3'-end by a nucleotide other than A.

In some embodiments, the poly(A) sequence may comprise at least 20, at least 30, at least 40, at least 80, or at least 100 and up to 500, up to 400, up to 300, up to 200, or up to 150 nucleotides. In some embodiments, the poly(A) sequence may essentially consist of at least 20, at least 30, at least 40, at least 80, or at least 100 and up to 500, up to 400, up to 300, up to 200, or up to 150 nucleotides. In some embodiments, the poly(A) sequence may consist of at least 20, at least 30, at least 40, at least 80, or at least 100 and up to 500, up to 400, up to 300, up to 200, or up to 150 nucleotides. In some embodiments, the poly(A) sequence comprises at least 100 nucleotides. In some embodiments, the poly(A) sequence comprises about 150 nucleotides. In some embodiments, the poly(A) sequence comprises about 120 nucleotides.

According to the disclosure, vaccine antigen is preferably administered as single-stranded, 5'-capped mRNA that is translated into the respective protein upon entering antigen-presenting cells (APCs). Preferably, the RNA contains structural elements optimized for maximal efficacy of the RNA with respect to stability and translational efficiency (5'-cap, 5'-UTR, 3'-UTR, poly(A) sequence).

In one embodiment, beta-S-ARCA(D1) is utilized as specific capping structure at the 5'-end of the RNA. In one embodiment, the 5'-UTR sequence is derived from the human alpha-globin mRNA. In one embodiment, two re-iterated 3'-UTRs derived from the human beta-globin mRNA are placed between the coding sequence and the poly(A) sequence to assure higher maximum protein levels and prolonged persistence of the mRNA. In one embodiment, a poly(A) sequence measuring 110 nucleotides in length, consisting of a stretch of 30 adenosine residues, followed by a 10 nucleotide linker sequence and another 70 adenosine residues is used. This poly(A) sequence was designed to enhance RNA stability and translational efficiency in dendritic cells.

The RNA is preferably administered as lipoplex particles, preferably comprising DOTMA and DOPE, as further described below. Such particles are preferably administered by systemic administration, in particular by intravenous administration.

In the context of the present disclosure, the term "transcription" relates to a process, wherein the genetic code in a DNA sequence is transcribed into RNA. Subsequently, the RNA may be translated into peptide or protein.

According to the present invention, the term "transcription" comprises "in vitro transcription", wherein the term "in vitro transcription" relates to a process wherein RNA, in particular mRNA, is in vitro synthesized in a cell-free system, preferably using appropriate cell extracts. Preferably, cloning vectors are applied for the generation of transcripts. These cloning vectors are generally designated as transcription vectors and are according to the present invention encompassed by the term "vector". According to the present invention, the RNA used in the present invention preferably is in vitro transcribed RNA (IVT-RNA) and may be obtained by in vitro transcription of an appropriate DNA template. The promoter for controlling transcription can be any promoter for any RNA polymerase. Particular examples of RNA polymerases are the T7, T3, and SP6 RNA polymerases. Preferably, the in vitro transcription according to the invention is controlled by a T7 or SP6 promoter. A DNA template for in vitro transcription may be obtained by cloning of a nucleic acid, in particular cDNA, and introducing it into an appropriate vector for in vitro transcription. The cDNA may be obtained by reverse transcription of RNA.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

The RNA encoding vaccine antigen to be administered according to the invention is non-immunogenic. The RNA encoding immunostimulant to be administered according to the invention may be non-immunogenic.

The term "non-immunogenic RNA" as used herein refers to RNA that does not induce a response by the immune system upon administration, e.g., to a mammal, or induces a weaker response than would have been induced by the same RNA that differs only in that it has not been subjected to the modifications and treatments that render the non-immunogenic RNA non-immunogenic, i.e., than would have been induced by standard RNA (stdRNA). In one preferred embodiment, non-immunogenic RNA, which is also termed modified RNA (modRNA) herein, is rendered non-immunogenic by incorporating modified nucleosides suppressing RNA-mediated activation of innate immune receptors into the RNA and removing double-stranded RNA (dsRNA).

For rendering the non-immunogenic RNA non-immunogenic by the incorporation of modified nucleosides, any modified nucleoside may be used as long as it lowers or suppresses immunogenicity of the RNA. Particularly preferred are modified nucleosides that suppress RNA-mediated activation of innate immune receptors. In one embodiment, the modified nucleosides comprises a replacement of one or more uridines with a nucleoside comprising a modified nucleobase. In one embodiment, the modified nucleobase is a modified uracil. In one embodiment, the nucleoside comprising a modified nucleobase is selected from the group consisting of 3-methyl-uridine ($m^3U$), 5-methoxy-uridine ($mo^5U$), 5-aza-uridine, 6-aza-uridine, 2-thio-5-aza-uridine, 2-thio-uridine ($s^2U$), 4-thio-uridine ($s^4U$), 4-thio-pseudouridine, 2-thio-pseudouridine, 5-hydroxy-uridine ($ho^5U$), 5-aminoallyl-uridine, 5-halo-uridine (e.g., 5-iodo-uridine or 5-bromo-uridine), uridine 5-oxyacetic acid ($cmo^5U$), uridine 5-oxyacetic acid methyl ester ($mcmo^5U$), 5-carboxymethyl-uridine ($cm^5U$), 1-carboxymethyl-pseudouridine, 5-carboxyhydroxymethyl-uridine ($chm^5U$), 5-carboxyhydroxymethyl-uridine methyl ester ($mchm^5U$), 5-methoxycarbonylmethyl-uridine ($mcm^5U$), 5 methoxycarbonylmethyl-2-thio-uridine ($mcm^5s^2U$), 5-aminomethyl-2-thio-uridine ($nm^5s^2U$), 5-methylaminomethyl-uridine ($mnm^5U$), 1-ethyl-pseudouridine, 5-methylaminomethyl-2-thio-uridine ($mnm^5s^2U$), 5-methylaminomethyl-2-seleno-uridine ($mnm^5se^2U$), 5-carbamoylmethyl-uridine ($ncm^5U$), 5-carboxymethylaminomethyl-uridine ($cmnm^5U$), 5-carboxymethylaminomethyl-2-thio-uridine ($cmnm^5s^2U$), 5-propynyl-uridine, 1-propynyl-pseudouridine, 5-taurinomethyl-uridine ($\tau m^5U$), 1-taurinomethyl-pseudouridine, 5-taurinomethyl-2-thio-uridine (τm5s2U), 1-taurinomethyl-4-thio-pseudouridine), 5-methyl-2 thio uridine ($m^5s^2U$), 1 methyl 4 thio pseudouridine ($m^1s^4\psi$), 4-thio-1-methyl-pseudouridine, 3-methyl-pseudouridine ($m^3\psi$), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyl-dihydrouridine ($m^5D$), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine, 3-(3-amino-3-carboxypropyl)uridine ($acp^3U$), 1-methyl-3-(3-amino-3-carboxypropyl)pseudouridine ($acp^3\psi$), 5-(isopentenylaminomethyl)uridine ($inm^5U$), 5-(isopentenylaminomethyl)-2-thio-uridine ($inm^5s^2U$), α-thio-uridine, 2'-O-methyl-uridine (Um), 5,2'-O-dimethyl-uridine ($m^5Um$), 2'-O-methyl-pseudouridine (ψm), 2-thio-2'-O-methyl-uridine ($s^2Um$), 5-methoxycarbonylmethyl-2'-O-methyl-uridine ($mcm^5Um$), 5-carbamoylmethyl-2'-O-methyl-uridine ($ncm^5Um$), 5-carboxymethylaminomethyl-2'-O-methyl-uridine ($cmnm^5Um$), 3,2'-O-dimethyl-uridine ($m^3Um$), 5-(isopentenylaminomethyl)-2'-O-methyl-uridine ($inm^5Um$), 1-thio-uridine, deoxythymidine, 2'-F-ara-uridine, 2'-F-uridine, 2'-OH-ara-uridine, 5-(2-carbomethoxyvinyl) uridine, and 5-[3-(1-E-propenylamino)uridine. In one particularly preferred embodiment, the nucleoside comprising a modified nucleobase is pseudouridine (ψ), N1-methyl-pseudouridine (m1ψ) or 5-methyl-uridine (m5U), in particular N1-methyl-pseudouridine.

In one embodiment, the replacement of one or more uridines with a nucleoside comprising a modified nucleobase comprises a replacement of at least 1%, at least 2%, at least 3%, at least 4%, at least 5%, at least 10%, at least 25%, at least 50%, at least 75%, at least 90%, at least 95%, at least 96%, at least 97%, at least 98%, at least 99% or 100% of the uridines.

During synthesis of mRNA by in vitro transcription (IVT) using T7 RNA polymerase significant amounts of aberrant products, including double-stranded RNA (dsRNA) are produced due to unconventional activity of the enzyme. dsRNA induces inflammatory cytokines and activates effector enzymes leading to protein synthesis inhibition. dsRNA can be removed from RNA such as IVT RNA, for example, by ion-pair reversed phase HPLC using a non-porous or porous C-18 polystyrene-divinylbenzene (PS-DVB) matrix. Alternatively, an enzymatic based method using *E. coli* RNaseIII that specifically hydrolyzes dsRNA but not ssRNA, thereby eliminating dsRNA contaminants from IVT RNA preparations can be used. Furthermore, dsRNA can be separated from ssRNA by using a cellulose material. In one embodiment, an RNA preparation is contacted with a cellulose material and the ssRNA is separated from the cellulose material under conditions which allow binding of dsRNA to the cellulose material and do not allow binding of ssRNA to the cellulose material.

As the term is used herein, "remove" or "removal" refers to the characteristic of a population of first substances, such as non-immunogenic RNA, being separated from the proximity of a population of second substances, such as dsRNA, wherein the population of first substances is not necessarily devoid of the second substance, and the population of second substances is not necessarily devoid of the first substance. However, a population of first substances characterized by the removal of a population of second substances has a measurably lower content of second substances as compared to the non-separated mixture of first and second substances.

In one embodiment, the removal of dsRNA from non-immunogenic RNA comprises a removal of dsRNA such that less than 10%, less than 5%, less than 4%, less than 3%, less than 2%, less than 1%, less than 0.5%, less than 0.3%, or less than 0.1% of the RNA in the non-immunogenic RNA composition is dsRNA. In one embodiment, the non-immunogenic RNA is free or essentially free of dsRNA. In some embodiments, the non-immunogenic RNA composition comprises a purified preparation of single-stranded nucleoside modified RNA. For example, in some embodiments, the purified preparation of single-stranded nucleoside modified RNA is substantially free of double stranded RNA (dsRNA). In some embodiments, the purified preparation is at least 90%, at least 91%, at least 92%, at least 93%, at least 94%, at least 95%, at least 96%, at least 97%, at least 98%, at least 99%, at least 99.5%, or at least 99.9% single stranded nucleoside modified RNA, relative to all other nucleic acid molecules (DNA, dsRNA, etc.).

In one embodiment, the non-immunogenic RNA is translated in a cell more efficiently than standard RNA with the same sequence. In one embodiment, translation is enhanced by a factor of 2-fold relative to its unmodified counterpart. In one embodiment, translation is enhanced by a 3-fold factor. In one embodiment, translation is enhanced by a 4-fold factor. In one embodiment, translation is enhanced by a 5-fold factor. In one embodiment, translation is enhanced by a 6-fold factor. In one embodiment, translation is enhanced by a 7-fold factor. In one embodiment, translation is enhanced by an 8-fold factor. In one embodiment, translation is enhanced by a 9-fold factor. In one embodiment, translation is enhanced by a 10-fold factor. In one embodiment, translation is enhanced by a 15-fold factor. In one embodiment, translation is enhanced by a 20-fold factor. In one embodiment, translation is enhanced by a 50-fold factor. In one embodiment, translation is enhanced by a 100-fold factor. In one embodiment, translation is enhanced by a 200-fold factor. In one embodiment, translation is enhanced by a 500-fold factor. In one embodiment, translation is enhanced by a 1000-fold factor. In one embodiment, translation is enhanced by a 2000-fold factor. In one embodiment, the factor is 10-1000-fold. In one embodiment, the factor is 10-100-fold. In one embodiment, the factor is 10-200-fold. In one embodiment, the factor is 10-300-fold. In one embodiment, the factor is 10-500-fold. In one embodiment, the factor is 20-1000-fold. In one embodiment, the factor is 30-1000-fold. In one embodiment, the factor is 50-1000-fold. In one embodiment, the factor is 100-1000-fold. In one embodiment, the factor is 200-1000-fold. In one embodiment, translation is enhanced by any other significant amount or range of amounts.

In one embodiment, the non-immunogenic RNA exhibits significantly less innate immunogenicity than standard RNA with the same sequence. In one embodiment, the non-immunogenic RNA exhibits an innate immune response that is 2-fold less than its unmodified counterpart. In one embodiment, innate immunogenicity is reduced by a 3-fold factor. In one embodiment, innate immunogenicity is reduced by a 4-fold factor. In one embodiment, innate immunogenicity is reduced by a 5-fold factor. In one embodiment, innate immunogenicity is reduced by a 6-fold factor. In one embodiment, innate immunogenicity is reduced by a 7-fold factor. In one embodiment, innate immunogenicity is reduced by a 8-fold factor. In one embodiment, innate immunogenicity is reduced by a 9-fold factor. In one embodiment, innate immunogenicity is reduced by a 10-fold factor. In one embodiment, innate immunogenicity is reduced by a 15-fold factor. In one embodiment, innate immunogenicity is reduced by a 20-fold factor. In one embodiment, innate immunogenicity is reduced by a 50-fold factor. In one embodiment, innate immunogenicity is reduced by a 100-fold factor. In one embodiment, innate immunogenicity is reduced by a 200-fold factor. In one embodiment, innate immunogenicity is reduced by a 500-fold factor. In one embodiment, innate immunogenicity is reduced by a 1000-fold factor. In one embodiment, innate immunogenicity is reduced by a 2000-fold factor.

The term "exhibits significantly less innate immunogenicity" refers to a detectable decrease in innate immunogenicity. In one embodiment, the term refers to a decrease such that an effective amount of the non-immunogenic RNA can be administered without triggering a detectable innate immune response. In one embodiment, the term refers to a decrease such that the non-immunogenic RNA can be repeatedly administered without eliciting an innate immune response sufficient to detectably reduce production of the protein encoded by the non-immunogenic RNA. In one embodiment, the decrease is such that the non-immunogenic RNA can be repeatedly administered without eliciting an innate immune response sufficient to eliminate detectable production of the protein encoded by the non-immunogenic RNA.

"Immunogenicity" is the ability of a foreign substance, such as RNA, to provoke an immune response in the body of a human or other animal. The innate immune system is the component of the immune system that is relatively unspecific and immediate. It is one of two main components of the vertebrate immune system, along with the adaptive immune system.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence.

As used herein, the terms "linked," "fused", or "fusion" are used interchangeably. These terms refer to the joining together of two or more elements or components or domains.

Antigen

The present invention comprises the administration of non-immunogenic RNA encoding a peptide or protein comprising an epitope for inducing an immune response against an antigen in a subject also designated herein as "vaccine antigen", "peptide and protein antigen" or simply "antigen".

In one embodiment, the RNA encoding the antigen molecule is expressed in cells of the subject to provide the antigen molecule. In one embodiment, expression of the antigen molecule is at the cell surface. In one embodiment, the antigen molecule is presented in the context of MHC. In one embodiment, the RNA encoding the antigen molecule is transiently expressed in cells of the subject. In one embodiment, the RNA encoding the antigen molecule is administered systemically. In one embodiment, after systemic administration of the RNA encoding the antigen molecule, expression of the RNA encoding the antigen molecule in spleen occurs. In one embodiment, after systemic administration of the RNA encoding the antigen molecule, expression of the RNA encoding the antigen molecule in antigen presenting cells, preferably professional antigen presenting cells occurs. In one embodiment, the antigen presenting cells are selected from the group consisting of dendritic cells, macrophages and B cells. In one embodiment, after systemic administration of the RNA encoding the antigen molecule, no or essentially no expression of the RNA encoding the antigen molecule in lung and/or liver occurs. In one embodiment, after systemic administration of the RNA encoding the antigen molecule, expression of the RNA encoding the antigen molecule in spleen is at least 5-fold the amount of expression in lung.

The peptide and protein antigens suitable for use according to the disclosure typically include a peptide or protein comprising an epitope for inducing an immune response. The peptide or protein or epitope may be derived from a target antigen, i.e. the antigen against which an immune response is to be elicited. For example, the peptide or protein antigen or the epitope contained within the peptide or protein antigen may be a target antigen or a fragment or variant of a target antigen.

The antigen molecule or a procession product thereof, e.g., a fragment thereof, may bind to the antigen receptor such as TCR or CAR carried by immune effector cells. In one embodiment, the antigen molecule is selected from the group consisting of the antigen expressed by a target cell to which the immune effector cells are targeted or a fragment thereof, or a variant of the antigen or the fragment.

A peptide and protein antigen which is provided to a subject according to the invention by administering RNA encoding the peptide and protein antigen, i.e., a vaccine antigen, preferably results in stimulation, priming and/or expansion of immune effector cells in the subject being provided the peptide or protein antigen. Said stimulated, primed and/or expanded immune effector cells are preferably directed against a target antigen, in particular a target antigen expressed by diseased cells, tissues and/or organs, i.e., a disease-associated antigen. Thus, a vaccine antigen may comprise the disease-associated antigen, or a fragment or variant thereof. In one embodiment, such fragment or variant is immunologically equivalent to the disease-associated antigen. In the context of the present disclosure, the term "fragment of an antigen" or "variant of an antigen" means an agent which results in stimulation, priming and/or expansion of immune effector cells which stimulated, primed and/or expanded immune effector cells target the antigen, i.e. a disease-associated antigen, in particular when presented by diseased cells, tissues and/or organs. Thus, the vaccine antigen may correspond to or may comprise the disease-associated antigen, may correspond to or may comprise a fragment of the disease-associated antigen or may correspond to or may comprise an antigen which is homologous to the disease-associated antigen or a fragment thereof. If the vaccine antigen comprises a fragment of the disease-associated antigen or an amino acid sequence which is homologous to a fragment of the disease-associated antigen said fragment or amino acid sequence may comprise an epitope of the disease-associated antigen to which the antigen receptor of the immune effector cells is targeted or a sequence which is homologous to an epitope of the disease-associated antigen. Thus, according to the disclosure, a vaccine antigen may comprise an immunogenic fragment of a disease-associated antigen or an amino acid sequence being homologous to an immunogenic fragment of a disease-associated antigen. An "immunogenic fragment of an antigen" according to the disclosure preferably relates to a fragment of an antigen which is capable of stimulating, priming and/or expanding immune effector cells carrying an antigen receptor binding to the antigen or cells expressing the antigen. It is preferred that the vaccine antigen (similar to the disease-associated antigen) provides the relevant epitope for binding by the antigen receptor present on the immune effector cells. In one embodiment, the vaccine antigen or a fragment thereof (similar to the disease-associated antigen) is expressed on the surface of a cell such as an antigen-presenting cell (optionally in the context of MHC) so as to provide the relevant epitope for binding by immune effector cells. The vaccine antigen may be a recombinant antigen.

In one embodiment of all aspects of the invention, the RNA encoding the vaccine antigen is expressed in cells of a subject to provide the antigen or a procession product thereof for binding by the antigen receptor expressed by immune effector cells, said binding resulting in stimulation, priming and/or expansion of the immune effector cells.

The term "immunologically equivalent" means that the immunologically equivalent molecule such as the immunologically equivalent amino acid sequence exhibits the same or essentially the same immunological properties and/or exerts the same or essentially the same immunological effects, e.g., with respect to the type of the immunological effect. In the context of the present disclosure, the term "immunologically equivalent" is preferably used with respect to the immunological effects or properties of antigens or antigen variants used for immunization. For example, an amino acid sequence is immunologically equivalent to a reference amino acid sequence if said amino acid sequence when exposed to the immune system of a subject such as T cells binding to the reference amino acid sequence or cells expressing the reference amino acid sequence induces an immune reaction having a specificity of reacting with the reference amino acid sequence. Thus, a molecule which is immunologically equivalent to an antigen exhibits the same or essentially the same properties and/or exerts the same or essentially the same effects regarding the stimulation, priming and/or expansion of T cells as the antigen to which the T cells are targeted.

"Activation" or "stimulation", as used herein, refers to the state of an immune effector cell such as T cell that has been sufficiently stimulated to induce detectable cellular proliferation. Activation can also be associated with initiation of signaling pathways, induced cytokine production, and detectable effector functions. The term "activated immune effector cells" refers to, among other things, immune effector cells that are undergoing cell division.

The term "priming" refers to a process wherein an immune effector cell such as a T cell has its first contact with its specific antigen and causes differentiation into effector cells such as effector T cells.

The term "clonal expansion" or "expansion" refers to a process wherein a specific entity is multiplied. In the context of the present disclosure, the term is preferably used in the context of an immunological response in which lymphocytes are stimulated by an antigen, proliferate, and the specific lymphocyte recognizing said antigen is amplified. Preferably, clonal expansion leads to differentiation of the lymphocytes.

The term "antigen" relates to an agent comprising an epitope against which an immune response can be generated. The term "antigen" includes, in particular, proteins and peptides. In one embodiment, an antigen is presented or present on the surface of cells of the immune system such as antigen presenting cells like dendritic cells or macrophages. An antigen or a procession product thereof such as a T cell epitope is in one embodiment bound by an antigen receptor. Accordingly, an antigen or a procession product thereof may react specifically with immune effector cells such as T-lymphocytes (T cells). In one embodiment, an antigen is a disease-associated antigen, such as a tumor antigen, a viral antigen, or a bacterial antigen and an epitope is derived from such antigen.

The term "disease-associated antigen" is used in its broadest sense to refer to any antigen associated with a disease. A disease-associated antigen is a molecule which contains epitopes that will stimulate a host's immune system to make a cellular antigen-specific immune response and/or a humoral antibody response against the disease. The disease-associated antigen or an epitope thereof may therefore be used for therapeutic purposes. Disease-associated antigens may be associated with infection by microbes, typically microbial antigens, or associated with cancer, typically tumors.

The term "tumor antigen" refers to a constituent of cancer cells which may be derived from the cytoplasm, the cell surface and the cell nucleus. In particular, it refers to those antigens which are produced intracellularly or as surface antigens on tumor cells. A tumor antigen is typically expressed preferentially by cancer cells (e.g., it is expressed at higher levels in cancer cells than in non-cancer cells) and in some instances it is expressed solely by cancer cells. Examples of tumor antigens include, without limitation, p53, ART-4, BAGE, beta-catenin/m, Bcr-abL CAMEL, CAP-1, CASP-8, CDC27/m, CDK4/m, CEA, the cell surface proteins of the claudin family, such as CLAUDIN-6, CLAUDIN-18.2 and CLAUDIN-12, c-MYC, CT, Cyp-B, DAM, ELF2M, ETV6-AML1, G250, GAGE, GnT-V, Gap 100, HAGE, HER-2/neu, HPV-E7, HPV-E6, HAST-2, hTERT (or hTRT), LAGE, LDLR/FUT, MAGE-A, preferably MAGE-A1, MAGE-A2, MAGE-A3, MAGE-A4, MAGE-A5, MAGE-A6, MAGE-A7, MAGE-A8, MAGE-A9, MAGE-A 10, MAGE-A 1 1, or MAGE-A12, MAGE-B, MAGE-C, MART-1/Melan-A, MC1R, Myosin/m, MUC1, MUM-1, MUM-2, MUM-3, NA88-A, NF1, NY-ESO-1, NY-BR-1, pI90 minor BCR-abL, Pml/RARa, PRAME, proteinase 3, PSA, PSM, RAGE, RU1 or RU2, SAGE, SART-1 or SART-3, SCGB3A2, SCP1, SCP2, SCP3, SSX, SURVIVIN, TEL/AML1, TPI/m, TRP-1, TRP-2, TRP-2/INT2, TPTE, WT, and WT-1.

The term "viral antigen" refers to any viral component having antigenic properties, i.e. being able to provoke an immune response in an individual. The viral antigen may be a viral ribonucleoprotein or an envelope protein.

The term "bacterial antigen" refers to any bacterial component having antigenic properties, i.e. being able to provoke an immune response in an individual. The bacterial antigen may be derived from the cell wall or cytoplasm membrane of the bacterium.

The term “expressed on the cell surface” or “associated with the cell surface” means that a molecule such as a receptor or antigen is associated with and located at the plasma membrane of a cell, wherein at least a part of the molecule faces the extracellular space of said cell and is accessible from the outside of said cell, e.g., by antibodies located outside the cell. In this context, a part is preferably at least 4, preferably at least 8, preferably at least 12, more preferably at least 20 amino acids. The association may be direct or indirect. For example, the association may be by one or more transmembrane domains, one or more lipid anchors, or by the interaction with any other protein, lipid, saccharide, or other structure that can be found on the outer leaflet of the plasma membrane of a cell. For example, a molecule associated with the surface of a cell may be a transmembrane protein having an extracellular portion or may be a protein associated with the surface of a cell by interacting with another protein that is a transmembrane protein.

“Cell surface” or “surface of a cell” is used in accordance with its normal meaning in the art, and thus includes the outside of the cell which is accessible to binding by proteins and other molecules. An antigen is expressed on the surface of cells if it is located at the surface of said cells and is accessible to binding by e.g. antigen-specific antibodies added to the cells. In one embodiment, an antigen expressed on the surface of cells is an integral membrane protein having an extracellular portion which may be recognized by a CAR.

The term “extracellular portion” or “exodomain” in the context of the present invention refers to a part of a molecule such as a protein that is facing the extracellular space of a cell and preferably is accessible from the outside of said cell, e.g., by binding molecules such as antibodies located outside the cell. Preferably, the term refers to one or more extracellular loops or domains or a fragment thereof.

The term “epitope” refers to a part or fragment of a molecule such as an antigen that is recognized by the immune system. For example, the epitope may be recognized by T cells, B cells or antibodies. An epitope of an antigen may include a continuous or discontinuous portion of the antigen and may be between about 5 and about 100, such as between about 5 and about 50, more preferably between about 8 and about 30, most preferably between about 8 and about 25 amino acids in length, for example, the epitope may be preferably 9, 10, 11, 12, 13, 14, 15, 16, 17, 18, 19, 20, 21, 22, 23, 24, or 25 amino acids in length. In one embodiment, an epitope is between about 10 and about 25 amino acids in length. The term “epitope” includes T cell epitopes.

The term “T cell epitope” refers to a part or fragment of a protein that is recognized by a T cell when presented in the context of MHC molecules. The term “major histocompatibility complex” and the abbreviation “MHC” includes MHC class I and MHC class II molecules and relates to a complex of genes which is present in all vertebrates. MHC proteins or molecules are important for signaling between lymphocytes and antigen presenting cells or diseased cells in immune reactions, wherein the MHC proteins or molecules bind peptide epitopes and present them for recognition by T cell receptors on T cells. The proteins encoded by the MHC are expressed on the surface of cells, and display both self-antigens (peptide fragments from the cell itself) and non-self-antigens (e.g., fragments of invading microorganisms) to a T cell. In the case of class I MHC/peptide complexes, the binding peptides are typically about 8 to about 10 amino acids long although longer or shorter peptides may be effective. In the case of class II MHC/peptide complexes, the binding peptides are typically about 10 to about 25 amino acids long and are in particular about 13 to about 18 amino acids long, whereas longer and shorter peptides may be effective.

In one embodiment, the target antigen is a tumor antigen and the vaccine antigen or a fragment thereof (e.g., an epitope) is derived from the tumor antigen. The tumor antigen may be a “standard” antigen, which is generally known to be expressed in various cancers. The tumor antigen may also be a “neo-antigen”, which is specific to an individual’s tumor and has not been previously recognized by the immune system. A neo-antigen or neo-epitope may result from one or more cancer-specific mutations in the genome of cancer cells resulting in amino acid changes. If the tumor antigen is a neo-antigen, the vaccine antigen preferably comprises an epitope or a fragment of said neo-antigen comprising one or more amino acid changes.

Cancer mutations vary with each individual. Thus, cancer mutations that encode novel epitopes (neo-epitopes) represent attractive targets in the development of vaccine compositions and immunotherapies. The efficacy of tumor immunotherapy relies on the selection of cancer-specific antigens and epitopes capable of inducing a potent immune response within a host. RNA can be used to deliver patient-specific tumor epitopes to a patient. Dendritic cells (DCs) residing in the spleen represent antigen-presenting cells of particular interest for RNA expression of immunogenic epitopes or antigens such as tumor epitopes. The use of multiple epitopes has been shown to promote therapeutic efficacy in tumor vaccine compositions. Rapid sequencing of the tumor mutanome may provide multiple epitopes for individualized vaccines which can be encoded by RNA described herein, e.g., as a single polypeptide wherein the epitopes are optionally separated by linkers. In certain embodiments of the present disclosure, the RNA encodes at least one epitope, at least two epitopes, at least three epitopes, at least four epitopes, at least five epitopes, at least six epitopes, at least seven epitopes, at least eight epitopes, at least nine epitopes, or at least ten epitopes. Exemplary embodiments include RNA that encodes at least five epitopes (termed a “pentatope”) and RNA that encodes at least ten epitopes (termed a “decatope”).

According to the various aspects of the invention, the aim is preferably to provide an immune response against cancer cells expressing a tumor antigen and to treat a cancer disease involving cells expressing a tumor antigen.

The peptide and protein antigen can be 2-100 amino acids, including for example, 5 amino acids, 10 amino acids, 15 amino acids, 20 amino acids, 25 amino acids, 30 amino acids, 35 amino acids, 40 amino acids, 45 amino acids, or 50 amino acids in length. In some embodiments, a peptide can be greater than 50 amino acids. In some embodiments, the peptide can be greater than 100 amino acids.

The peptide or protein antigen can be any peptide or protein that can induce or increase the ability of the immune system to develop antibodies and T cell responses to the peptide or protein.

In one embodiment, vaccine antigen is recognized by an immune effector cell. Preferably, the vaccine antigen if recognized by an immune effector cell is able to induce in the presence of appropriate co-stimulatory signals, stimulation, priming and/or expansion of the immune effector cell carrying an antigen receptor recognizing the vaccine antigen. In the context of the embodiments of the present invention, the vaccine antigen is preferably presented or present on the surface of a cell, preferably an antigen presenting cell. Recognition of a disease-associated antigen on the surface of a diseased cell by the immune effector cells may result in an immune reaction against the antigen (or cell expressing the antigen).

In one embodiment of all aspects of the invention, an antigen is expressed in a diseased cell such as a cancer cell. In one embodiment, an antigen is presented by a diseased cell such as a cancer cell. In one embodiment, an antigen receptor is a TCR which binds to an epitope of an antigen presented in the context of MHC. In one embodiment, binding of a TCR when expressed by T cells and/or present on T cells to an antigen presented by cells such as antigen presenting cells results in stimulation, priming and/or expansion of said T cells. In one embodiment, binding of a TCR when expressed by T cells and/or present on T cells to an antigen presented on diseased cells such as cancer cells results in cytolysis and/or apoptosis of the diseased cells, wherein said T cells preferably release cytotoxic factors, e.g. perforins and granzymes. In one embodiment, an antigen is expressed on the surface of a diseased cell such as a cancer cell. In one embodiment, an antigen receptor is a CAR which binds to an extracellular domain or to an epitope in an extracellular domain of an antigen. In one embodiment, a CAR binds to native epitopes of an antigen present on the surface of living cells. In one embodiment, binding of a CAR when expressed by T cells and/or present on T cells to an antigen present on cells such as antigen presenting cells results in stimulation, priming and/or expansion of said T cells. In one embodiment, binding of a CAR when expressed by T cells and/or present on T cells to an antigen present on diseased cells such as cancer cells results in cytolysis and/or apoptosis of the diseased cells, wherein said T cells preferably release cytotoxic factors, e.g. perforins and granzymes.

Immunostimulants

An "immunostimulant" is any substance that stimulates the immune system by inducing activation or increasing activity of any of the immune system's components, in particular immune effector cells. The immunostimulant may be pro-inflammatory (e.g., when treating infections or cancer), or anti-inflammatory (e.g., when treating autoimmune diseases).

According to one aspect, the immunostimulant is a cytokine or a variant thereof. Examples of cytokines include interferons, such as interferon-alpha (IFN-α) or interferon-gamma (IFN-γ), interleukins, such as IL2, IL7, IL12, IL15 and IL23, colony stimulating factors, such as M-CSF and GM-CSF, and tumor necrosis factor. According to another aspect, the immunostimulant includes an adjuvant-type immunostimulatory agent such as APC Toll-like Receptor agonists or costimulatory/cell adhesion membrane proteins. Examples of Toll-like Receptor agonists include costimulatory/adhesion proteins such as CD80, CD86, and ICAM-1.

Cytokines are a category of small proteins (~5-20 kDa) that are important in cell signaling. Their release has an effect on the behavior of cells around them. Cytokines are involved in autocrine signaling, paracrine signaling and endocrine signaling as immunomodulating agents. Cytokines include chemokines, interferons, interleukins, lymphokines, and tumour necrosis factors but generally not hormones or growth factors (despite some overlap in the terminology). Cytokines are produced by a broad range of cells, including immune cells like macrophages, B lymphocytes, T lymphocytes and mast cells, as well as endothelial cells, fibroblasts, and various stromal cells. A given cytokine may be produced by more than one type of cell. Cytokines act through receptors, and are especially important in the immune system; cytokines modulate the balance between humoral and cell-based immune responses, and they regulate the maturation, growth, and responsiveness of particular cell populations. Some cytokines enhance or inhibit the action of other cytokines in complex ways.

According to the disclosure, a cytokine may be a naturally occurring cytokine or a functional fragment or variant thereof. A cytokine may be human cytokine and may be derived from any vertebrate, especially any mammal. One particularly preferred cytokine is interferon-α.

Interferons

Interferons (IFNs) are a group of signaling proteins made and released by host cells in response to the presence of several pathogens, such as viruses, bacteria, parasites, and also tumor cells. In a typical scenario, a virus-infected cell will release interferons causing nearby cells to heighten their anti-viral defenses.

Based on the type of receptor through which they signal, interferons are typically divided among three classes: type I interferon, type II interferon, and type III interferon.

All type I interferons bind to a specific cell surface receptor complex known as the IFN-α/β receptor (IFNAR) that consists of IFNAR1 and IFNAR2 chains.

The type I interferons present in humans are IFNα, IFNβ, IFNε, IFNκ and IFNω. In general, type I interferons are produced when the body recognizes a virus that has invaded it. They are produced by fibroblasts and monocytes. Once released, type I interferons bind to specific receptors on target cells, which leads to expression of proteins that will prevent the virus from producing and replicating its RNA and DNA.

The IFNα proteins are produced mainly by plasmacytoid dendritic cells (pDCs). They are mainly involved in innate immunity against viral infection. The genes responsible for their synthesis come in 13 subtypes that are called IFNA1, IFNA2, IFNA4, IFNA5, IFNA6, IFNA7, IFNA8, IFNA10, IFNA13, IFNA14, IFNA16, IFNA17, IFNA21. These genes are found together in a cluster on chromosome 9.

The IFNβ proteins are produced in large quantities by fibroblasts. They have antiviral activity that is involved mainly in innate immune response. Two types of IFNβ have been described, IFNβ1 and IFNβ3. The natural and recombinant forms of IFNβ1 have antiviral, antibacterial, and anticancer properties.

Type II interferon (IFNγ in humans) is also known as immune interferon and is activated by IL12. Furthermore, type II interferons are released by cytotoxic T cells and T helper cells.

Type III interferons signal through a receptor complex consisting of IL10R2 (also called CRF2-4) and IFNLR1 (also called CRF2-12). Although discovered more recently than type I and type II IFNs, recent information demonstrates the importance of type III IFNs in some types of virus or fungal infections.

In general, type I and II interferons are responsible for regulating and activating the immune response.

According to the disclosure, a type I interferon is preferably IFNα or IFNβ, more preferably IFNα.

According to the disclosure, an interferon may be a naturally occurring interferon or a functional fragment or variant thereof. An interferon may be human interferon and may be derived from any vertebrate, especially any mammal.

Interleukins

Interleukins (ILs) are a group of cytokines (secreted proteins and signal molecules) that can be divided into four major groups based on distinguishing structural features. However, their amino acid sequence similarity is rather weak (typically 15-25% identity). The human genome encodes more than 50 interleukins and related proteins.

According to the disclosure, an interleukin may be a naturally occurring interleukin or a functional fragment or variant thereof. An interleukin may be human interleukin and may be derived from any vertebrate, especially any mammal.

Extended-PK Group

Immunostimulant polypeptides described herein can be prepared as fusion or chimeric polypeptides that include an immunostimulant portion and a heterologous polypeptide (i.e., a polypeptide that is not an immunostimulant). The immunostimulant may be fused to an extended-PK group, which increases circulation half-life. Non-limiting examples of extended-PK groups are described infra. It should be understood that other PK groups that increase the circulation half-life of immunostimulants such as cytokines, or variants thereof, are also applicable to the present disclosure. In certain embodiments, the extended-PK group is a serum albumin domain (e.g., mouse serum albumin, human serum albumin).

As used herein, the term "PK" is an acronym for "pharmacokinetic" and encompasses properties of a compound including, by way of example, absorption, distribution, metabolism, and elimination by a subject. As used herein, an "extended-PK group" refers to a protein, peptide, or moiety that increases the circulation half-life of a biologically active molecule when fused to or administered together with the biologically active molecule. Examples of an extended-PK group include serum albumin (e.g., HSA), Immunoglobulin Fc or Fc fragments and variants thereof, transferrin and variants thereof, and human serum albumin (HSA) binders (as disclosed in U.S. Publication Nos. 2005/0287153 and 2007/0003549). Other exemplary extended-PK groups are disclosed in Kontermann, Expert Opin Biol Ther, 2016 July; 16(7):903-15 which is herein incorporated by reference in its entirety. As used herein, an "extended-PK" immunostimulant refers to an immunostimulant moiety in combination with an extended-PK group. In one embodiment, the extended-PK immunostimulant is a fusion protein in which an immunostimulant moiety is linked or fused to an extended-PK group.

In certain embodiments, the serum half-life of an extended-PK immunostimulant is increased relative to the immunostimulant alone (i.e., the immunostimulant not fused to an extended-PK group). In certain embodiments, the serum half-life of the extended-PK immunostimulant is at least 20, 40, 60, 80, 100, 120, 150, 180, 200, 400, 600, 800, or 1000% longer relative to the serum half-life of the immunostimulant alone. In certain embodiments, the serum half-life of the extended-PK immunostimulant is at least 1.5 fold, 2-fold, 2.5-fold, 3-fold, 3.5 fold, 4-fold, 4.5-fold, 5-fold, 6-fold, 7-fold, 8-fold, 10-fold, 12-fold, 13-fold, 15-fold, 17-fold, 20-fold, 22-fold, 25-fold, 27-fold, 30-fold, 35-fold, 40-fold, or 50-fold greater than the serum half-life of the immunostimulant alone. In certain embodiments, the serum half-life of the extended-PK immunostimulant is at least 10 hours, 15 hours, 20 hours, 25 hours, 30 hours, 35 hours, 40 hours, 50 hours, 60 hours, 70 hours, 80 hours, 90 hours, 100 hours, 110 hours, 120 hours, 130 hours, 135 hours, 140 hours, 150 hours, 160 hours, or 200 hours.

As used herein, "half-life" refers to the time taken for the serum or plasma concentration of a compound such as a peptide or protein to reduce by 50%, in vivo, for example due to degradation and/or clearance or sequestration by natural mechanisms. An extended-PK immunostimulant suitable for use herein is stabilized in vivo and its half-life increased by, e.g., fusion to serum albumin (e.g., HSA or MSA), which resist degradation and/or clearance or sequestration. The half-life can be determined in any manner known per se, such as by pharmacokinetic analysis. Suitable techniques will be clear to the person skilled in the art, and may for example generally involve the steps of suitably administering a suitable dose of the amino acid sequence or compound to a subject; collecting blood samples or other samples from said subject at regular intervals; determining the level or concentration of the amino acid sequence or compound in said blood sample; and calculating, from (a plot of) the data thus obtained, the time until the level or concentration of the amino acid sequence or compound has been reduced by 50% compared to the initial level upon dosing. Further details are provided in, e.g., standard handbooks, such as Kenneth, A. et al., Chemical Stability of Pharmaceuticals: A Handbook for Pharmacists and in Peters et al., Pharmacokinetic Analysis: A Practical Approach (1996). Reference is also made to Gibaldi, M. et al., Pharmacokinetics, 2nd Rev. Edition, Marcel Dekker (1982).

In certain embodiments, the extended-PK group includes serum albumin, or fragments thereof or variants of the serum albumin or fragments thereof (all of which for the purpose of the present disclosure are comprised by the term "albumin"). Polypeptides described herein may be fused to albumin (or a fragment or variant thereof) to form albumin fusion proteins. Such albumin fusion proteins are described in U.S. Publication No. 20070048282.

As used herein, "albumin fusion protein" refers to a protein formed by the fusion of at least one molecule of albumin (or a fragment or variant thereof) to at least one molecule of a protein such as a therapeutic protein, in particular an immunostimulant. The albumin fusion protein may be generated by translation of a nucleic acid in which a polynucleotide encoding a therapeutic protein is joined in-frame with a polynucleotide encoding an albumin. The therapeutic protein and albumin, once part of the albumin fusion protein, may each be referred to as a "portion", "region" or "moiety" of the albumin fusion protein (e.g., a "therapeutic protein portion" or an "albumin protein portion"). In a highly preferred embodiment, an albumin fusion protein comprises at least one molecule of a therapeutic protein (including, but not limited to a mature form of the therapeutic protein) and at least one molecule of albumin (including but not limited to a mature form of albumin). In one embodiment, an albumin fusion protein is processed by a host cell such as a cell of the target organ for administered RNA, e.g. a liver cell, and secreted into the circulation. Processing of the nascent albumin fusion protein that occurs in the secretory pathways of the host cell used for expression of the RNA may include, but is not limited to signal peptide cleavage; formation of disulfide bonds; proper folding; addition and processing of carbohydrates (such as for example, N- and O-linked glycosylation); specific proteolytic cleavages; and/or assembly into multimeric proteins. An albumin fusion protein is preferably encoded by RNA in a non-processed form which in particular has a signal peptide at its N-terminus and following secretion by a cell is preferably present in the processed form wherein in particular the signal peptide has been cleaved off. In a most preferred embodiment, the "processed form of an albumin fusion protein" refers to an albumin fusion protein product which has undergone N-terminal signal peptide cleavage, herein also referred to as a "mature albumin fusion protein".

In preferred embodiments, albumin fusion proteins comprising a therapeutic protein have a higher plasma stability compared to the plasma stability of the same therapeutic protein when not fused to albumin. Plasma stability typically refers to the time period between when the therapeutic protein is administered in vivo and carried into the bloodstream and when the therapeutic protein is degraded and cleared from the bloodstream, into an organ, such as the kidney or liver, that ultimately clears the therapeutic protein from the body. Plasma stability is calculated in terms of the half-life of the therapeutic protein in the bloodstream. The half-life of the therapeutic protein in the bloodstream can be readily determined by common assays known in the art.

As used herein, "albumin" refers collectively to albumin protein or amino acid sequence, or an albumin fragment or variant, having one or more functional activities (e.g., biological activities) of albumin. In particular, "albumin" refers to human albumin or fragments or variants thereof especially the mature form of human albumin, or albumin from other vertebrates or fragments thereof, or variants of these molecules. The albumin may be derived from any vertebrate, especially any mammal, for example human, cow, sheep, or pig. Non-mammalian albumins include, but are not limited to, hen and salmon. The albumin portion of the albumin fusion protein may be from a different animal than the therapeutic protein portion.

In certain embodiments, the albumin is human serum albumin (HSA), or fragments or variants thereof, such as those disclosed in U.S. Pat. No. 5,876,969, WO 2011/124718, WO 2013/075066, and WO 2011/0514789.

The terms, human serum albumin (HSA) and human albumin (HA) are used interchangeably herein. The terms, "albumin and "serum albumin" are broader, and encompass human serum albumin (and fragments and variants thereof) as well as albumin from other species (and fragments and variants thereof).

As used herein, a fragment of albumin sufficient to prolong the therapeutic activity or plasma stability of the therapeutic protein refers to a fragment of albumin sufficient in length or structure to stabilize or prolong the therapeutic activity or plasma stability of the protein so that the plasma stability of the therapeutic protein portion of the albumin fusion protein is prolonged or extended compared to the plasma stability in the non-fusion state.

The albumin portion of the albumin fusion proteins may comprise the full length of the albumin sequence, or may include one or more fragments thereof that are capable of stabilizing or prolonging the therapeutic activity or plasma stability. Such fragments may be of 10 or more amino acids in length or may include about 15, 20, 25, 30, 50, or more contiguous amino acids from the albumin sequence or may include part or all of specific domains of albumin. For instance, one or more fragments of HSA spanning the first two immunoglobulin-like domains may be used. In a preferred embodiment, the HSA fragment is the mature form of HSA.

Generally speaking, an albumin fragment or variant will be at least 100 amino acids long, preferably at least 150 amino acids long.

According to the disclosure, albumin may be naturally occurring albumin or a fragment or variant thereof. Albumin may be human albumin and may be derived from any vertebrate, especially any mammal.

Preferably, the albumin fusion protein comprises albumin as the N-terminal portion, and a therapeutic protein as the C-terminal portion. Alternatively, an albumin fusion protein comprising albumin as the C-terminal portion, and a therapeutic protein as the N-terminal portion may also be used. In other embodiments, the albumin fusion protein has a therapeutic protein fused to both the N-terminus and the C-terminus of albumin. In a preferred embodiment, the therapeutic proteins fused at the N- and C-termini are the same therapeutic proteins. In another preferred embodiment, the therapeutic proteins fused at the N- and C-termini are different therapeutic proteins. In one embodiment, the different therapeutic proteins are both cytokines.

In one embodiment, the therapeutic protein(s) is (are) joined to the albumin through (a) peptide linker(s). A linker peptide between the fused portions may provide greater physical separation between the moieties and thus maximize the accessibility of the therapeutic protein portion, for instance, for binding to its cognate receptor. The linker peptide may consist of amino acids such that it is flexible or more rigid. The linker sequence may be cleavable by a protease or chemically.

As used herein, the term "Fc region" refers to the portion of a native immunoglobulin formed by the respective Fc domains (or Fc moieties) of its two heavy chains. As used herein, the term "Fc domain" refers to a portion or fragment of a single immunoglobulin (Ig) heavy chain wherein the Fc domain does not comprise an Fv domain. In certain embodiments, an Fc domain begins in the hinge region just upstream of the papain cleavage site and ends at the C-terminus of the antibody. Accordingly, a complete Fc domain comprises at least a hinge domain, a CH2 domain, and a CH3 domain. In certain embodiments, an Fc domain comprises at least one of: a hinge (e.g., upper, middle, and/or lower hinge region) domain, a CH2 domain, a CH3 domain, a CH4 domain, or a variant, portion, or fragment thereof. In certain embodiments, an Fc domain comprises a complete Fc domain (i.e., a hinge domain, a CH2 domain, and a CH3 domain). In certain embodiments, an Fc domain comprises a hinge domain (or portion thereof) fused to a CH3 domain (or portion thereof). In certain embodiments, an Fc domain comprises a CH2 domain (or portion thereof) fused to a CH3 domain (or portion thereof). In certain embodiments, an Fc domain consists of a CH3 domain or portion thereof. In certain embodiments, an Fc domain consists of a hinge domain (or portion thereof) and a CH3 domain (or portion thereof). In certain embodiments, an Fc domain consists of a CH2 domain (or portion thereof) and a CH3 domain. In certain embodiments, an Fc domain consists of a hinge domain (or portion thereof) and a CH2 domain (or portion thereof). In certain embodiments, an Fc domain lacks at least a portion of a CH2 domain (e.g., all or part of a CH2 domain). An Fc domain herein generally refers to a polypeptide comprising all or part of the Fc domain of an immunoglobulin heavy-chain. This includes, but is not limited to, polypeptides comprising the entire CH1, hinge, CH2, and/or CH3 domains as well as fragments of such peptides comprising only, e.g., the hinge, CH2, and CH3 domain. The Fc domain may be derived from an immunoglobulin of any species and/or any subtype, including, but not limited to, a human IgG1, IgG2, IgG3, IgG4, IgD, IgA, IgE, or IgM antibody. The Fc domain encompasses native Fc and Fc variant molecules. As set forth herein, it will be understood by one of ordinary skill in the art that any Fc domain may be modified such that it varies in amino acid sequence from the native Fc domain of a naturally occurring immunoglobulin molecule. In certain embodiments, the Fc domain has reduced effector function (e.g., FcγR binding).

The Fc domains of a polypeptide described herein may be derived from different immunoglobulin molecules. For example, an Fc domain of a polypeptide may comprise a CH2 and/or CH3 domain derived from an IgG1 molecule and a hinge region derived from an IgG3 molecule. In another example, an Fc domain can comprise a chimeric hinge region derived, in part, from an IgG1 molecule and, in part, from an IgG3 molecule. In another example, an Fc domain can comprise a chimeric hinge derived, in part, from an IgG1 molecule and, in part, from an IgG4 molecule.

In certain embodiments, an extended-PK group includes an Fc domain or fragments thereof or variants of the Fc domain or fragments thereof (all of which for the purpose of the present disclosure are comprised by the term "Fc domain"). The Fc domain does not contain a variable region that binds to antigen. Fc domains suitable for use in the present disclosure may be obtained from a number of different sources. In certain embodiments, an Fc domain is derived from a human immunoglobulin. In certain embodiments, the Fc domain is from a human IgG1 constant region. It is understood, however, that the Fc domain may be derived from an immunoglobulin of another mammalian species, including for example, a rodent (e.g. a mouse, rat, rabbit, guinea pig) or non-human primate (e.g. chimpanzee, macaque) species.

Moreover, the Fc domain (or a fragment or variant thereof) may be derived from any immunoglobulin class, including IgM, IgG, IgD, IgA, and IgE, and any immunoglobulin isotype, including IgG1, IgG2, IgG3, and IgG4.

A variety of Fc domain gene sequences (e.g., mouse and human constant region gene sequences) are available in the form of publicly accessible deposits. Constant region domains comprising an Fc domain sequence can be selected lacking a particular effector function and/or with a particular modification to reduce immunogenicity. Many sequences of antibodies and antibody-encoding genes have been published and suitable Fc domain sequences (e.g. hinge, CH2, and/or CH3 sequences, or fragments or variants thereof) can be derived from these sequences using art recognized techniques.

In certain embodiments, the extended-PK group is a serum albumin binding protein such as those described in US2005/0287153, US2007/0003549, US2007/0178082, US2007/0269422, US2010/0113339, WO2009/083804, and WO2009/133208, which are herein incorporated by reference in their entirety. In certain embodiments, the extended-PK group is transferrin, as disclosed in U.S. Pat. Nos. 7,176,278 and 8,158,579, which are herein incorporated by reference in their entirety. In certain embodiments, the extended-PK group is a serum immunoglobulin binding protein such as those disclosed in US2007/0178082, US2014/0220017, and US2017/0145062, which are herein incorporated by reference in their entirety. In certain embodiments, the extended-PK group is a fibronectin (Fn)-based scaffold domain protein that binds to serum albumin, such as those disclosed in US2012/0094909, which is herein incorporated by reference in its entirety. Methods of making fibronectin-based scaffold domain proteins are also disclosed in US2012/0094909. A non-limiting example of a Fn3-based extended-PK group is Fn3(HSA), i.e., a Fn3 protein that binds to human serum albumin.

In certain aspects, the extended-PK immunostimulant, suitable for use according to the disclosure, can employ one or more peptide linkers. As used herein, the term "peptide linker" refers to a peptide or polypeptide sequence which connects two or more domains (e.g., the extended-PK moiety and an immunostimulant moiety) in a linear amino acid sequence of a polypeptide chain. For example, peptide linkers may be used to connect an immunostimulant moiety to a HSA domain.

Linkers suitable for fusing the extended-PK group to e.g. an immunostimulant are well known in the art. Exemplary linkers include glycine-serine-polypeptide linkers, glycine-proline-polypeptide linkers, and proline-alanine polypeptide linkers. In certain embodiments, the linker is a glycine-serine-polypeptide linker, i.e., a peptide that consists of glycine and serine residues.

In addition to, or in place of, the heterologous polypeptides described above, an immunostimulant polypeptide described herein can contain sequences encoding a "marker" or "reporter". Examples of marker or reporter genes include β-lactamase, chloramphenicol acetyltransferase (CAT), adenosine deaminase (ADA), aminoglycoside phosphotransferase, dihydrofolate reductase (DHFR), hygromycin-B-hosphotransferase (HPH), thymidine kinase (TK), β-galactosidase, and xanthine guanine phosphoribosyltransferase (XGPRT).

Immune Effector Cells

The immune effector cells to be used herein may be administered to a subject in need of treatment or may be endogenously present in a subject in need of treatment. Administering to the subject RNA encoding a vaccine antigen and an immunostimulant or RNA encoding an immunostimulant allows for the stimulation of the immune effector cells. The methods and agents described herein are, in particular, useful for the treatment of diseases characterized by diseased cells expressing an antigen the immune effector cells are directed to. In one embodiment, the immune effector cells carry an antigen receptor such a T cell receptor (TCR) or chimeric antigen receptor (CAR) having a binding specificity for the antigen or a procession product thereof. In one embodiment, the immune effector cells are present in a subject to be treated and express an antigen receptor. In one embodiment, the immune effector cells are present in a subject to be treated and are genetically modified in vivo in the subject to express an antigen receptor. In one embodiment, immune effector cells either from a subject to be treated or from a different subject are administered to the subject to be treated. The administered immune effector cells may be genetically modified ex vivo prior to administration or genetically modified in vivo in the subject following administration to express an antigen receptor. In one embodiment, an antigen receptor is endogenous to the immune effector cells.

In one embodiment, the immune effector cells include any cell which is responsive to vaccine antigen and immunostimulant. Such responsiveness includes activation, differentiation, proliferation, survival and/or indication of one or more immune effector functions. The cells include, in particular, cells with lytic potential, in particular lymphoid cells, and are preferably T cells, in particular cytotoxic lymphocytes, preferably selected from cytotoxic T cells, natural killer (NK) cells, and lymphokine-activated killer (LAK) cells. Upon activation, each of these cytotoxic lymphocytes triggers the destruction of target cells. For example, cytotoxic T cells trigger the destruction of target cells by either or both of the following means. First, upon activation T cells release cytotoxins such as perforin, granzymes, and granulysin. Perforin and granulysin create pores in the target cell, and granzymes enter the cell and trigger a caspase cascade in the cytoplasm that induces apoptosis (programmed cell death) of the cell. Second, apoptosis can be induced via Fas-Fas ligand interaction between the T cells and target cells. The cells used in connection with the present invention will preferably be autologous cells, although heterologous cells or allogenic cells can be used. In one embodiment, immune effector cells are endogenous to a subject being treated.

The term "effector functions" in the context of the present invention includes any functions mediated by components of the immune system that result, for example, in the killing of diseased cells such as tumor cells, or in the inhibition of tumor growth and/or inhibition of tumor development, including inhibition of tumor dissemination and metastasis. Preferably, the effector functions in the context of the present invention are T cell mediated effector functions. Such functions comprise in the case of a helper T cell ($CD4^+$ T cell) the release of cytokines and/or the activation of $CD8^+$ lymphocytes (CTLs) and/or B cells, and in the case of CTL the elimination of cells, i.e., cells characterized by expression of an antigen, for example, via apoptosis or perforin-mediated cell lysis, production of cytokines such as IFN-γ and TNF-α, and specific cytolytic killing of antigen expressing target cells.

The term "immune effector cell" or "immunoreactive cell" in the context of the present invention relates to a cell which exerts effector functions during an immune reaction. An "immune effector cell" in one embodiment is capable of binding an antigen such as an antigen presented in the context of MHC on a cell or expressed on the surface of a cell and mediating an immune response. For example, immune effector cells comprise T cells (cytotoxic T cells, helper T cells, tumor infiltrating T cells), B cells, natural killer cells, neutrophils, macrophages, and dendritic cells. Preferably, in the context of the present invention, "immune effector cells" are T cells, preferably $CD4^+$ and/or $CD8^+$ T cells, most preferably $CD8^+$ T cells. According to the invention, the term "immune effector cell" also includes a cell which can mature into an immune cell (such as T cell, in particular T helper cell, or cytolytic T cell) with suitable stimulation. Immune effector cells comprise $CD34^+$ hematopoietic stem cells, immature and mature T cells and immature and mature B cells. The differentiation of T cell precursors into a cytolytic T cell, when exposed to an antigen, is similar to clonal selection of the immune system.

Preferably, an "immune effector cell" recognizes an antigen with some degree of specificity, in particular if presented in the context of MHC or present on the surface of diseased cells such as cancer cells. Preferably, said recognition enables the cell that recognizes an antigen to be responsive or reactive. If the cell is a helper T cell ($CD4^+$ T cell) such responsiveness or reactivity may involve the release of cytokines and/or the activation of $CD8^+$ lymphocytes (CTLs) and/or B cells. If the cell is a CTL such responsiveness or reactivity may involve the elimination of cells, i.e., cells characterized by expression of an antigen, for example, via apoptosis or perforin-mediated cell lysis. According to the invention, CTL responsiveness may include sustained calcium flux, cell division, production of cytokines such as IFN-γ and TNF-α, up-regulation of activation markers such as CD44 and CD69, and specific cytolytic killing of antigen expressing target cells. CTL responsiveness may also be determined using an artificial reporter that accurately indicates CTL responsiveness. Such CTL that recognizes an antigen and are responsive or reactive are also termed "antigen-responsive CTL" herein.

In one embodiment, the genetically modified immune effector cells are CAR-expressing immune effector cells. In one embodiment, the genetically modified immune effector cells are TCR-expressing immune effector cells.

The immune effector cells may express an endogenous antigen receptor such as T cell receptor or B cell receptor or may lack expression of an endogenous antigen receptor.

A "lymphoid cell" is a cell which, optionally after suitable modification, e.g. after transfer of an antigen receptor such as a TCR or a CAR, is capable of producing an immune response such as a cellular immune response, or a precursor cell of such cell, and includes lymphocytes, preferably T lymphocytes, lymphoblasts, and plasma cells. A lymphoid cell may be an immune effector cell as described herein. A preferred lymphoid cell is a T cell which can be modified to express an antigen receptor on the cell surface. In one embodiment, the lymphoid cell lacks endogenous expression of a T cell receptor.

The terms "T cell" and "T lymphocyte" are used interchangeably herein and include T helper cells (CD4+ T cells) and cytotoxic T cells (CTLs, CD8+ T cells) which comprise cytolytic T cells. The term "antigen-specific T cell" or similar terms relate to a T cell which recognizes the antigen to which the T cell is targeted and preferably exerts effector functions of T cells. T cells are considered to be specific for antigen if the cells kill target cells expressing an antigen. T cell specificity may be evaluated using any of a variety of standard techniques, for example, within a chromium release assay or proliferation assay. Alternatively, synthesis of lymphokines (such as IFN-γ) can be measured.

T cells belong to a group of white blood cells known as lymphocytes, and play a central role in cell-mediated immunity. They can be distinguished from other lymphocyte types, such as B cells and natural killer cells by the presence of a special receptor on their cell surface called T cell receptor (TCR). The thymus is the principal organ responsible for the maturation of T cells. Several different subsets of T cells have been discovered, each with a distinct function.

T helper cells assist other white blood cells in immunologic processes, including maturation of B cells into plasma cells and activation of cytotoxic T cells and macrophages, among other functions. These cells are also known as CD4+ T cells because they express the CD4 glycoprotein on their surface. Helper T cells become activated when they are presented with peptide antigens by MHC class II molecules that are expressed on the surface of antigen presenting cells (APCs). Once activated, they divide rapidly and secrete small proteins called cytokines that regulate or assist in the active immune response.

Cytotoxic T cells destroy virally infected cells and tumor cells, and are also implicated in transplant rejection. These cells are also known as CD8+ T cells since they express the CD8 glycoprotein on their surface. These cells recognize their targets by binding to antigen associated with MHC class I, which is present on the surface of nearly every cell of the body.

"Regulatory T cells" or "Tregs" are a subpopulation of T cells that modulate the immune system, maintain tolerance to self-antigens, and prevent autoimmune disease. Tregs are immunosuppressive and generally suppress or downregulate induction and proliferation of effector T cells. Tregs express the biomarkers CD4, FoxP3, and CD25.

As used herein, the term "naïve T cell" refers to mature T cells that, unlike activated or memory T cells, have not encountered their cognate antigen within the periphery. Naïve T cells are commonly characterized by the surface expression of L-selectin (CD62L), the absence of the activation markers CD25, CD44 or CD69 and the absence of the memory CD45RO isoform.

As used herein, the term "memory T cells" refers to a subgroup or subpopulation of T cells that have previously encountered and responded to their cognate antigen. At a second encounter with the antigen, memory T cells can reproduce to mount a faster and stronger immune response than the first time the immune system responded to the antigen. Memory T cells may be either $CD4^+$ or $CD8^+$ and usually express CD45RO.

According to the invention, the term "T cell" also includes a cell which can mature into a T cell with suitable stimulation.

A majority of T cells have a T cell receptor (TCR) existing as a complex of several proteins. The TCR of a T cell is able to interact with immunogenic peptides (epitopes) bound to major histocompatibility complex (MHC) molecules and presented on the surface of target cells. Specific binding of the TCR triggers a signal cascade inside the T cell leading to proliferation and differentiation into a maturated effector T cell. The actual T cell receptor is composed of two separate peptide chains, which are produced from the independent T cell receptor alpha and beta (TCRα and TCRβ) genes and are called α- and β-TCR chains. γδ T cells (gamma delta T cells) represent a small subset of T cells that possess a distinct T cell receptor (TCR) on their surface. However, in γδ T cells, the TCR is made up of one γ-chain and one δ-chain. This group of T cells is much less common (2% of total T cells) than the αβ T cells.

All T cells originate from hematopoietic stem cells in the bone marrow. Hematopoietic progenitors derived from hematopoietic stem cells populate the thymus and expand by cell division to generate a large population of immature thymocytes. The earliest thymocytes express neither CD4 nor CD8, and are therefore classed as double-negative (CD4−CD8−) cells. As they progress through their development they become double-positive thymocytes (CD4+ CD8+), and finally mature to single-positive (CD4+CD8− or CD4−CD8+) thymocytes that are then released from the thymus to peripheral tissues.

T cells may generally be prepared in vitro or ex vivo, using standard procedures. For example, T cells may be isolated from bone marrow, peripheral blood or a fraction of bone marrow or peripheral blood of a mammal, such as a patient, using a commercially available cell separation system. Alternatively, T cells may be derived from related or unrelated humans, non-human animals, cell lines or cultures. A sample comprising T cells may, for example, be peripheral blood mononuclear cells (PBMC).

As used herein, the term "NK cell" or "Natural Killer cell" refers to a subset of peripheral blood lymphocytes defined by the expression of CD56 or CD16 and the absence of the T cell receptor. As provided herein, the NK cell can also be differentiated from a stem cell or progenitor cell.

Antigen Receptors

Immune effector cells described herein express an antigen receptor such as a chimeric antigen receptor (CAR) or a T cell receptor (TCR) binding antigen or a procession product thereof, in particular when present on or presented by a target cell, e.g., an antigen presenting cell or a diseased cell. Cells may naturally express an antigen receptor or be modified to express an antigen receptor. In one embodiment, immune effector cells are genetically modified ex vivo/in vitro or in vivo in a subject being treated to express an antigen receptor. In one embodiment, modification to express an antigen receptor takes place ex vivo/in vitro. Subsequently, modified cells may be administered to a patient. In one embodiment, modification to express an antigen receptor takes place in vivo. The cells may be endogenous cells of the patient or may have been administered to a patient.

Chimeric Antigen Receptors

Adoptive cell transfer therapy with CAR-engineered T cells expressing chimeric antigen receptors is a promising anti-cancer therapeutic as CAR-modified T cells can be engineered to target virtually any tumor antigen. For example, patient's T cells may be genetically engineered (genetically modified) to express CARs specifically directed towards antigens on the patient's tumor cells, then infused back into the patient.

According to the invention, the term "CAR" (or "chimeric antigen receptor") is synonymous with the terms "chimeric T cell receptor" and "artificial T cell receptor" and relates to an artificial receptor comprising a single molecule or a complex of molecules which recognizes, i.e. binds to, a target structure (e.g. an antigen) on a target cell such as a cancer cell (e.g. by binding of an antigen binding domain to an antigen expressed on the surface of the target cell) and may confer specificity onto an immune effector cell such as a T cell expressing said CAR on the cell surface. Such cells do not necessarily require processing and presentation of an antigen for recognition of the target cell but rather may recognize preferably with specificity any antigen present on a target cell. Preferably, recognition of the target structure by a CAR results in activation of an immune effector cell expressing said CAR. A CAR may comprise one or more protein units said protein units comprising one or more domains as described herein. The term "CAR" does not include T cell receptors.

A CAR comprises a target-specific binding element otherwise referred to as an antigen binding moiety or antigen binding domain that is generally part of the extracellular domain of the CAR. The antigen binding domain recognizes a ligand that acts as a cell surface marker on target cells associated with a particular disease state. Specifically, the CAR of the invention targets the antigen such as tumor antigen on a diseased cell such as tumor cell.

In one embodiment, the binding domain in the CAR binds specifically to the antigen. In one embodiment, the antigen to which the binding domain in the CAR binds is expressed in a cancer cell (tumor antigen). In one embodiment, the antigen is expressed on the surface of a cancer cell. In one embodiment, the binding domain binds to an extracellular domain or to an epitope in an extracellular domain of the antigen. In one embodiment, the binding domain binds to native epitopes of the antigen present on the surface of living cells.

In one embodiment of the invention, an antigen binding domain comprises a variable region of a heavy chain of an immunoglobulin (VH) with a specificity for the antigen and a variable region of a light chain of an immunoglobulin (VL) with a specificity for the antigen. In one embodiment, an immunoglobulin is an antibody. In one embodiment, said heavy chain variable region (VH) and the corresponding light chain variable region (VL) are connected via a peptide linker. Preferably, the antigen binding moiety portion in the CAR is a scFv.

The CAR is designed to comprise a transmembrane domain that is fused to the extracellular domain of the CAR. In one embodiment, the transmembrane domain is not naturally associated with one of the domains in the CAR. In one embodiment, the transmembrane domain is naturally associated with one of the domains in the CAR. In one embodiment, the transmembrane domain is modified by amino acid substitution to avoid binding of such domains to the transmembrane domains of the same or different surface membrane proteins to minimize interactions with other members of the receptor complex. The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the alpha, beta or zeta chain of the T cell receptor, CD28, CD3 epsilon, CD45, CD4, CD5, CD8, CD9, CD16, CD22, CD33, CD37, CD64, CD80, CD86, CD134, CD137, CD154. Alternatively the transmembrane domain may be synthetic, in which case it will comprise predominantly hydrophobic residues such as leucine and valine. Preferably a triplet of phenylalanine, tryptophan and valine will be found at each end of a synthetic transmembrane domain.

In some instances, the CAR comprises a hinge domain which forms the linkage between the transmembrane domain and the extracellular domain.

The cytoplasmic domain or otherwise the intracellular signaling domain of the CAR is responsible for activation of at least one of the normal effector functions of the immune cell in which the CAR has been placed in. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

It is known that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

In one embodiment, the CAR comprises a primary cytoplasmic signaling sequence derived from CD3-zeta. Further, the cytoplasmic domain of the CAR may comprise the CD3-zeta signaling domain combined with a costimulatory signaling region.

The identity of the co-stimulation domain is limited only in that it has the ability to enhance cellular proliferation and survival upon binding of the targeted moiety by the CAR. Suitable co-stimulation domains include CD28, CD137 (4-1 BB), a member of the tumor necrosis factor receptor (TNFR) superfamily, CD134 (OX40), a member of the TNFR-superfamily of receptors, and CD278 (ICOS), a CD28-superfamily co-stimulatory molecule expressed on activated T cells. The skilled person will understand that sequence variants of these noted co-stimulation domains can be used without adversely impacting the invention, where the variants have the same or similar activity as the domain on which they are modeled. Such variants will have at least about 80% sequence identity to the amino acid sequence of the domain from which they are derived. In some embodiments of the invention, the CAR constructs comprise two co-stimulation domains. While the particular combinations include all possible variations of the four noted domains, specific examples include CD28+CD137 (4-1 BB) and CD28+CD134 (OX40).

The cytoplasmic signaling sequences within the cytoplasmic signaling portion of the CAR may be linked to each other in a random or specified order. Optionally, a short oligo- or polypeptide linker, preferably between 2 and 10 amino acids in length may form the linkage. A glycine-serine doublet provides a particularly suitable linker.

In one embodiment, the CAR comprises a signal peptide which directs the nascent protein into the endoplasmic reticulum. In one embodiment, the signal peptide precedes the antigen binding domain. In one embodiment, the signal peptide is derived from an immunoglobulin such as IgG.

The term "antibody" includes an immunoglobulin comprising at least two heavy (H) chains and two light (L) chains inter-connected by disulfide bonds. Each heavy chain is comprised of a heavy chain variable region (abbreviated herein as VH) and a heavy chain constant region. Each light chain is comprised of a light chain variable region (abbreviated herein as VL) and a light chain constant region. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system. An antibody binds, preferably specifically binds with an antigen. Antibodies can be intact immunoglobulins derived from natural sources or from recombinant sources and can be immunoreactive portions or fragments of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab')2, as well as single chain antibodies and humanized antibodies (Harlow et al., 1999, In: Using Antibodies: A Laboratory Manual, Cold Spring Harbor Laboratory Press, NY; Harlow et al., 1989, in: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

The term "antibody fragment" refers to a portion of an intact antibody and typically comprises the antigenic determining variable regions of an intact antibody.

Examples of antibody fragments include, but are not limited to, Fab, Fab', F(ab')2, and Fv fragments, linear antibodies, scFv antibodies, and multispecific antibodies formed from antibody fragments.

An "antibody heavy chain", as used herein, refers to the larger of the two types of polypeptide chains present in antibody molecules in their naturally occurring conformations.

An "antibody light chain", as used herein, refers to the smaller of the two types of polypeptide chains present in antibody molecules in their naturally occurring conformations, K and A light chains refer to the two major antibody light chain isotypes.

According to the disclosure, a CAR which when present on a T cell recognizes an antigen such as on the surface of antigen presenting cells or diseased cells such as cancer cells, such that the T cell is stimulated, and/or expanded or exerts effector functions as described above.

Genetic Modification of Immune Effector Cells

Particles that are functionalized for specific targeting of immune effector cells, such as $CD8^+$ T cells, may be used ex vivo/in vitro or in vivo for delivering nucleic acid encoding antigen receptors to immune effector cells such as T cells to produce cells genetically modified to express the antigen receptors. Such genetic modification includes non-viral-based DNA transfection, non-viral-based RNA transfection, e.g., mRNA transfection, transposon-based systems, and viral-based systems. Non-viral-based DNA transfection has low risk of insertional mutagenesis. Transposon-based systems can integrate transgenes more efficiently than plasmids that do not contain an integrating element. Viral-based systems include the use of γ-retroviruses and lentiviral vectors. γ-Retroviruses are relatively easy to produce, efficiently and permanently transduce T cells, and have preliminarily proven safe from an integration standpoint in primary human T cells. Lentiviral vectors also efficiently and permanently transduce T cells but are more expensive to manufacture. They are also potentially safer than retrovirus based systems.

In one embodiment of all aspects of the invention, T cells or T cell progenitors are transfected either ex vivo or in vivo with nucleic acid encoding the antigen receptor. In one embodiment, a combination of ex vivo and in vivo transfection may be used. In one embodiment of all aspects of the invention, the T cells or T cell progenitors are from the subject to be treated. In one embodiment of all aspects of the invention, the T cells or T cell progenitors are from a subject which is different to the subject to be treated.

In one aspect of the invention, CAR T cells may be produced in vivo, and therefore nearly instantaneously, using particles such as nanoparticles targeted to T cells. For example, lipid and/or polymer-based nanoparticles may be coupled to CD8-specific targeting moieties for binding to CD8 on T cells. Upon binding to T cells, these particles are endocytosed. Their contents, for example nucleic acid encoding antigen receptor, e.g., plasmid DNA encoding an anti-tumor antigen CAR, may be directed to the T cell nucleus due to, for example, the inclusion of peptides containing microtubule-associated sequences (MTAS) and nuclear localization signals (NLSs). The inclusion of transposons flanking the nucleic acid encoding antigen receptor, e.g., the CAR gene expression cassette, and a separate nucleic acid, e.g., plasmid, encoding a hyperactive transposase, may allow for the efficient integration of the nucleic acid encoding antigen receptor, e.g., the CAR vector, into chromosomes.

Another possibility is to use the CRISPR/Cas9 method to deliberately place an antigen receptor coding sequence such as a CAR coding sequence at a specific locus. For example, existing T cell receptors (TCR) may be knocked out, while knocking in the CAR and placing it under the dynamic regulatory control of the endogenous promoter that would otherwise moderate TCR expression.

Accordingly, besides nucleic acid encoding an antigen receptor the particles described herein may also deliver as cargo gene editing tools like CRISPR/Cas9 (or related) or transposon systems like sleeping beauty or piggy bag. Such tools (e.g. transposase, gene editing tools like CRISPR/Cas9) for genomic integration/editing may be delivered as protein or coding nucleic acid (DNA or RNA). Nevertheless, also delivery of mRNA is an option to induce transient expression of antigen receptors like CARs or T-cell receptors (TCR).

In one embodiment of all aspects of the invention, the cells genetically modified to express an antigen receptor are stably or transiently transfected with nucleic acid encoding the antigen receptor. Thus, the nucleic acid encoding the antigen receptor is integrated or not integrated into the genome of the cells.

In one embodiment of all aspects of the invention, the cells genetically modified to express an antigen receptor are inactivated for expression of an endogenous T cell receptor and/or endogenous HLA.

In one embodiment of all aspects of the invention, the cells described herein may be autologous, allogeneic or syngeneic to the subject to be treated. In one embodiment, the present disclosure envisions the removal of cells from a patient and the subsequent re-delivery of the cells to the patient. In one embodiment, the present disclosure does not envision the removal of cells from a patient. In the latter case all steps of genetic modification of cells are performed in vivo.

The term "autologous" is used to describe anything that is derived from the same subject. For example, "autologous transplant" refers to a transplant of tissue or organs derived from the same subject. Such procedures are advantageous because they overcome the immunological barrier which otherwise results in rejection.

The term "allogeneic" is used to describe anything that is derived from different individuals of the same species. Two or more individuals are said to be allogeneic to one another when the genes at one or more loci are not identical.

The term "syngeneic" is used to describe anything that is derived from individuals or tissues having identical genotypes, i.e., identical twins or animals of the same inbred strain, or their tissues.

The term "heterologous" is used to describe something consisting of multiple different elements. As an example, the transfer of one individual's bone marrow into a different individual constitutes a heterologous transplant. A heterologous gene is a gene derived from a source other than the subject.

Nucleic Acid Containing Particles

Nucleic acids described herein such as non-immunogenic RNA encoding a peptide or protein comprising an epitope for inducing an immune response against an antigen and RNA encoding an immunostimulant may be administered formulated as particles.

In the context of the present disclosure, the term "particle" relates to a structured entity formed by molecules or molecule complexes. In one embodiment, the term "particle" relates to a micro- or nano-sized structure, such as a micro- or nano-sized compact structure dispersed in a medium. In one embodiment, a particle is a nucleic acid containing particle such as a particle comprising DNA, RNA or a mixture thereof.

Electrostatic interactions between positively charged molecules such as polymers and lipids and negatively charged nucleic acid are involved in particle formation. This results in complexation and spontaneous formation of nucleic acid particles. In one embodiment, a nucleic acid particle is a nanoparticle.

As used in the present disclosure, "nanoparticle" refers to a particle having an average diameter suitable for parenteral administration.

A "nucleic acid particle" can be used to deliver nucleic acid to a target site of interest (e.g., cell, tissue, organ, and the like). A nucleic acid particle may be formed from at least one cationic or cationically ionizable lipid or lipid-like material such as DOTAP, at least one cationic polymer such as protamine, or a mixture thereof and nucleic acid. Nucleic acid particles include lipid nanoparticle (LNP)-based and lipoplex (LPX)-based formulations.

Without intending to be bound by any theory, it is believed that the cationic or cationically ionizable lipid or lipid-like material and the cationic polymer combine together with the nucleic acid to form aggregates, and this aggregation results in colloidally stable particles.

In one embodiment, particles described herein further comprise at least one lipid or lipid-like material other than a cationic or cationically ionizable lipid or lipid-like material, at least one polymer other than a cationic polymer, or a mixture thereof In some embodiments, nucleic acid particles comprise more than one type of nucleic acid molecules, where the molecular parameters of the nucleic acid molecules may be similar or different from each other, like with respect to molar mass or fundamental structural elements such as molecular architecture, capping, coding regions or other features, Nucleic acid particles described herein may have an average diameter that in one embodiment ranges from about 30 nm to about 1000 nm, from about 50 nm to about 800 nm, from about 70 nm to about 600 nm, from about 90 nm to about 400 nm, or from about 100 nm to about 300 nm.

Nucleic acid particles described herein may exhibit a polydispersity index less than about 0.5, less than about 0.4, less than about 0.3, or about 0.2 or less. By way of example, the nucleic acid particles can exhibit a polydispersity index in a range of about 0.1 to about 0.3 or about 0.2 to about 0.3.

Nucleic acid particles described herein can be prepared using a wide range of methods that may involve obtaining a colloid from at least one cationic or cationically ionizable lipid or lipid-like material and/or at least one cationic polymer and mixing the colloid with nucleic acid to obtain nucleic acid particles.

The term "colloid" as used herein relates to a type of homogeneous mixture in which dispersed particles do not settle out. The insoluble particles in the mixture are microscopic, with particle sizes between 1 and 1000 nanometers. The mixture may be termed a colloid or a colloidal suspension. Sometimes the term "colloid" only refers to the particles in the mixture and not the entire suspension.

For the preparation of colloids comprising at least one cationic or cationically ionizable lipid or lipid-like material and/or at least one cationic polymer methods are applicable herein that are conventionally used for preparing liposomal vesicles and are appropriately adapted. The most commonly used methods for preparing liposomal vesicles share the following fundamental stages: (i) lipids dissolution in organic solvents, (ii) drying of the resultant solution, and (iii) hydration of dried lipid (using various aqueous media). In the film hydration method, lipids are firstly dissolved in a suitable organic solvent, and dried down to yield a thin film at the bottom of the flask. The obtained lipid film is hydrated using an appropriate aqueous medium to produce a liposomal dispersion. Furthermore, an additional downsizing step may be included. Reverse phase evaporation is an alternative method to the film hydration for preparing liposomal vesicles that involves formation of a water-in-oil emulsion between an aqueous phase and an organic phase containing lipids. A brief sonication of this mixture is required for system homogenization. The removal of the organic phase under reduced pressure yields a milky gel that turns subsequently into a liposomal suspension.

Other methods having organic solvent free characteristics may also be used according to the present disclosure for preparing a colloid.

LNPs typically consist of four components: ionizable cationic lipids, phospholipids, cholesterol, and polyethylene glycol (PEG)-lipids. Each component is responsible for payload protection, and enables effective intracellular delivery. LNPs may be prepared by mixing lipids dissolved in ethanol rapidly with nucleic acid in an aqueous buffer.

The term "average diameter" refers to the mean hydrodynamic diameter of particles as measured by dynamic laser light scattering (DLS) with data analysis using the so-called cumulant algorithm, which provides as results the so-called $Z_{average}$ with the dimension of a length, and the polydispersity index (PI), which is dimensionless (Koppel, D., J. Chem. Phys. 57, 1972, pp 4814-4820, ISO 13321). Here "average diameter", "diameter" or "size" for particles is used synonymously with this value of the $Z_{average}$.

The "polydispersity index" is preferably calculated based on dynamic light scattering measurements by the so-called cumulant analysis as mentioned in the definition of the "average diameter". Under certain prerequisites, it can be taken as a measure of the size distribution of an ensemble of nanoparticles.

Different types of nucleic acid containing particles have been described previously to be suitable for delivery of nucleic acid in particulate form (e.g. Kaczmarek, J. C. et al., 2017, Genome Medicine 9, 60). For non-viral nucleic acid delivery vehicles, nanoparticle encapsulation of nucleic acid physically protects nucleic acid from degradation and, depending on the specific chemistry, can aid in cellular uptake and endosomal escape.

The present disclosure describes particles comprising nucleic acid, at least one cationic or cationically ionizable lipid or lipid-like material, and/or at least one cationic polymer which associate with nucleic acid to form nucleic acid particles and compositions comprising such particles. The nucleic acid particles may comprise nucleic acid which is complexed in different forms by non-covalent interactions to the particle. The particles described herein are not viral particles, in particular infectious viral particles, i.e., they are not able to virally infect cells.

Suitable cationic or cationically ionizable lipids or lipid-like materials and cationic polymers are those that form nucleic acid particles and are included by the term "particle forming components" or "particle forming agents". The term "particle forming components" or "particle forming agents" relates to any components which associate with nucleic acid to form nucleic acid particles. Such components include any component which can be part of nucleic acid particles.

Cationic Polymer

Given their high degree of chemical flexibility, polymers are commonly used materials for nanoparticle-based delivery. Typically, cationic polymers are used to electrostatically condense the negatively charged nucleic acid into nanoparticles. These positively charged groups often consist of amines that change their state of protonation in the pH range between 5.5 and 7.5, thought to lead to an ion imbalance that results in endosomal rupture. Polymers such as poly-L-lysine, polyamidoamine, protamine and polyethyleneimine, as well as naturally occurring polymers such as chitosan have all been applied to nucleic acid delivery and are suitable as cationic polymers herein. In addition, some investigators have synthesized polymers specifically for nucleic acid delivery. Poly(β-amino esters), in particular, have gained widespread use in nucleic acid delivery owing to their ease of synthesis and biodegradability. Such synthetic polymers are also suitable as cationic polymers herein.

A "polymer," as used herein, is given its ordinary meaning, i.e., a molecular structure comprising one or more repeat units (monomers), connected by covalent bonds. The repeat units can all be identical, or in some cases, there can be more than one type of repeat unit present within the polymer. In some cases, the polymer is biologically derived, i.e., a biopolymer such as a protein. In some cases, additional moieties can also be present in the polymer, for example targeting moieties such as those described herein.

If more than one type of repeat unit is present within the polymer, then the polymer is said to be a "copolymer." It is to be understood that the polymer being employed herein can be a copolymer. The repeat units forming the copolymer can be arranged in any fashion. For example, the repeat units can be arranged in a random order, in an alternating order, or as a "block" copolymer, i.e., comprising one or more regions each comprising a first repeat unit (e.g., a first block), and one or more regions each comprising a second repeat unit (e.g., a second block), etc. Block copolymers can have two (a diblock copolymer), three (a triblock copolymer), or more numbers of distinct blocks.

In certain embodiments, the polymer is biocompatible. Biocompatible polymers are polymers that typically do not result in significant cell death at moderate concentrations. In certain embodiments, the biocompatible polymer is biodegradable, i.e., the polymer is able to degrade, chemically and/or biologically, within a physiological environment, such as within the body.

In certain embodiments, polymer may be protamine or polyalkyleneimine, in particular protamine.

The term "protamine" refers to any of various strongly basic proteins of relatively low molecular weight that are rich in arginine and are found associated especially with DNA in place of somatic histones in the sperm cells of various animals (as fish). In particular, the term "protamine" refers to proteins found in fish sperm that are strongly basic, are soluble in water, are not coagulated by heat, and yield chiefly arginine upon hydrolysis. In purified form, they are used in a long-acting formulation of insulin and to neutralize the anticoagulant effects of heparin.

According to the disclosure, the term "protamine" as used herein is meant to comprise any protamine amino acid sequence obtained or derived from natural or biological sources including fragments thereof and multimeric forms of said amino acid sequence or fragment thereof as well as (synthesized) polypeptides which are artificial and specifically designed for specific purposes and cannot be isolated from native or biological sources.

In one embodiment, the polyalkyleneimine comprises polyethylenimine and/or polypropylenimine, preferably polyethyleneimine. A preferred polyalkyleneimine is polyethyleneimine (PEI). The average molecular weight of PEI is preferably $0.75\cdot10^2$ to $10^7$ Da, preferably 1000 to $10^5$ Da, more preferably 10000 to 40000 Da, more preferably 15000 to 30000 Da, even more preferably 20000 to 25000 Da.

Preferred according to the disclosure is linear polyalkyleneimine such as linear polyethyleneimine (PEI). Cationic polymers (including polycationic polymers) contemplated for use herein include any cationic polymers which are able to electrostatically bind nucleic acid. In one embodiment, cationic polymers contemplated for use herein include any cationic polymers with which nucleic acid can be associated, e.g. by forming complexes with the nucleic acid or forming vesicles in which the nucleic acid is enclosed or encapsulated.

Particles described herein may also comprise polymers other than cationic polymers, i.e., non-cationic polymers and/or anionic polymers. Collectively, anionic and neutral polymers are referred to herein as non-cationic polymers.

Lipid and Lipid-Like Material

The terms "lipid" and "lipid-like material" are broadly defined herein as molecules which comprise one or more hydrophobic moieties or groups and optionally also one or more hydrophilic moieties or groups. Molecules comprising hydrophobic moieties and hydrophilic moieties are also frequently denoted as amphiphiles. Lipids are usually poorly soluble in water. In an aqueous environment, the amphiphilic nature allows the molecules to self-assemble into organized structures and different phases. One of those phases consists of lipid bilayers, as they are present in vesicles, multilamellar/unilamellar liposomes, or membranes in an aqueous environment. Hydrophobicity can be conferred by the inclusion of apolar groups that include, but are not limited to, long-chain saturated and unsaturated aliphatic hydrocarbon groups and such groups substituted by one or more aromatic, cycloaliphatic, or heterocyclic group(s). The hydrophilic groups may comprise polar and/or charged groups and include carbohydrates, phosphate, carboxylic, sulfate, amino, sulfhydryl, nitro, hydroxyl, and other like groups.

As used herein, the term "amphiphilic" refers to a molecule having both a polar portion and a non-polar portion. Often, an amphiphilic compound has a polar head attached to a long hydrophobic tail. In some embodiments, the polar portion is soluble in water, while the non-polar portion is insoluble in water. In addition, the polar portion may have either a formal positive charge, or a formal negative charge. Alternatively, the polar portion may have both a formal positive and a negative charge, and be a zwitterion or inner salt. For purposes of the disclosure, the amphiphilic compound can be, but is not limited to, one or a plurality of natural or non-natural lipids and lipid-like compounds.

The term "lipid-like material", "lipid-like compound" or "lipid-like molecule" relates to substances that structurally and/or functionally relate to lipids but may not be considered as lipids in a strict sense. For example, the term includes compounds that are able to form amphiphilic layers as they are present in vesicles, multilamellar/unilamellar liposomes, or membranes in an aqueous environment and includes surfactants, or synthesized compounds with both hydrophilic and hydrophobic moieties. Generally speaking, the term refers to molecules, which comprise hydrophilic and hydrophobic moieties with different structural organization, which may or may not be similar to that of lipids. As used herein, the term "lipid" is to be construed to cover both lipids and lipid-like materials unless otherwise indicated herein or clearly contradicted by context.

Specific examples of amphiphilic compounds that may be included in an amphiphilic layer include, but are not limited to, phospholipids, aminolipids and sphingolipids.

In certain embodiments, the amphiphilic compound is a lipid. The term "lipid" refers to a group of organic compounds that are characterized by being insoluble in water, but soluble in many organic solvents. Generally, lipids may be divided into eight categories: fatty acids, glycerolipids, glycerophospholipids, sphingolipids, saccharolipids, polyketides (derived from condensation of ketoacyl subunits), sterol lipids and prenol lipids (derived from condensation of isoprene subunits). Although the term "lipid" is sometimes used as a synonym for fats, fats are a subgroup of lipids called triglycerides. Lipids also encompass molecules such as fatty acids and their derivatives (including tri-, di-, monoglycerides, and phospholipids), as well as sterol-containing metabolites such as cholesterol.

Fatty acids, or fatty acid residues are a diverse group of molecules made of a hydrocarbon chain that terminates with a carboxylic acid group; this arrangement confers the molecule with a polar, hydrophilic end, and a nonpolar, hydrophobic end that is insoluble in water. The carbon chain, typically between four and 24 carbons long, may be saturated or unsaturated, and may be attached to functional groups containing oxygen, halogens, nitrogen, and sulfur. If a fatty acid contains a double bond, there is the possibility of either a cis or trans geometric isomerism, which significantly affects the molecule's configuration. Cis-double bonds cause the fatty acid chain to bend, an effect that is compounded with more double bonds in the chain. Other major lipid classes in the fatty acid category are the fatty esters and fatty amides.

Glycerolipids are composed of mono-, di-, and tri-substituted glycerols, the best-known being the fatty acid triesters of glycerol, called triglycerides. The word "triacylglycerol" is sometimes used synonymously with "triglyceride". In these compounds, the three hydroxyl groups of glycerol are each esterified, typically by different fatty acids. Additional subclasses of glycerolipids are represented by glycosylglycerols, which are characterized by the presence of one or more sugar residues attached to glycerol via a glycosidic linkage.

The glycerophospholipids are amphipathic molecules (containing both hydrophobic and hydrophilic regions) that contain a glycerol core linked to two fatty acid-derived "tails" by ester linkages and to one "head" group by a phosphate ester linkage. Examples of glycerophospholipids, usually referred to as phospholipids (though sphingomyelins are also classified as phospholipids) are phosphatidylcholine (also known as PC, GPCho or lecithin), phosphatidylethanolamine (PE or GPEtn) and phosphatidylserine (PS or GPSer).

Sphingolipids are a complex family of compounds that share a common structural feature, a sphingoid base backbone. The major sphingoid base in mammals is commonly referred to as sphingosine. Ceramides (N-acyl-sphingoid bases) are a major subclass of sphingoid base derivatives with an amide-linked fatty acid. The fatty acids are typically saturated or mono-unsaturated with chain lengths from 16 to 26 carbon atoms. The major phosphosphingolipids of mammals are sphingomyelins (ceramide phosphocholines), whereas insects contain mainly ceramide phosphoethanolamines and fungi have phytoceramide phosphoinositols and mannose-containing headgroups. The glycosphingolipids are a diverse family of molecules composed of one or more sugar residues linked via a glycosidic bond to the sphingoid base. Examples of these are the simple and complex glycosphingolipids such as cerebrosides and gangliosides.

Sterol lipids, such as cholesterol and its derivatives, or tocopherol and its derivatives, are an important component of membrane lipids, along with the glycerophospholipids and sphingomyelins.

Saccharolipids describe compounds in which fatty acids are linked directly to a sugar backbone, forming structures that are compatible with membrane bilayers. In the saccharolipids, a monosaccharide substitutes for the glycerol backbone present in glycerolipids and glycerophospholipids. The most familiar saccharolipids are the acylated glucosamine precursors of the Lipid A component of the lipopolysaccharides in Gram-negative bacteria. Typical lipid A molecules are disaccharides of glucosamine, which are derivatized with as many as seven fatty-acyl chains. The minimal lipopolysaccharide required for growth in *E. coli* is Kdo2-Lipid A, a hexa-acylated disaccharide of glucosamine that is glycosylated with two 3-deoxy-D-manno-octulosonic acid (Kdo) residues.

Polyketides are synthesized by polymerization of acetyl and propionyl subunits by classic enzymes as well as iterative and multimodular enzymes that share mechanistic features with the fatty acid synthases. They comprise a large number of secondary metabolites and natural products from animal, plant, bacterial, fungal and marine sources, and have great structural diversity. Many polyketides are cyclic molecules whose backbones are often further modified by glycosylation, methylation, hydroxylation, oxidation, or other processes.

According to the disclosure, lipids and lipid-like materials may be cationic, anionic or neutral. Neutral lipids or lipid-like materials exist in an uncharged or neutral zwitterionic form at a selected pH.

Cationic or Cationically Ionizable Lipids or Lipid-Like Materials

The nucleic acid particles described herein may comprise at least one cationic or cationically ionizable lipid or lipid-like material as particle forming agent. Cationic or cationically ionizable lipids or lipid-like materials contemplated for use herein include any cationic or cationically ionizable lipids or lipid-like materials which are able to electrostatically bind nucleic acid. In one embodiment, cationic or cationically ionizable lipids or lipid-like materials contemplated for use herein can be associated with nucleic acid, e.g. by forming complexes with the nucleic acid or forming vesicles in which the nucleic acid is enclosed or encapsulated.

As used herein, a "cationic lipid" or "cationic lipid-like material" refers to a lipid or lipid-like material having a net positive charge. Cationic lipids or lipid-like materials bind negatively charged nucleic acid by electrostatic interaction. Generally, cationic lipids possess a lipophilic moiety, such as a sterol, an acyl chain, a diacyl or more acyl chains, and the head group of the lipid typically carries the positive charge.

In certain embodiments, a cationic lipid or lipid-like material has a net positive charge only at certain pH, in particular acidic pH, while it has preferably no net positive charge, preferably has no charge, i.e., it is neutral, at a different, preferably higher pH such as physiological pH. This ionizable behavior is thought to enhance efficacy through helping with endosomal escape and reducing toxicity as compared with particles that remain cationic at physiological pH.

For purposes of the present disclosure, such "cationically ionizable" lipids or lipid-like materials are comprised by the term "cationic lipid or lipid-like material" unless contradicted by the circumstances.

In one embodiment, the cationic or cationically ionizable lipid or lipid-like material comprises a head group which includes at least one nitrogen atom (N) which is positive charged or capable of being protonated.

Examples of cationic lipids include, but are not limited to 1,2-dioleoyl-3-trimethylammonium propane (DOTAP); N,N-dimethyl-2,3-dioleyloxypropylamine (DODMA), 1,2-di-O-octadecenyl-3-trimethylammonium propane (DOTMA), 3-(N—(N',N'-dimethylaminoethane)-carbamoyl)cholesterol (DC-Chol), dimethyldioctadecylammonium (DDAB); 1,2-dioleoyl-3-dimethylammonium-propane (DODAP); 1,2-diacyloxy-3-dimethylammonium propanes; 1,2-dialkyloxy-3-dimethylammonium propanes; dioctadecyldimethyl ammonium chloride (DODAC), 1,2-distearyloxy-N,N-dimethyl-3-aminopropane (DSDMA), 2,3-di(tetradecoxy)propyl-(2-hydroxyethyl)-dimethylazanium (DMRIE), 1,2-dimyristoyl-sn-glycero-3-ethylphosphocholine (DMEPC), 1,2-dimyristoyl-3-trimethylammonium propane (DMTAP), 1,2-dioleyloxypropyl-3-dimethyl-hydroxyethyl ammonium bromide (DORIE), and 2,3-dioleoyloxy-N-[2(spermine carboxamide)ethyl]-N,N-dimethyl-1-propanamium trifluoroacetate (DOSPA), 1,2-dilinoleyloxy-N,N-dimethylaminopropane (DLinDMA), 1,2-dilinolenyloxy-N,N-dimethylaminopropane (DLenDMA), dioctadecylamidoglycyl spermine (DOGS), 3-dimethylamino-2-(cholest-5-en-3-beta-oxybutan-4-oxy)-1-(cis,cis-9,12-oc-tadecadienoxy)propane (CLinDMA), 2-[5'-(cholest-5-en-3-beta-oxy)-3'-oxapentoxy)-3-dimethyl-1-(cis,cis-9',12'-octadecadienoxy)propane (CpLinDMA), N,N-dimethyl-3,4-dioleyloxybenzylamine (DMOBA), 1,2-N,N'-dioleylcarbamyl-3-dimethylaminopropane (DOcarbDAP), 2,3-Dilinoleoyloxy-N,N-dimethylpropylamine (DLinDAP), 1,2-N,N'-Dilinoleylcarbamyl-3-dimethylaminopropane (DLincarbDAP), 1,2-Dilinoleoylcarbamyl-3-dimethylaminopropane (DLinCDAP), 2,2-dilinoleyl-4-dimethylaminomethyl-[1,3]-dioxolane (DLin-K-DMA), 2,2-dilinoleyl-4-dimethylaminoethyl-[1,3]-dioxolane (DLin-K-XTC2-DMA), 2,2-dilinoleyl-4-(2-dimethylaminoethyl)-[1,3]-dioxolane (DLin-KC2-DMA), heptatriaconta-6,9,28,31-tetraen-19-yl-4-(dimethylamino)butanoate (DLin-MC3-DMA), N-(2-Hydroxyethyl)-N,N-dimethyl-2,3-bis(tetradecyloxy)-1-propanaminium bromide (DMRIE), (±)-N-(3-aminopropyl)-N,N-dimethyl-2,3-bis(cis-9-tetradecenyloxy)-1-propanaminium bromide (GAP-DMORIE), (±)-N-(3-aminopropyl)-N,N-dimethyl-2,3-bis(dodecyloxy)-1-propanaminium bromide (GAP-DLRIE), (±)-N-(3-aminopropyl)-N,N-dimethyl-2,3-bis(tetradecyloxy)-1-propanaminium bromide (GAP-DMRIE), N-(2 Aminoethyl)-N,N-dimethyl-2,3-bis(tetradecyloxy)-1-propanaminium bromide (βAE-DMRIE), N-(4-carboxybenzyl)-N,N-dimethyl-2,3-bis(oleoyloxy)propan-1-aminium (DOBAQ), 2-(8-[(3β)-cholest-5-en-3-yloxy]octyloxy)-N,N-dimethyl-3-[(9Z,12Z)-octadeca-9,12-dien-1-yloxy]propan-1-amine (Octyl-CLinDMA), 1,2-dimyristoyl-3-dimethylammonium-propane (DMDAP), 1,2-dipalmitoyl-3-dimethylammonium-propane (DPDAP), N1-[2-((1 S)-1-[(3-aminopropyl)amino]-4-[di(3-amino-propyl)amino] butylcarboxamido)ethyl]-3,4-di[oleyloxy]-benzamide (MVL5), 1,2-dioleoyl-sn-glycero-3-ethylphosphocholine (DOEPC), 2,3-bis(dodecyloxy)-N-(2-hydroxyethyl)-N,N-dimethylpropan-1-ammonium bromide (DLRIE), N-(2-aminoethyl)-N,N-dimethyl-2,3-bis(tetradecyloxy)propan-1-aminium bromide (DMORIE), di((Z)-non-2-en-1-yl) 8,8'-((((2(dimethylamino)ethyl)thio)carbonyl)azanediyl) dioctanoate (ATX), N,N-dimethyl-2,3-bis(dodecyloxy) propan-1-amine (DLDMA), N,N-dimethyl-2,3-bis (tetradecyloxy)propan-1-amine (DMDMA), Di((Z)-non-2-en-1-yl)-9-((4-(dimethylaminobutanoyl)oxy) heptadecanedioate (L319), N-Dodecyl-3-((2-dodecylcarbamoyl-ethyl)-2-[(2-dodecylcarbamoyl-ethyl)-2-(2-dodecylcarbamoyl-ethyl)-[2-(2-dodecylcarbamoyl-ethylamino)-ethyl]-amino-ethylamino)propionamide (lipidoid 98$N_{12}$-5), 1-[2-[bis(2-hydroxydodecyl)amino] ethyl-[2-[4-[2-[bis(2 hydroxydodecyl)amino]ethyl]piperazin-1-yl]ethyl]amino]dodecan-2-ol (lipidoid C12-200). Preferred are DOTAP, DODMA, DOTMA, DODAC, and DOSPA. In specific embodiments, the at least one cationic lipid is DOTAP.

In some embodiments, the cationic lipid may comprise from about 10 mol % to about 100 mol %, about 20 mol % to about 100 mol %, about 30 mol % to about 100 mol %, about 40 mol % to about 100 mol %, or about 50 mol % to about 100 mol % of the total lipid present in the particle.

Additional Lipids or Lipid-Like Materials

Particles described herein may also comprise lipids or lipid-like materials other than cationic or cationically ionizable lipids or lipid-like materials, i.e., non-cationic lipids or lipid-like materials (including non-cationically ionizable lipids or lipid-like materials). Collectively, anionic and neutral lipids or lipid-like materials are referred to herein as non-cationic lipids or lipid-like materials. Optimizing the formulation of nucleic acid particles by addition of other hydrophobic moieties, such as cholesterol and lipids, in addition to an ionizable/cationic lipid or lipid-like material may enhance particle stability and efficacy of nucleic acid delivery.

An additional lipid or lipid-like material may be incorporated which may or may not affect the overall charge of the nucleic acid particles. In certain embodiments, the additional lipid or lipid-like material is a non-cationic lipid or lipid-like material. The non-cationic lipid may comprise, e.g., one or more anionic lipids and/or neutral lipids. As used herein, a "neutral lipid" refers to any of a number of lipid species that exist either in an uncharged or neutral zwitterionic form at a selected pH. In preferred embodiments, the additional lipid comprises one of the following neutral lipid components: (1) a phospholipid, (2) cholesterol or a derivative thereof; or (3) a mixture of a phospholipid and cholesterol or a derivative thereof. Examples of cholesterol derivatives include, but are not limited to, cholestanol, cholestanone, cholestenone, coprostanol, cholesteryl-2'-hydroxyethyl ether, cholesteryl-4'-hydroxybutyl ether, tocopherol and derivatives thereof, and mixtures thereof.

Specific phospholipids that can be used include, but are not limited to, phosphatidylcholines, phosphatidylethanolamines, phosphatidylglycerols, phosphatidic acids, phosphatidylserines or sphingomyelin. Such phospholipids include in particular diacylphosphatidylcholines, such as distearoylphosphatidylcholine (DSPC), dioleoylphosphatidylcholine (DOPC), dimyristoylphosphatidylcholine (DMPC), dipentadecanoylphosphatidylcholine, dilauroylphosphatidylcholine, dipalmitoylphosphatidylcholine (DPPC), diarachidoylphosphatidylcholine (DAPC), dibehenoylphosphatidylcholine (DBPC), ditricosanoylphosphatidylcholine (DTPC), dilignoceroylphatidylcholine (DLPC), palmitoyloleoyl-phosphatidylcholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC) and phosphatidylethanolamines, in particular diacylphosphatidylethanolamines, such as dioleoylphosphatidylethanolamine (DOPE), distearoyl-phosphatidylethanolamine (DSPE), dipalmitoyl-phosphatidylethanolamine (DPPE), dimyristoylphosphatidylethanolamine (DMPE), dilauroyl-phosphatidylethanolamine (DLPE), diphytanoyl-phosphatidylethanolamine (DPyPE), and further phosphatidylethanolamine lipids with different hydrophobic chains.

In certain preferred embodiments, the additional lipid is DSPC or DSPC and cholesterol.

In certain embodiments, the nucleic acid particles include both a cationic lipid and an additional lipid. In an exemplary embodiment, the cationic lipid is DOTAP and the additional lipid is DSPC or DSPC and cholesterol.

Without wishing to be bound by theory, the amount of the at least one cationic lipid compared to the amount of the at least one additional lipid may affect important nucleic acid particle characteristics, such as charge, particle size, stability, tissue selectivity, and bioactivity of the nucleic acid. Accordingly, in some embodiments, the molar ratio of the at least one cationic lipid to the at least one additional lipid is from about 10:0 to about 1:9, about 4:1 to about 1:2, or about 3:1 to about 1:1.

In some embodiments, the non-cationic lipid, in particular neutral lipid, (e.g., one or more phospholipids and/or cholesterol) may comprise from about 0 mol % to about 90 mol %, from about 0 mol % to about 80 mol %, from about 0 mol % to about 70 mol %, from about 0 mol % to about 60 mol %, or from about 0 mol % to about 50 mol %, of the total lipid present in the particle.

RNA Targeting

It is particularly preferred according to the invention that the peptides, proteins or polypeptides described herein, in particular the vaccine antigens and/or immunostimulants, are administered in the form of RNA encoding the peptides, proteins or polypeptides described herein. In one embodiment, different peptides, proteins or polypeptides described herein are encoded by different RNA molecules.

In one embodiment, the RNA is formulated in a delivery vehicle. In one embodiment, the delivery vehicle comprises particles. In one embodiment, the delivery vehicle comprises at least one lipid. In one embodiment, the at least one lipid comprises at least one cationic lipid. In one embodiment, the lipid forms a complex with and/or encapsulates the RNA. In one embodiment, the lipid is comprised in a vesicle encapsulating the RNA. In one embodiment, the RNA is formulated in liposomes.

According to the disclosure, after administration of the RNA described herein, at least a portion of the RNA is delivered to a target cell. In one embodiment, at least a portion of the RNA is delivered to the cytosol of the target cell. In one embodiment, the RNA is translated by the target cell to produce the encoded peptide or protein.

Some aspects of the disclosure involve the targeted delivery of the RNA disclosed herein (e.g., RNA encoding vaccine antigens and/or immunostimulants).

In one embodiment, the disclosure involves targeting the lymphatic system, in particular secondary lymphoid organs, more specifically spleen. Targeting the lymphatic system, in particular secondary lymphoid organs, more specifically spleen is in particular preferred if the RNA administered is RNA encoding vaccine antigen.

In one embodiment, the target cell is a spleen cell. In one embodiment, the target cell is an antigen presenting cell such as a professional antigen presenting cell in the spleen. In one embodiment, the target cell is a dendritic cell in the spleen.

The "lymphatic system" is part of the circulatory system and an important part of the immune system, comprising a network of lymphatic vessels that carry lymph. The lymphatic system consists of lymphatic organs, a conducting network of lymphatic vessels, and the circulating lymph. The primary or central lymphoid organs generate lymphocytes from immature progenitor cells. The thymus and the bone marrow constitute the primary lymphoid organs. Secondary or peripheral lymphoid organs, which include lymph nodes and the spleen, maintain mature naïve lymphocytes and initiate an adaptive immune response.

RNA may be delivered to spleen by so-called lipoplex formulations, in which the RNA is bound to liposomes comprising a cationic lipid and optionally an additional or helper lipid to form injectable nanoparticle formulations. The liposomes may be obtained by injecting a solution of the lipids in ethanol into water or a suitable aqueous phase. RNA lipoplex particles may be prepared by mixing the liposomes with RNA. Spleen targeting RNA lipoplex particles are described in WO 2013/143683, herein incorporated by reference. It has been found that RNA lipoplex particles having a net negative charge may be used to preferentially target spleen tissue or spleen cells such as antigen-presenting cells, in particular dendritic cells. Accordingly, following administration of the RNA lipoplex particles, RNA accumulation and/or RNA expression in the spleen occurs. Thus, RNA lipoplex particles of the disclosure may be used for expressing RNA in the spleen. In an embodiment, after administration of the RNA lipoplex particles, no or essentially no RNA accumulation and/or RNA expression in the lung and/or liver occurs. In one embodiment, after administration of the RNA lipoplex particles, RNA accumulation and/or RNA expression in antigen presenting cells, such as professional antigen presenting cells in the spleen occurs. Thus, RNA lipoplex particles of the disclosure may be used for expressing RNA in such antigen presenting cells. In one embodiment, the antigen presenting cells are dendritic cells and/or macrophages.

In the context of the present disclosure, the term "RNA lipoplex particle" relates to a particle that contains lipid, in particular cationic lipid, and RNA. Electrostatic interactions between positively charged liposomes and negatively charged RNA results in complexation and spontaneous formation of RNA lipoplex particles. Positively charged liposomes may be generally synthesized using a cationic lipid, such as DOTMA, and additional lipids, such as DOPE. In one embodiment, a RNA lipoplex particle is a nanoparticle.

In certain embodiments, the RNA lipoplex particles include both a cationic lipid and an additional lipid. In an exemplary embodiment, the cationic lipid is DOTMA and the additional lipid is DOPE.

In some embodiments, the molar ratio of the at least one cationic lipid to the at least one additional lipid is from about 10:0 to about 1:9, about 4:1 to about 1:2, or about 3:1 to about 1:1. In specific embodiments, the molar ratio may be about 3:1, about 2.75:1, about 2.5:1, about 2.25:1, about 2:1, about 1.75:1, about 1.5:1, about 1.25:1, or about 1:1. In an exemplary embodiment, the molar ratio of the at least one cationic lipid to the at least one additional lipid is about 2:1.

RNA lipoplex particles described herein have an average diameter that in one embodiment ranges from about 200 nm to about 1000 nm, from about 200 nm to about 800 nm, from about 250 to about 700 nm, from about 400 to about 600 nm, from about 300 nm to about 500 nm, or from about 350 nm to about 400 nm. In specific embodiments, the RNA lipoplex particles have an average diameter of about 200 nm, about 225 nm, about 250 nm, about 275 nm, about 300 nm, about 325 nm, about 350 nm, about 375 nm, about 400 nm, about 425 nm, about 450 nm, about 475 nm, about 500 nm, about 525 nm, about 550 nm, about 575 nm, about 600 nm, about 625 nm, about 650 nm, about 700 nm, about 725 nm, about 750 nm, about 775 nm, about 800 nm, about 825 nm, about 850 nm, about 875 nm, about 900 nm, about 925 nm, about 950 nm, about 975 nm, or about 1000 nm. In an embodiment, the RNA lipoplex particles have an average diameter that ranges from about 250 nm to about 700 nm. In another embodiment, the RNA lipoplex particles have an average diameter that ranges from about 300 nm to about 500 nm. In an exemplary embodiment, the RNA lipoplex particles have an average diameter of about 400 nm.

The electric charge of the RNA lipoplex particles of the present disclosure is the sum of the electric charges present in the at least one cationic lipid and the electric charges present in the RNA. The charge ratio is the ratio of the positive charges present in the at least one cationic lipid to the negative charges present in the RNA. The charge ratio of the positive charges present in the at least one cationic lipid to the negative charges present in the RNA is calculated by the following equation: charge ratio=[(cationic lipid concentration (mol))*(the total number of positive charges in the cationic lipid)]/[(RNA concentration (mol))*(the total number of negative charges in RNA)].

The spleen targeting RNA lipoplex particles described herein at physiological pH preferably have a net negative charge such as a charge ratio of positive charges to negative charges from about 1.9:2 to about 1:2. In specific embodiments, the charge ratio of positive charges to negative charges in the RNA lipoplex particles at physiological pH is about 1.9:2.0, about 1.8:2.0, about 1.7:2.0, about 1.6:2.0, about 1.5:2.0, about 1.4:2.0, about 1.3:2.0, about 1.2:2.0, about 1.1:2.0, or about 1:2.0.

Immunostimulants may be provided to a subject by administering to the subject RNA encoding an immunostimulant in a formulation for preferential delivery of RNA to liver or liver tissue. The delivery of RNA to such target organ or tissue is preferred, in particular, if it is desired to express large amounts of the immunostimulant and/or if systemic presence of the immunostimulant, in particular in significant amounts, is desired or required.

RNA delivery systems have an inherent preference to the liver. This pertains to lipid-based particles, cationic and neutral nanoparticles, in particular lipid nanoparticles such as liposomes, nanomicelles and lipophilic ligands in bioconjugates. Liver accumulation is caused by the discontinuous nature of the hepatic vasculature or the lipid metabolism (liposomes and lipid or cholesterol conjugates).

For in vivo delivery of RNA to the liver, a drug delivery system may be used to transport the RNA into the liver by preventing its degradation. For example, polyplex nanomicelles consisting of a poly(ethylene glycol) (PEG)-coated surface and an mRNA-containing core is a useful system because the nanomicelles provide excellent in vivo stability of the RNA, under physiological conditions. Furthermore, the stealth property provided by the polyplex nanomicelle surface, composed of dense PEG palisades, effectively evades host immune defenses.

Examples of suitable immunostimulants for targeting liver are cytokines involved in T cell proliferation and/or maintenance. Examples of suitable cytokines include IL2 or IL7, fragments and variants thereof, and fusion proteins of these cytokines, fragments and variants, such as extended-PK cytokines.

In another embodiment, RNA encoding an immunostimulant may be administered in a formulation for preferential delivery of RNA to the lymphatic system, in particular secondary lymphoid organs, more specifically spleen. The delivery of an immunostimulant to such target tissue is preferred, in particular, if presence of the immunostimulant in this organ or tissue is desired (e.g., for inducing an immune response, in particular in case immunostimulants such as cytokines are required during T-cell priming or for activation of resident immune cells), while it is not desired that the immunostimulant is present systemically, in particular in significant amounts (e.g., because the immunostimulant has systemic toxicity).

Examples of suitable immunostimulants are cytokines involved in T cell priming. Examples of suitable cytokines include IL12, IL15, IFN-α, or IFN-β, fragments and variants thereof, and fusion proteins of these cytokines, fragments and variants, such as extended-PK cytokines.

Chemotherapy

In certain embodiments, additional treatments may be administered to a patient in combination with the treatments described herein. Such additional treatments includes classical cancer therapy, e.g., radiation therapy, surgery, hyperthermia therapy and/or chemotherapy.

Chemotherapy is a type of cancer treatment that uses one or more anti-cancer drugs (chemotherapeutic agents), usually as part of a standardized chemotherapy regimen. The term chemotherapy has come to connote non-specific usage of intracellular poisons to inhibit mitosis. The connotation excludes more selective agents that block extracellular signals (signal transduction). The development of therapies with specific molecular or genetic targets, which inhibit growth-promoting signals from classic endocrine hormones (primarily estrogens for breast cancer and androgens for prostate cancer) are now called hormonal therapies. By contrast, other inhibitions of growth-signals like those associated with receptor tyrosine kinases are referred to as targeted therapy.

Importantly, the use of drugs (whether chemotherapy, hormonal therapy or targeted therapy) constitutes systemic therapy for cancer in that they are introduced into the blood stream and are therefore in principle able to address cancer at any anatomic location in the body. Systemic therapy is often used in conjunction with other modalities that constitute local therapy (i.e. treatments whose efficacy is confined to the anatomic area where they are applied) for cancer such as radiation therapy, surgery or hyperthermia therapy.

Traditional chemotherapeutic agents are cytotoxic by means of interfering with cell division (mitosis) but cancer cells vary widely in their susceptibility to these agents. To a large extent, chemotherapy can be thought of as a way to damage or stress cells, which may then lead to cell death if apoptosis is initiated.

Chemotherapeutic agents include alkylating agents, antimetabolites, anti-microtubule agents, topoisomerase inhibitors, and cytotoxic antibiotics.

Alkylating agents have the ability to alkylate many molecules, including proteins, RNA and DNA. The subtypes of alkylating agents are the nitrogen mustards, nitrosoureas, tetrazines, aziridines, cisplatins and derivatives, and non-classical alkylating agents. Nitrogen mustards include mechlorethamine, cyclophosphamide, melphalan, chlorambucil, ifosfamide and busulfan. Nitrosoureas include N-Nitroso-N-methylurea (MNU), carmustine (BCNU), lomustine (CCNU) and semustine (MeCCNU), fotemustine and streptozotocin. Tetrazines include dacarbazine, mitozolomide and temozolomide. Aziridines include thiotepa, mytomycin and diaziquone (AZQ). Cisplatin and derivatives include cisplatin, carboplatin and oxaliplatin. They impair cell function by forming covalent bonds with the amino, carboxyl, sulfhydryl, and phosphate groups in biologically important molecules. Non-classical alkylating agents include procarbazine and hexamethylmelamine. In one particularly preferred embodiment, the alkylating agent is cyclophosphamide.

Anti-metabolites are a group of molecules that impede DNA and RNA synthesis. Many of them have a similar structure to the building blocks of DNA and RNA. Anti-metabolites resemble either nucleobases or nucleosides, but have altered chemical groups. These drugs exert their effect by either blocking the enzymes required for DNA synthesis or becoming incorporated into DNA or RNA. Subtypes of the anti-metabolites are the anti-folates, fluoropyrimidines, deoxynucleoside analogues and thiopurines. The anti-folates include methotrexate and pemetrexed. The fluoropyrimidines include fluorouracil and capecitabine. The deoxynucleoside analogues include cytarabine, gemcitabine, decitabine, azacitidine, fludarabine, nelarabine, cladribine, clofarabine, and pentostatin. The thiopurines include thioguanine and mercaptopurine.

Anti-microtubule agents block cell division by preventing microtubule function. The vinca alkaloids prevent the formation of the microtubules, whereas the taxanes prevent the microtubule disassembly. Vinca alkaloids include vinorelbine, vindesine, and vinflunine. Taxanes include docetaxel (Taxotere) and paclitaxel (Taxol).

Topoisomerase inhibitors are drugs that affect the activity of two enzymes: topoisomerase I and topoisomerase II and include irinotecan, topotecan, camptothecin, etoposide, doxorubicin, mitoxantrone, teniposide, novobiocin, merbarone, and aclarubicin.

The cytotoxic antibiotics are a varied group of drugs that have various mechanisms of action. The common theme that they share in their chemotherapy indication is that they interrupt cell division. The most important subgroup is the anthracyclines (e.g., doxorubicin, daunorubicin, epirubicin, idarubicin pirarubicin, and aclarubicin) and the bleomycins; other prominent examples include mitomycin C, mitoxantrone, and actinomycin.

In one embodiment, prior to administration of immune effector cells, a lymphodepleting treatment may be applied, e.g., by administering cyclophosphamide and fludarabine. Such treatment may increase cell persistence and the incidence and duration of clinical responses.

Immune Checkpoint Inhibitors

In certain embodiments, immune checkpoint inhibitors are used in combination with other therapeutic agents described herein.

As used herein, "immune checkpoint" refers to co-stimulatory and inhibitory signals that regulate the amplitude and quality of T cell receptor recognition of an antigen. In certain embodiments, the immune checkpoint is an inhibitory signal. In certain embodiments, the inhibitory signal is the interaction between PD-1 and PD-L1. In certain embodiments, the inhibitory signal is the interaction between CTLA-4 and CD80 or CD86 to displace CD28 binding. In certain embodiments the inhibitory signal is the interaction between LAG3 and MHC class II molecules. In certain embodiments, the inhibitory signal is the interaction between TIM3 and galectin 9.

As used herein, "immune checkpoint inhibitor" refers to a molecule that totally or partially reduces, inhibits, interferes with or modulates one or more checkpoint proteins. In certain embodiments, the immune checkpoint inhibitor prevents inhibitory signals associated with the immune checkpoint. In certain embodiments, the immune checkpoint inhibitor is an antibody, or fragment thereof that disrupts inhibitory signaling associated with the immune checkpoint. In certain embodiments, the immune checkpoint inhibitor is a small molecule that disrupts inhibitory signaling. In certain embodiments, the immune checkpoint inhibitor is an antibody, fragment thereof, or antibody mimic, that prevents the interaction between checkpoint blocker proteins, e.g., an antibody, or fragment thereof, that prevents the interaction between PD-1 and PD-L1. In certain embodiments, the immune checkpoint inhibitor is an antibody, or fragment thereof, that prevents the interaction between CTLA-4 and CD80 or CD86. In certain embodiments, the immune checkpoint inhibitor is an antibody, or fragment thereof, that prevents the interaction between LAG3 and its ligands, or TIM-3 and its ligands. The checkpoint inhibitor may also be in the form of the soluble form of the molecules (or variants thereof) themselves, e.g., a soluble PD-L1 or PD-L1 fusion.

The "Programmed Death-1 (PD-1)" receptor refers to an immuno-inhibitory receptor belonging to the CD28 family. PD-1 is expressed predominantly on previously activated T cells in vivo, and binds to two ligands, PD-L1 and PD-L2. The term "PD-1" as used herein includes human PD-1 (hPD-1), variants, isoforms, and species homologs of hPD-1, and analogs having at least one common epitope with hPD-1.

"Programmed Death Ligand-1 (PD-L1)" is one of two cell surface glycoprotein ligands for PD-1 (the other being PD-L2) that downregulates T cell activation and cytokine secretion upon binding to PD-1. The term "PD-L1" as used herein includes human PD-L1 (hPD-L1), variants, isoforms, and species homologs of hPD-L1, and analogs having at least one common epitope with hPD-L1.

"Cytotoxic T Lymphocyte Associated Antigen-4 (CTLA-4)" is a T cell surface molecule and is a member of the immunoglobulin superfamily. This protein downregulates the immune system by binding to CD80 and CD86. The term "CTLA-4" as used herein includes human CTLA-4 (hCTLA-4), variants, isoforms, and species homologs of hCTLA-4, and analogs having at least one common epitope with hCTLA-4.

"Lymphocyte Activation Gene-3 (LAG3)" is an inhibitory receptor associated with inhibition of lymphocyte activity by binding to MHC class II molecules. This receptor enhances the function of Treg cells and inhibits CD8+ effector T cell function. The term "LAG3" as used herein includes human LAG3 (hLAG3), variants, isoforms, and species homologs of hLAG3, and analogs having at least one common epitope.

"T Cell Membrane Protein-3 (TIM3)" is an inhibitory receptor involved in the inhibition of lymphocyte activity by inhibition of TH1 cell responses. Its ligand is galectin 9, which is upregulated in various types of cancers. The term "TIM3" as used herein includes human TIM3 (hTIM3), variants, isoforms, and species homologs of hTIM3, and analogs having at least one common epitope.

The "B7 family" refers to inhibitory ligands with undefined receptors. The B7 family encompasses B7-H3 and B7-H4, both upregulated on tumor cells and tumor infiltrating cells.

In certain embodiments, the immune checkpoint inhibitor suitable for use in the methods disclosed herein, is an antagonist of inhibitory signals, e.g., an antibody which targets, for example, PD-1, PD-L1, CTLA-4, LAG3, B7-H3, B7-H4, or TIM3. These ligands and receptors are reviewed in Pardoll, D., Nature. 12: 252-264, 2012.

In certain embodiments, the immune checkpoint inhibitor is an antibody or an antigen-binding portion thereof, that disrupts or inhibits signaling from an inhibitory immunoregulator. In certain embodiments, the immune checkpoint inhibitor is a small molecule that disrupts or inhibits signaling from an inhibitory immunoregulator.

In certain embodiments, the inhibitory immunoregulator is a component of the PD-1/PD-L1 signaling pathway. Accordingly, certain embodiments of the disclosure provide for administering to a subject an antibody or an antigen-binding portion thereof that disrupts the interaction between the PD-1 receptor and its ligand, PD-L1. Antibodies which bind to PD-1 and disrupt the interaction between the PD-1 and its ligand, PD-L1, are known in the art. In certain embodiments, the antibody or antigen-binding portion thereof binds specifically to PD-1. In certain embodiments, the antibody or antigen-binding portion thereof binds specifically to PD-L1 and inhibits its interaction with PD-1, thereby increasing immune activity.

In certain embodiments, the inhibitory immunoregulator is a component of the CTLA4 signaling pathway. Accordingly, certain embodiments of the disclosure provide for administering to a subject an antibody or an antigen-binding portion thereof that targets CTLA4 and disrupts its interaction with CD80 and CD86.

In certain embodiments, the inhibitory immunoregulator is a component of the LAG3 (lymphocyte activation gene 3) signaling pathway. Accordingly, certain embodiments of the disclosure provide for administering to a subject an antibody or an antigen-binding portion thereof that targets LAG3 and disrupts its interaction with MHC class II molecules.

In certain embodiments, the inhibitory immunoregulator is a component of the B7 family signaling pathway. In certain embodiments, the B7 family members are B7-H3 and B7-H4. Accordingly, certain embodiments of the disclosure provide for administering to a subject an antibody or an antigen-binding portion thereof that targets B7-H3 or H4. The B7 family does not have any defined receptors but these ligands are upregulated on tumor cells or tumor-infiltrating cells. Preclinical mouse models have shown that blockade of these ligands can enhance anti-tumor immunity.

In certain embodiments, the inhibitory immunoregulator is a component of the TIM3 (T cell membrane protein 3) signaling pathway. Accordingly, certain embodiments of the disclosure provide for administering to a subject an antibody or an antigen-binding portion thereof that targets TIM3 and disrupts its interaction with galectin 9.

It will be understood by one of ordinary skill in the art that other immune checkpoint targets can also be targeted by antagonists or antibodies, provided that the targeting results in the stimulation of an immune response such as an anti-tumor immune response as reflected in, e.g., an increase in T cell proliferation, enhanced T cell activation, and/or increased cytokine production (e.g., IFN-γ, IL2).

Pharmaceutical Compositions

The agents described herein may be administered in pharmaceutical compositions or medicaments and may be administered in the form of any suitable pharmaceutical composition.

In one embodiment of all aspects of the invention, the components described herein such as RNA encoding an antigen or RNA encoding an immunostimulant either together or separate from each other may be administered in a pharmaceutical composition which may comprise a pharmaceutically acceptable carrier and may optionally comprise one or more adjuvants, stabilizers etc. In one embodiment, the pharmaceutical composition is for therapeutic or prophylactic treatments, e.g., for use in treating or preventing a disease involving an antigen such as a cancer disease such as those described herein.

The term "pharmaceutical composition" relates to a formulation comprising a therapeutically effective agent, preferably together with pharmaceutically acceptable carriers, diluents and/or excipients. Said pharmaceutical composition is useful for treating, preventing, or reducing the severity of a disease or disorder by administration of said pharmaceutical composition to a subject. A pharmaceutical composition is also known in the art as a pharmaceutical formulation.

The pharmaceutical compositions of the present disclosure may comprise one or more adjuvants or may be administered with one or more adjuvants. The term "adjuvant" relates to a compound which prolongs, enhances or accelerates an immune response. Adjuvants comprise a heterogeneous group of compounds such as oil emulsions (e.g., Freund's adjuvants), mineral compounds (such as alum), bacterial products (such as *Bordetella pertussis* toxin), or immune-stimulating complexes. Examples of adjuvants include, without limitation, LPS, GP96, CpG oligodeoxynucleotides, growth factors, and cytokines, such as monokines, lymphokines, interleukins, chemokines. The cytokines may be IL1, IL2, IL3, IL4, IL5, IL6, IL7, IL8, IL9, IL10, IL12, IFNα, IFNγ, GM-CSF, LT-a. Further known adjuvants are aluminium hydroxide, Freund's adjuvant or oil such as Montanide® ISA51. Other suitable adjuvants for use in the present disclosure include lipopeptides, such as Pam3Cys.

The pharmaceutical compositions according to the present disclosure are generally applied in a "pharmaceutically effective amount" and in "a pharmaceutically acceptable preparation".

The term "pharmaceutically acceptable" refers to the non-toxicity of a material which does not interact with the action of the active component of the pharmaceutical composition.

The term "pharmaceutically effective amount" or "therapeutically effective amount" refers to the amount which achieves a desired reaction or a desired effect alone or together with further doses. In the case of the treatment of a particular disease, the desired reaction preferably relates to inhibition of the course of the disease. This comprises slowing down the progress of the disease and, in particular, interrupting or reversing the progress of the disease. The desired reaction in a treatment of a disease may also be delay of the onset or a prevention of the onset of said disease or said condition. An effective amount of the compositions described herein will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses administered of the compositions described herein may depend on various of such parameters. In the case that a reaction in a patient is insufficient with an initial dose, higher doses (or effectively higher doses achieved by a different, more localized route of administration) may be used.

The pharmaceutical compositions of the present disclosure may contain salts, buffers, preservatives, and optionally other therapeutic agents. In one embodiment, the pharmaceutical compositions of the present disclosure comprise one or more pharmaceutically acceptable carriers, diluents and/or excipients.

Suitable preservatives for use in the pharmaceutical compositions of the present disclosure include, without limitation, benzalkonium chloride, chlorobutanol, paraben and thimerosal.

The term "excipient" as used herein refers to a substance which may be present in a pharmaceutical composition of the present disclosure but is not an active ingredient. Examples of excipients, include without limitation, carriers, binders, diluents, lubricants, thickeners, surface active agents, preservatives, stabilizers, emulsifiers, buffers, flavoring agents, or colorants.

The term "diluent" relates a diluting and/or thinning agent. Moreover, the term "diluent" includes any one or more of fluid, liquid or solid suspension and/or mixing media. Examples of suitable diluents include ethanol, glycerol and water.

The term "carrier" refers to a component which may be natural, synthetic, organic, inorganic in which the active component is combined in order to facilitate, enhance or enable administration of the pharmaceutical composition. A carrier as used herein may be one or more compatible solid or liquid fillers, diluents or encapsulating substances, which are suitable for administration to subject. Suitable carrier include, without limitation, sterile water, Ringer, Ringer lactate, sterile sodium chloride solution, isotonic saline, polyalkylene glycols, hydrogenated naphthalenes and, in particular, biocompatible lactide polymers, lactide/glycolide copolymers or polyoxyethylene/polyoxy-propylene copolymers. In one embodiment, the pharmaceutical composition of the present disclosure includes isotonic saline.

Pharmaceutically acceptable carriers, excipients or diluents for therapeutic use are well known in the pharmaceutical art, and are described, for example, in Remington's Pharmaceutical Sciences, Mack Publishing Co. (A. R Gennaro edit. 1985).

Pharmaceutical carriers, excipients or diluents can be selected with regard to the intended route of administration and standard pharmaceutical practice.

In one embodiment, pharmaceutical compositions described herein may be administered intravenously, intraarterially, subcutaneously, intradermally or intramuscularly. In certain embodiments, the pharmaceutical composition is formulated for local administration or systemic administration. Systemic administration may include enteral administration, which involves absorption through the gastrointestinal tract, or parenteral administration. As used herein, "parenteral administration" refers to the administration in any manner other than through the gastrointestinal tract, such as by intravenous injection. In a preferred embodiment, the pharmaceutical compositions is formulated for systemic administration. In another preferred embodiment, the systemic administration is by intravenous administration. In one embodiment of all aspects of the invention, RNA encoding an antigen or RNA encoding an immunostimulant is administered systemically.

The term "co-administering" as used herein means a process whereby different compounds or compositions (e.g., RNA encoding an antigen or RNA encoding an immunostimulant) are administered to the same patient. The different compounds or compositions may be administered simultaneously, at essentially the same time, or sequentially.

Treatments

The agents, compositions and methods described herein can be used to treat a subject with a disease, e.g., a disease characterized by the presence of diseased cells expressing an antigen. Particularly preferred diseases are cancer diseases. For example, if the antigen is derived from a virus, the agents, compositions and methods may be useful in the treatment of a viral disease caused by said virus. If the antigen is derived from a tumor antigen, the agents, compositions and methods may be useful in the treatment of a cancer disease wherein cancer cells express said tumor antigen.

The term "disease" refers to an abnormal condition that affects the body of an individual. A disease is often construed as a medical condition associated with specific symptoms and signs. A disease may be caused by factors originally from an external source, such as infectious disease, or it may be caused by internal dysfunctions, such as autoimmune diseases. In humans, "disease" is often used more broadly to refer to any condition that causes pain, dysfunction, distress, social problems, or death to the individual afflicted, or similar problems for those in contact with the individual. In this broader sense, it sometimes includes injuries, disabilities, disorders, syndromes, infections, isolated symptoms, deviant behaviors, and atypical variations of structure and function, while in other contexts and for other purposes these may be considered distinguishable categories. Diseases usually affect individuals not only physically, but also emotionally, as contracting and living with many diseases can alter one's perspective on life, and one's personality.

In the present context, the term "treatment", "treating" or "therapeutic intervention" relates to the management and care of a subject for the purpose of combating a condition such as a disease or disorder. The term is intended to include the full spectrum of treatments for a given condition from which the subject is suffering, such as administration of the therapeutically effective compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of an individual for the purpose of combating the disease, condition or disorder and includes the administration of the active compounds to prevent the onset of the symptoms or complications.

The term "therapeutic treatment" relates to any treatment which improves the health status and/or prolongs (increases) the lifespan of an individual. Said treatment may eliminate the disease in an individual, arrest or slow the development of a disease in an individual, inhibit or slow the development of a disease in an individual, decrease the frequency or severity of symptoms in an individual, and/or decrease the recurrence in an individual who currently has or who previously has had a disease.

The terms "prophylactic treatment" or "preventive treatment" relate to any treatment that is intended to prevent a disease from occurring in an individual. The terms "prophylactic treatment" or "preventive treatment" are used herein interchangeably.

The terms "individual" and "subject" are used herein interchangeably. They refer to a human or another mammal (e.g. mouse, rat, rabbit, dog, cat, cattle, swine, sheep, horse or primate) that can be afflicted with or is susceptible to a disease or disorder (e.g., cancer) but may or may not have the disease or disorder. In many embodiments, the individual is a human being. Unless otherwise stated, the terms "individual" and "subject" do not denote a particular age, and thus encompass adults, elderlies, children, and newborns. In embodiments of the present disclosure, the "individual" or "subject" is a "patient".

The term "patient" means an individual or subject for treatment, in particular a diseased individual or subject.

In one embodiment of the disclosure, the aim is to provide an immune response against diseased cells expressing an antigen such as cancer cells expressing a tumor antigen, and to treat a disease such as a cancer disease involving cells expressing an antigen such as a tumor antigen.

A pharmaceutical composition comprising RNA encoding a peptide or protein comprising an epitope may be administered to a subject to elicit an immune response against an antigen comprising said epitope in the subject which may be therapeutic or partially or fully protective. A person skilled in the art will know that one of the principles of immunotherapy and vaccination is based on the fact that an immunoprotective reaction to a disease is produced by immunizing a subject with an antigen or an epitope, which is immunologically relevant with respect to the disease to be treated. Accordingly, pharmaceutical compositions described herein are applicable for inducing or enhancing an immune response. Pharmaceutical compositions described herein are thus useful in a prophylactic and/or therapeutic treatment of a disease involving an antigen or epitope.

As used herein, "immune response" refers to an integrated bodily response to an antigen or a cell expressing an antigen and refers to a cellular immune response and/or a humoral immune response.

"Cell-mediated immunity", "cellular immunity", "cellular immune response", or similar terms are meant to include a cellular response directed to cells characterized by expression of an antigen, in particular characterized by presentation of an antigen with class I or class II MHC. The cellular response relates to cells called T cells or T lymphocytes which act as either "helpers" or "killers". The helper T cells (also termed $CD4^+$ T cells) play a central role by regulating the immune response and the killer cells (also termed cytotoxic T cells, cytolytic T cells, $CD8^+$ T cells or CTLs) kill diseased cells such as cancer cells, preventing the production of more diseased cells.

The present disclosure contemplates an immune response that may be protective, preventive, prophylactic and/or therapeutic. As used herein, "induces [or inducing] an immune response" may indicate that no immune response against a particular antigen was present before induction or it may indicate that there was a basal level of immune response against a particular antigen before induction, which was enhanced after induction. Therefore, "induces [or inducing] an immune response" includes "enhances [or enhancing] an immune response".

The term "immunotherapy" relates to the treatment of a disease or condition by inducing, or enhancing an immune response. The term "immunotherapy" includes antigen immunization or antigen vaccination.

The terms "immunization" or "vaccination" describe the process of administering an antigen to an individual with the purpose of inducing an immune response, for example, for therapeutic or prophylactic reasons.

The term "macrophage" refers to a subgroup of phagocytic cells produced by the differentiation of monocytes. Macrophages which are activated by inflammation, immune cytokines or microbial products nonspecifically engulf and kill foreign pathogens within the macrophage by hydrolytic and oxidative attack resulting in degradation of the pathogen. Peptides from degraded proteins are displayed on the macrophage cell surface where they can be recognized by T cells, and they can directly interact with antibodies on the B cell surface, resulting in T and B cell activation and further stimulation of the immune response. Macrophages belong to the class of antigen presenting cells. In one embodiment, the macrophages are splenic macrophages.

The term "dendritic cell" (DC) refers to another subtype of phagocytic cells belonging to the class of antigen presenting cells. In one embodiment, dendritic cells are derived from hematopoietic bone marrow progenitor cells. These progenitor cells initially transform into immature dendritic cells. These immature cells are characterized by high phagocytic activity and low T cell activation potential. Immature dendritic cells constantly sample the surrounding environment for pathogens such as viruses and bacteria. Once they have come into contact with a presentable antigen, they become activated into mature dendritic cells and begin to migrate to the spleen or to the lymph node. Immature dendritic cells phagocytose pathogens and degrade their proteins into small pieces and upon maturation present those fragments at their cell surface using MHC molecules. Simultaneously, they upregulate cell-surface receptors that act as co-receptors in T cell activation such as CD80, CD86, and CD40 greatly enhancing their ability to activate T cells. They also upregulate CCR7, a chemotactic receptor that induces the dendritic cell to travel through the blood stream to the spleen or through the lymphatic system to a lymph node. Here they act as antigen-presenting cells and activate helper T cells and killer T cells as well as B cells by presenting them antigens, alongside non-antigen specific co-stimulatory signals. Thus, dendritic cells can actively induce a T cell- or B cell-related immune response. In one embodiment, the dendritic cells are splenic dendritic cells.

The term "antigen presenting cell" (APC) is a cell of a variety of cells capable of displaying, acquiring, and/or presenting at least one antigen or antigenic fragment on (or at) its cell surface. Antigen-presenting cells can be distinguished in professional antigen presenting cells and non-professional antigen presenting cells.

The term "professional antigen presenting cells" relates to antigen presenting cells which constitutively express the Major Histocompatibility Complex class II (MHC class II) molecules required for interaction with naive T cells. If a T cell interacts with the MHC class II molecule complex on the membrane of the antigen presenting cell, the antigen presenting cell produces a co-stimulatory molecule inducing activation of the T cell. Professional antigen presenting cells comprise dendritic cells and macrophages.

The term "non-professional antigen presenting cells" relates to antigen presenting cells which do not constitutively express MHC class II molecules, but upon stimulation by certain cytokines such as interferon-gamma. Exemplary, non-professional antigen presenting cells include fibroblasts, thymic epithelial cells, thyroid epithelial cells, glial cells, pancreatic beta cells or vascular endothelial cells.

"Antigen processing" refers to the degradation of an antigen into procession products, which are fragments of said antigen (e.g., the degradation of a protein into peptides) and the association of one or more of these fragments (e.g., via binding) with MHC molecules for presentation by cells, such as antigen presenting cells to specific T cells.

The term "disease involving an antigen" refers to any disease which implicates an antigen, e.g. a disease which is characterized by the presence of an antigen. The disease involving an antigen can be an infectious disease, or a cancer disease or simply cancer. As mentioned above, the antigen may be a disease-associated antigen, such as a tumor-associated antigen, a viral antigen, or a bacterial antigen. In one embodiment, a disease involving an antigen is a disease involving cells expressing an antigen, preferably on the cell surface.

The term "infectious disease" refers to any disease which can be transmitted from individual to individual or from organism to organism, and is caused by a microbial agent (e.g. common cold). Infectious diseases are known in the art and include, for example, a viral disease, a bacterial disease, or a parasitic disease, which diseases are caused by a virus, a bacterium, and a parasite, respectively. In this regard, the infectious disease can be, for example, hepatitis, sexually transmitted diseases (e.g. chlamydia or gonorrhea), tuberculosis, HIV/acquired immune deficiency syndrome (AIDS), diphtheria, hepatitis B, hepatitis C, cholera, severe acute respiratory syndrome (SARS), the bird flu, and influenza.

The terms “cancer disease” or “cancer” refer to or describe the physiological condition in an individual that is typically characterized by unregulated cell growth. Examples of cancers include, but are not limited to, carcinoma, lymphoma, blastoma, sarcoma, and leukemia. More particularly, examples of such cancers include bone cancer, blood cancer lung cancer, liver cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, prostate cancer, uterine cancer, carcinoma of the sexual and reproductive organs, Hodgkin’s Disease, cancer of the esophagus, cancer of the small intestine, cancer of the endocrine system, cancer of the thyroid gland, cancer of the parathyroid gland, cancer of the adrenal gland, sarcoma of soft tissue, cancer of the bladder, cancer of the kidney, renal cell carcinoma, carcinoma of the renal pelvis, neoplasms of the central nervous system (CNS), neuroectodermal cancer, spinal axis tumors, glioma, meningioma, and pituitary adenoma. The term “cancer” according to the disclosure also comprises cancer metastases.

Combination strategies in cancer treatment may be desirable due to a resulting synergistic effect, which may be considerably stronger than the impact of a monotherapeutic approach. In one embodiment, the pharmaceutical composition is administered with an immunotherapeutic agent. As used herein “immunotherapeutic agent” relates to any agent that may be involved in activating a specific immune response and/or immune effector function(s). The present disclosure contemplates the use of an antibody as an immunotherapeutic agent. Without wishing to be bound by theory, antibodies are capable of achieving a therapeutic effect against cancer cells through various mechanisms, including inducing apoptosis, block components of signal transduction pathways or inhibiting proliferation of tumor cells. In certain embodiments, the antibody is a monoclonal antibody. A monoclonal antibody may induce cell death via antibody-dependent cell mediated cytotoxicity (ADCC), or bind complement proteins, leading to direct cell toxicity, known as complement dependent cytotoxicity (CDC). Non-limiting examples of anti cancer antibodies and potential antibody targets (in brackets) which may be used in combination with the present disclosure include: Abagovomab (CA-125), Abciximab (CD41), Adecatumumab (EpCAM), Afutuzumab (CD20), Alacizumab pegol (VEGFR2), Altumomab pentetate (CEA), Amatuximab (MORAb-009), Anatumomab mafenatox (TAG-72), Apolizumab (HLA-DR), Arcitumomab (CEA), Atezolizumab (PD-L1), Bavituximab (phosphatidylserine), Bectumomab (CD22), Belimumab (BAFF), Bevacizumab (VEGF-A), Bivatuzumab mertansine (CD44 v6), Blinatumomab (CD 19), Brentuximab vedotin (CD30 TNFRSF8), Cantuzumab mertansin (mucin CanAg), Cantuzumab ravtansine (MUC1), Capromab pendetide (prostatic carcinoma cells), Carlumab (CNT0888), Catumaxomab (EpCAM, CD3), Cetuximab (EGFR), Citatuzumab bogatox (EpCAM), Cixutumumab (IGF-1 receptor), Claudiximab (Claudin), Clivatuzumab tetraxetan (MUC1), Conatumumab (TRAIL-R2), Dacetuzumab (CD40), Dalotuzumab (insulin-like growth factor I receptor), Denosumab (RANKL), Detumomab (B-lymphoma cell), Drozitumab (DR5), Ecromeximab (GD3 ganglioside), Edrecolomab (EpCAM), Elotuzumab (SLAMF7), Enavatuzumab (PDL192), Ensituximab (NPC-1C), Epratuzumab (CD22), Ertumaxomab (HER2/neu, CD3), Etaracizumab (integrin αvβ3), Farletuzumab (folate receptor 1), FBTA05 (CD20), Ficlatuzumab (SCH 900105), Figitumumab (IGF-1 receptor), Flanvotumab (glycoprotein 75), Fresolimumab (TGF-β), Galiximab (CD80), Ganitumab (IGF-I), Gemtuzumab ozogamicin (CD33), Gevokizumab (ILIβ), Girentuximab (carbonic anhydrase 9 (CA-IX)), Glembatumumab vedotin (GPNMB), Ibritumomab tiuxetan (CD20), Icrucumab (VEGFR-1), Igovoma (CA-125), Indatuximab ravtansine (SDC1), Intetumumab (CD51), Inotuzumab ozogamicin (CD22), Ipilimumab (CD 152), Iratumumab (CD30), Labetuzumab (CEA), Lexatumumab (TRAIL-R2), Libivirumab (hepatitis B surface antigen), Lintuzumab (CD33), Lorvotuzumab mertansine (CD56), Lucatumumab (CD40), Lumiliximab (CD23), Mapatumumab (TRAIL-R1), Matuzumab (EGFR), Mepolizumab (IL5), Milatuzumab (CD74), Mitumomab (GD3 ganglioside), Mogamulizumab (CCR4), Moxetumomab pasudotox (CD22), Nacolomab tafenatox (C242 antigen), Naptumomab estafenatox (5T4), Namatumab (RON), Necitumumab (EGFR), Nimotuzumab (EGFR), Nivolumab (IgG4), Ofatumumab (CD20), Olaratumab (PDGF-R a), Onartuzumab (human scatter factor receptor kinase), Oportuzumab monatox (EpCAM), Oregovomab (CA-125), Oxelumab (OX-40), Panitumumab (EGFR), Patritumab (HER3), Pemtumoma (MUC1), Pertuzuma (HER2/neu), Pintumomab (adenocarcinoma antigen), Pritumumab (vimentin), Racotumomab (N-glycolylneuraminic acid), Radretumab (fibronectin extra domain-B), Rafivirumab (rabies virus glycoprotein), Ramucirumab (VEGFR2), Rilotumumab (HGF), Rituximab (CD20), Robatumumab (IGF-1 receptor), Samalizumab (CD200), Sibrotuzumab (FAP), Siltuximab (IL6), Tabalumab (BAFF), Tacatuzumab tetraxetan (alpha-fetoprotein), Taplitumomab paptox (CD 19), Tenatumomab (tenascin C), Teprotumumab (CD221), Ticilimumab (CTLA-4), Tigatuzumab (TRAIL-R2), TNX-650 (IL13), Tositumomab (CD20), Trastuzumab (HER2/neu), TRBS07 (GD2), Tremelimumab (CTLA-4), Tucotuzumab celmoleukin (EpCAM), Ublituximab (MS4A1), Urelumab (4-1 BB), Volociximab (integrin α5β1), Votumumab (tumor antigen CTAA 16.88), Zalutumumab (EGFR), and Zanolimumab (CD4).

Citation of documents and studies referenced herein is not intended as an admission that any of the foregoing is pertinent prior art. All statements as to the contents of these documents are based on the information available to the applicants and do not constitute any admission as to the correctness of the contents of these documents.

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

EXAMPLES

Example 1: Construct Design and RNA Production

In vitro transcription of vaccine RNA constructs was based on derivatives of the pCMV-Script-Vector (Stratagene) described previously (Holtkamp, Silke et al., 2006, *Blood* 108(13):4009-17). These plasmid constructs encode a T7 promoter, a 5' human α-globin-UTR, a 3' UTR of two sequential sequences of human β-globin and a poly(A) tail of either 100 nucleotides, with a linker after 70 nucleotides (OVA MHC class I and II, E7, non-coding RNA), or a poly(A)120 tail (OVA MHC class I RNA). The OVA constructs encode the H-2Kb-restricted, immunodominant epitope $OVA_{257-264}$ (SIINFEKL) (OVA MHC class I), or a fusion of the H-2Kb-restricted epitope with the I-Ad-restricted epitope $OVA_{323-339}$ (ISQAVHAAHAEINEAGR) (OVA MHC class I and II). The E7 construct encodes the full-length E7 protein of HPV 16 (Grunwitz, Christian et al., 2019, *OncoImmunology* 8(9):1-11). Non-coding RNA encodes the optimized backbone identical to the OVA MHC class I and II construct but the antigen sequence is replaced by a GS linker (GGSGGGGSGGGGSGGGGSGG). All vaccine RNA constructs are equipped with the secretion signal for routing to the endoplasmic reticulum and the transmembrane domain derived from human MHC class I (MITD) for improved presentation of MHC class I and II epitopes as described previously (OVA MHC class I RNA, E7 RNA) (Kreiter, Sebastian et al., 2008, The Journal of Immunology 180(1):309-18), or the analogous murine sequences (OVA MHC class I and II RNA, non-coding RNA). RNA was generated by in vitro transcription as described by Kreiter et al. (Kreiter, Sebastian et al., 2007, Cancer Immunology, Immunotherapy: CII 56(10):1577-87). RNA was capped with a β-5-ARCA cap 0. For the synthesis of modified RNA (modRNA), the normal nucleoside uridine was substituted by 1-methyl-pseudouridine (Pardi, Norbert et al., 2015, Journal of Controlled Release: Official Journal of the Controlled Release Society 217:345-51) and double-stranded (dsRNA) molecules were depleted (Baiersdörfer, Markus et al., 2019, *Molecular Therapy—Nucleic Acids* 15(April)). Standard vaccine RNA (stdRNA) was neither nucleoside-modified nor dsRNA-purified. RNA was eluted in $H_2O$ and stored at 80° C. until further use.

In vitro transcription of cytokine encoding RNA was based on the pST1-GG-TEV-MCS-FI-A30LA70 or the pST4-GG-TEV-MCS-FI-A30LA70 plasmid-backbone and derivative DNA-constructs. These plasmid constructs contain the 5' leader sequence of tobacco etch virus (TEV), a 3' FI element (where F is a 136 nucleotide long 3'-UTR fragment of amino-terminal enhancer of split RNA and I is a 142 nucleotide long fragment of mitochondrially encoded 12S RNA both identified in *Homo sapiens*; WO 2017/060314) and a poly(A) tail of 100 nucleotides, with a linker after 70 nucleotides. The cytokine encoding sequence contains the sequence of IFNα4 originating from *Mus musculus* (NP_034634.1) where the native secretion signal sequence is replaced by a signal peptide sequence of murine MHC class I based on the human sequence described by Kreiter et al. (Kreiter, Sebastian et al., 2008, The Journal of Immunology 180(1):309-18). No changes in the resulting amino acid sequences were introduced.

RNA was generated by in vitro transcription as described by Kreiter et al. (Kreiter, Sebastian et al., 2007, Cancer Immunology, Immunotherapy: CII 56(10):1577-87). For all cytokine encoding RNA constructs, the normal nucleoside uridine was substituted by 1-methyl-pseudouridine. Resulting RNA constructs were equipped with a Cap1-structure and double-stranded (dsRNA) molecules were depleted. Purified RNA was eluted in $H_2O$ and stored at −80° C. until further use.

In vitro transcription of all described RNA constructs was carried out at BioNTech RNA Pharmaceuticals GmbH. A list of all cytokine RNA constructs used in subsequent experiments is shown in Table 1.

Vaccine- and cytokine-encoding RNA was formulated with liposomes composed of DOTMA and DOPE to yield RNA-lipoplexes (RNA-LPX) with a negative net charge for targeting of lymphoid compartments by intravenous administration (Kranz, Lena Mareen et al., 2016, *Nature* 534 (7607):396-401).

TABLE 1

| | Amino acid sequence of RNA encoded and expressed IFNα4. |
|---|---|
| IFNα4 | MGAMAPRTLLLLLAAALAPTQTRAGPGSCDLPHTYNLGNKRALT VLEEMRRLPPLSCLKDRKDFGFPLEKVDNQQIQKAQAILVLRDL TQQILNLFTSKDLSATWNATLLDSFCNDLHQQLNDLKACVMQEP PLTQEDSLLAVRTYFHRITVYLRKKKHSLCAWEVIRAEVWRALS SSTNLLARLSEEKE |

Example 2: Vaccination with modRNA Restricts Immune Activation and IFNα Release Compared to stdRNA We characterized the effects on different immune cell types and systemic IFNα levels in response to RNA vaccination with standard RNA-LPX (stdRNA) compared to modified RNA-LPX (modRNA). C57BL/6 mice (n=3 per group) were vaccinated intravenously (i.v.) with 10 μg stdRNA-LPX or modRNA-LPX not coding for an antigen sequence (non-coding RNA). Control mice received NaCl. Expression of stimulation- and migration associated molecules CD40 and CD86 on splenic cDCs and plasmacytoid DCs (pDCs) and CD69 on lymphoid cell subsets was determined 24 hours after injection by flow cytometry. Systemic release of IFNα was measured 6 hours after i.v. injection of RNA-LPX by serum ELISA.

Figure 1:
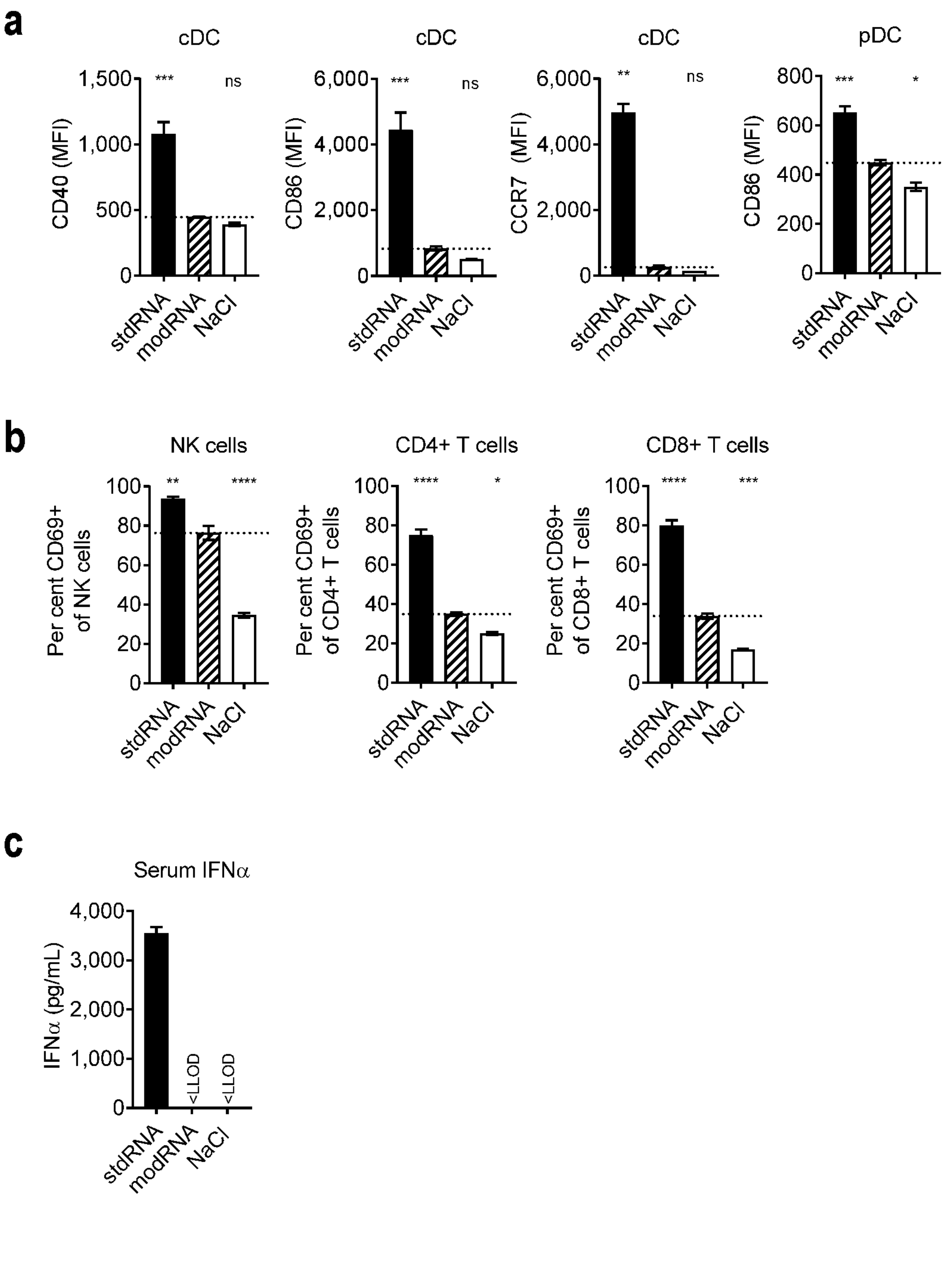
FIG. 1: modRNA restricts inflammatory signals in comparison to stdRNA.

Vaccination with stdRNA led to an upregulation of the costimulatory markers CD40 and CD86. Similarly, pDCs increased surface expression of CD86. In contrast, modRNA vaccination did not lead to any significant upregulation of these activation-associated markers on cDCs, and only slight upregulation on pDCs While cDCs drastically increased the migration-associated chemokine receptor 7 (CCR7) in response to stdRNA, modRNA failed to induce any significant expression above baseline (FIG. 1*a*).

The fraction of CD4+ and CD8+ T cells expressing CD69 substantially increased in response to stdRNA vaccination compared to the control. Vaccination with modRNA, on the other hand, stimulated CD69 expression in T cells to a much lower extent. NK cells seem to be more sensitive to modRNA than T cells and upregulated CD69 on a higher fraction of cells compared to the control. Yet, the CD69 positive fraction remained significantly below that observed in response to stdRNA (FIG. 1*b*).

Immune cell activation induced by stdRNA vaccination was accompanied by the secretion of high levels of systemic IFNα. In contrast, IFNα release was not detected above background upon vaccination with modRNA (FIG. 1*c*).

In summary, modRNA vaccination hardly triggers immune activation and does not lead to IFNα release. These findings indicate that the adjuvanticity of RNA vaccination can be controlled with modRNA.

Example 3: Effects of modRNA Vaccination can be Mimicked by stdRNA Vaccination Combined with IFNAR Signaling Blockade In order to investigate whether the immunosilent phenotype induced by vaccination with modRNA compared to the immune-activated phenotype triggered by stdRNA vaccination was a direct result of missing IFNα, IFNα signalling was blocked prior to vaccination with stdRNA. C57BL/6 mice (n=3 per group) were injected i.v. with 40 μg modRNA-LPX or stdRNA-LPX coding for HPV16 E7 and treated or not with 100 μg anti-IFNα receptor-1 (anti-IFNAR1) antibody treatment i.p. 5 hours prior to vaccination. Control mice received NaCl. Expression of stimulation-associated molecule CD86 on splenic cDCs and pDCs and CD69 on lymphoid cell subsets was determined 24 hours after injection by flow cytometry. Systemic release of IFNα was measured 1, 3, 6 and 24 hours after i.v. injection of RNA-LPX by serum ELISA. Blocking IFNα signalling in combination with stdRNA vaccination reduced CD86 expression on cDCs and pDCs at least to the level of modRNA (FIG. 2*a*). Expression of CD69 on NK cells, CD4+ T cells, CD8+ T cells and B cells remained similarly low in response to stdRNA vaccination under IFNAR1 blockade compared to stdRNA vaccination alone, and remained in the range of CD69 expression induced by modRNA vaccination (FIG. 2*b*). In line with the activation profile of splenic immune cells, blocking IFNα signaling resulted in reduced levels of systemic IFNα over all time points in response to stdRNA vaccination under IFNAR1 blocking conditions compared to stdRNA vaccination alone, yet they were significantly higher than those induced by modRNA vaccination (FIG. 2*c*).

Taken together, these findings show that the immunosilent environment induced by modRNA can be mimicked by blocking IFNAR signaling, indicating that the lack of IFNα in response to modRNA vaccination causes the immunosilent phenotype.

Example 4: T Cell Responses Induced by Vaccination with modRNA are Less in Numbers, Less Differentiated and do not Secrete Cytotoxic Cytokines Compared to stdRNA Next, we investigated the potency of modRNA to expand antigen-specific CD8+ T cells. C57BL/6 mice (n=3-5 per group) were vaccinated i.v. (day 0, 7) with 5 or 20 μg stdRNA-LPX or modRNA-LPX coding for the H-2Kb-restricted immunodominant epitope of chicken ovalbumin (OVA). Control mice received NaCl. Expansion and differentiation of antigen-specific CD8+ T cells in peripheral blood were determined by MHC class I tetramer staining and staining for CD127 and KLRG1 by flow cytometry five days after each vaccination. Functionality of splenic CD8+ T cells was investigated by analysis of IFNγ and TNFα secretion after ex vivo restimulation five days after the second vaccination.

Both stdRNA and modRNA led to a significant increase of OVA antigen-specific CD8+ T cells after two vaccinations, with modRNA inducing significantly less antigen-specific CD8+ T cells. Expansion of antigen-specific CD8+ T cells was delayed in response to modRNA compared to stdRNA vaccination. (FIG. 3*a*). In addition, modRNA vaccination induced less differentiated T cells than stdRNA vaccination, indicated by higher numbers of KLRG1− CD127+ memory precursor effector cells (MPEC) and less CD127− KLRG1+ short-lived effector cells (SLEC) especially after the second vaccination (FIG. 3*b*). Vaccination with modRNA resulted in a significantly smaller fraction of CD8+ T cells secreting the cytokines IFNγ and TNFα compared to stdRNA vaccination (FIG. 3*c*).

In summary, modRNA vaccination is capable of expanding antigen-specific CD8+ T cells, albeit less efficiently, and restrains T-cell differentiation into functional effector cells.

Example 5: Modified RNA-Encoded IFNα Provides Immune Activation

As shown in example 2, IFNα plays a major role in establishing an inflammatory environment upon vaccination. In order to characterize IFNα-dependent immune activation further, C57BL/6 mice (n=3 per group) were treated once with modified RNA-LPX coding for IFNα i.v. at low (0.1, 1, 5 μg) and high (5, 10, 20 μg) doses. Again, CD86 expression on splenic cDCs, pDCs and CD69 on lymphoid cell subsets was determined 24 hours after injection, and systemic IFNα release was analyzed 6 hours after injection. Treatment with IFNα RNA resulted in a dose-dependent increase of CD86 on cDCs and pDCs (FIG. 4*a, d*). Already the lowest dose of 0.1 μg IFNα RNA led to an upregulation of CD86 on cDCs and pDCs above the control level. In accordance with the activation profile of APCs, NK cells, CD4+ and CD8+ T cells and B cells increased CD69 expression dose-dependently upon treatment with IFNα RNA (FIG. 4*b, e*). Similarly, systemic release of IFNα correlated positively with the dose of co-delivered IFNα RNA (FIG. 4*c, f*).

In conclusion, RNA-encoded IFNα creates a proinflammatory environment indicated by activation of immune cells and systemic FNα secretion, which can be modulated in a dose-dependent manner.

Example 6: Combination of modRNA Vaccination with IFNα RNA Fully Rescues T Cell Expansion and Differentiation into Effector Cytokine-Producing Effectors Since IFNα was demonstrated to be capable of inducing a proinflammatory environment (FIG. 4), and that the mode of action of stdRNA vaccination depends in part on the vaccine-induced IFNα (FIG. 1-3), (Kranz, Lena Mareen et al., 2016, *Nature* 534(7607):396-401), it was investigated whether RNA-encoded IFNα would be able to improve T cell immunity induced by modRNA vaccination to a level comparable to that generated by stdRNA vaccination.

C57BL/6 mice (n=3-5 per group) were treated with 5 μg modRNA-LPX coding for OVA in combination with 0.1, 1 or 5 μg IFNα RNA three times (day 0, 7, 14). 10 μg stdRNA-LPX coding for OVA served as positive control, and 5 μg non-coding instead of IFNα-coding RNA-LPX together with modRNA-LPX coding for OVA, or NaCl only, as negative controls. Systemic release of IFNα was determined 6 hours after the first treatment. Expansion and differentiation of antigen-specific CD8+ T cells were determined five days after the third treatment (day 19; priming phase) and on day 102 and day 111 (memory phase) in peripheral blood and spleen as described by MHC class I tetramer staining and staining for CD127 and KLRG1 by flow cytometry. Functionality of splenic antigen-specific CD8+ T cells was investigated by analysis of IFNγ secretion after ex vivo restimulation.

The combination of modRNA vaccination with 5 μg IFNα RNA slightly increased systemic IFNα above negative control levels, while neither of the lower doses of IFNα RNA induced systemic levels. As expected, vaccination with stdRNA induced high levels of systemic IFNα. (FIG. 5*a*). Although only the combination of modRNA vaccination with 5 μg IFNα RNA had an effect on systemic IFNα levels, all IFNα RNA doses led to a dose-dependent increase of antigen-specific CD8+ T cells compared to modRNA vaccination combined with non-coding RNA after the third treatment in peripheral blood and in the spleen (FIG. 5*b*, upper panels). The group treated with 5 μg RNA expanded antigen-specific CD8+ T cells to the positive control level of stdRNA in the spleen. Initial expansion of antigen-specific CD8+ T cells after three treatments correlated well with the size of the memory pool of antigen-specific CD8+ T cells on day 102 and 111 (FIG. 5*b* lower panels), Treatment with 1 and 5 μg IFNα RNA in combination with modRNA increased the ability of antigen-specific CD8+ T cells to secrete effector cytokine IFNγ upon restimulation compared to modRNA combined with non-coding RNA (FIG. 5*c*, left). In contrast, 0.1 μg IFNα had no measurable effect on the functionality of CD8+ T cells. The majority of CD8+ T cells secreting IFNγ were SLECs and this population correlated positively with the IFNα dose (FIG. 5*c*, right).

Co-delivered IFNα RNA affected T-cell differentiation by increasing the fraction of SLECs and decreasing the fraction of MPECs among antigen-specific CD8+ T cells dose-dependently compared to modRNA combined with non-coding RNA. The percentage of SLECs in the group treated with 5 μg IFNα RNA in combination with modRNA vaccination reached up to the mean of expanded SLECs with stdRNA alone after three vaccinations in the spleen (FIG. 5*d*, upper and middle panels). These trends after priming (day 19) were maintained throughout contraction (day 111), while MPECs increased and SLECs decreased over time in all groups (FIG. 5*d*, middle and lower panels). As seen after priming, the fraction of SLECs correlated positively and the portion of MPECs inversely with IFNα dose at the memory time point (day 111).

These findings demonstrate that combination of modRNA vaccination with IFNα RNA influenced proliferation, differentiation, function and memory development of antigen-specific CD8+ T cells IFNα dose dependently.

The invention claimed is:

1. A medical preparation comprising:

(i) non-immunogenic RNA encoding a peptide or protein comprising an epitope for inducing an immune response against an antigen in a subject; and (ii) non-immunogenic RNA encoding interferon α, wherein the non-immunogenic RNA is rendered non-immunogenic by the incorporation of modified nucleosides and the removal of double-stranded RNA (dsRNA).

2. The medical preparation of claim 1, which is for treating a disease, disorder or condition associated with expression or elevated expression of an antigen.

3. The medical preparation of claim 1, wherein (i) the antigen is a tumor-associated antigen; or (ii) the disease, disorder or condition is cancer.

4. The medical preparation of claim 1 wherein:

a) the non-immunogenic RNA when administered results in reduced activation of dendritic cells, activation of T cells and/or secretion of IFN-alpha compared to standard RNA; or b) the non-immunogenic RNA encoding interferon α, is mRNA or in vitro transcribed RNA.

5. The medical preparation of claim 1, wherein the modified nucleosides suppress RNA-mediated activation of innate immune receptors and/or comprise a replacement of one or more uridines with a nucleoside comprising a modified nucleobase, such as a modified uracil, wherein optionally the nucleoside comprising a modified nucleobase is selected from the group consisting of 3-methyl-uridine (m3U), 5-methoxy-uridine (mo5U), 5-aza-uridine, 6-aza-uridine, 2-thio-5-aza-uridine, 2-thio-uridine (s2U), 4-thio-uridine (s4U), 4-thio-pseudouridine, 2-thio-pseudouridine, 5-hydroxy-uridine (ho5U), 5-aminoallyl-uridine, 5-halo-uridine (e.g., 5-iodo-uridineor 5-bromo-uridine), uridine 5-oxyacetic acid (cmo5U), uridine 5-oxyacetic acid methyl ester (mcmo5U), 5-carboxymethyl-uridine (cm5U), 1-carboxymethyl-pseudouridine, 5-carboxyhydroxymethyl-uridine (chm5U), 5-carboxyhydroxymethyl-uridine methyl ester (mchm5U), 5-methoxycarbonylmethyl-uridine (mcm5U), 5-methoxycarbonylmethyl-2-thio-uridine (mcm5s2U), 5-aminomethyl-2-thio-uridine (nm5s2U), 5-methylaminomethyl-uridine (mnm5U), 1-ethyl-pseudouridine, 5-methylaminomethyl-2-thio-uridine (mnm5s2U), 5-methylaminomethyl-2-seleno-uridine (mnm5se2U), 5-carbamoylmethyl-uridine (ncm5U), 5-carboxymethylaminomethyl-uridine (cmnm5U), 5-carboxymethylaminomethyl-2-thio-uridine (cmnm5s2U), 5-propynyl-uridine, 1-propynyl-pseudouridine, 5-taurinomethyl-uridine (τm5U), 1-taurinomethyl-pseudouridine, 5-taurinomethyl-2-thio-uridine (tm5s2U), 1-taurinomethyl-4-thio-pseudouridine, 5-methyl-2-thio-uridine (m5s2U), 1-methyl-4-thio-pseudouridine (m1s4ψ), 4-thio-1-methyl-pseudouridine, 3-methyl-pseudouridine (m3w), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyl-dihydrouridine (m5D), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine, 3-(3-amino-3-carboxypropyl) uridine (acp3U), 5-1-methyl-3-(3-amino-3-carboxypropyl)

pseudouridine (acp3 ψ), (isopentenylaminomethyl) uridine (inm5U), 5-(isopentenylaminomethyl)-2-thio-uridine (inm5s2U), α-thio-uridine, 2'-O-methyl-uridine (Um), 5,2'-O-dimethyl-uridine (m5Um), 2'-O-methyl-pseudouridine (ψm), 2-thio-2'-O-methyl-uridine (s2Um), 5-methoxycarbonylmethyl-2'-O-methyl-uridine (mcm5Um), 5-carbamoylmethyl-2'-O-methyl-uridine (ncm5Um), 5-carboxymethylaminomethyl-2'-O-methyl-uridine (cmnm5Um), 3,2'-O-dimethyl-uridine (m3Um), 5-(isopentenylaminomethyl)-2'-O-methyl-uridine (inm5Um), 1-thio-uridine, deoxythymidine, 2'-F-ara-uridine, 2'-F-uridine, 2'-OH-ara-uridine, 5-(2-carbomethoxyvinyl) uridine, and 5-[3-(1-E-propenylamino) uridine, the nucleoside comprising a modified nucleobase preferably being pseudouridine (ψ), N1-methyl-pseudouridine ($m^1ψ$) or 5-methyl-uridine (m5U), the nucleoside comprising a modified nucleobase most preferably being 1-methyl-pseudouridine.

6. The medical preparation of claim 1, wherein (i) the non-immunogenic RNA encoding a peptide or protein comprising an epitope is present in a formulation for targeting the lymphatic system and/or dendritic cells, such as immature dendritic cells; and/or (ii) wherein the RNA encoding an immunostimulant is administered in a formulation for targeting the lymphatic system, the liver and or secondary lymphoid organs, in particular spleen.

7. The medical preparation of claim 1, wherein:

(i) the non-immunogenic RNA encoding a peptide or protein comprising an epitope and the non-immunogenic RNA encoding interferon α are present in a common or separate formulation;

(ii) the medical preparation is a kit;

(iii) the medical preparation comprises the non-immunogenic RNA encoding a peptide or protein comprising an epitope and the non-immunogenic RNA encoding interferon α in a pharmaceutical composition;

(iv) the medical preparation comprises the non-immunogenic RNA encoding a peptide or protein comprising an epitope and non-immunogenic RNA encoding interferon α in separate containers;

(v) the medical preparation further comprises instructions for using the medical preparation; and/or (vi) the medical preparation is a pharmaceutical composition.

8. The medical preparation of claim 1 for pharmaceutical use.

9. The medical preparation of claim 8, wherein the pharmaceutical use comprises a therapeutic or prophylactic treatment of a disease or disorder.

10. The medical preparation of claim 9, wherein the disease or disorder is cancer.

* * * * *